United States Patent
Yen et al.

(10) Patent No.: US 10,472,564 B2
(45) Date of Patent: Nov. 12, 2019

(54) DELAYED FLUORESCENCE COMPOUND AND ORGANIC ELECTROLUMINESCENT DEVICE USING THE SAME

(71) Applicants: Feng-Wen Yen, Taipei (TW); Wen-Feng Hsiao, Nantou (TW)

(72) Inventors: Feng-Wen Yen, Taipei (TW); Wen-Feng Hsiao, Nantou (TW)

(*) Notice: Subject to any disclaimer, the term of this patent is extended or adjusted under 35 U.S.C. 154(b) by 193 days.

(21) Appl. No.: 15/715,177

(22) Filed: Sep. 26, 2017

(65) Prior Publication Data
US 2019/0093009 A1    Mar. 28, 2019

(51) Int. Cl.
| | |
|---|---|
| C09K 11/06 | (2006.01) |
| C07D 495/20 | (2006.01) |
| H01L 51/00 | (2006.01) |
| H01L 51/50 | (2006.01) |

(52) U.S. Cl.
CPC ........ *C09K 11/06* (2013.01); *C07D 495/20* (2013.01); *H01L 51/0067* (2013.01); *H01L 51/0071* (2013.01); *H01L 51/0072* (2013.01); *H01L 51/0074* (2013.01); *C09K 2211/1018* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC .......... C07D 495/20; C09K 11/06; C09K 2211/1018; H01L 51/0067; H01L 51/0071; H01L 51/0072; H01L 51/0074; H01L 51/5012; H01L 51/5016; H01L 51/5056; H01L 51/5072; H01L 51/5088; H01L 51/5092; H01L 51/5096
See application file for complete search history.

(56) References Cited

U.S. PATENT DOCUMENTS

| | | | | |
|---|---|---|---|---|
| 10,249,828 B2* | 4/2019 | Stoessel | ........ | C09K 11/06 |
| 2014/0138669 A1* | 5/2014 | Nakagawa | ........ | H05B 33/14 |
| | | | | 257/40 |
| 2016/0093823 A1* | 3/2016 | Seo | ........ | H01L 51/5016 |
| | | | | 257/40 |
| 2019/0123284 A1* | 4/2019 | Yen | ........ | H01L 51/0071 |

FOREIGN PATENT DOCUMENTS

| | | | |
|---|---|---|---|
| CN | 107915746 | * | 4/2018 |
| DE | 102016120373 B3 | * | 8/2017 |
| WO | 2016/08062 A1 | | 5/2016 |
| WO | WO 2016/091219 A1 | * | 6/2016 |
| WO | WO 2016/116521 A1 | * | 7/2016 |
| WO | 2017/057976 A1 | | 4/2017 |

\* cited by examiner

*Primary Examiner* — Dawn L Garrett

(57) ABSTRACT

The present invention discloses a delayed fluorescence compound and the organic electroluminescent device employing the delayed fluorescence compound as the delayed fluorescence dopant material, the delayed fluorescence host material, or the phosphorescent host material in the light emitting layer, and/or used in the hole blocking layer and/or the electron transporting layer of the organic EL device, which thereby displays good performance.

19 Claims, 2 Drawing Sheets

DELAYED FLUORESCENCE COMPOUND AND ORGANIC ELECTROLUMINESCENT DEVICE USING THE SAME

FIELD OF INVENTION

The present invention relates to a delayed fluorescence compound and an organic electroluminescent device using the same and, more particularly, to a thermally activated delayed fluorescence compound that is useful in organic light-emitting devices.

BACKGROUND OF THE INVENTION

The first observation of electroluminescence in organic materials was in the early 1950s by Andre Bernanose and his co-workers at Nancy-University in France. In 1963, Martin Pope and his co-workers at New York University first observed direct current (DC) electroluminescence on a single pure crystal of anthracene and on anthracene crystals doped with tetracene under vacuum. The first diode device was created by Ching W. Tang and Steven Van Slyke at Eastman Kodak in 1987. The diode device used a two-layer structure with separate hole transporting and electron transporting layers, resulting in reduction of operating voltage and improvement of the efficiency, thereby leading to the current era of organic EL research and device production.

Typically, organic EL device is composed of organic material layers sandwiched between two electrodes. The organic material layers include the hole transporting layer, the light emitting layer, and the electron transporting layer. The basic mechanism of organic EL involves the injection, transport, and recombination of carriers as well as exciton formation for emitting light. When an external voltage is applied across the organic EL device, electrons and holes are injected from the cathode and the anode, respectively. Subsequently, the electrons recombine with holes in the light emitting layer to form excitons and then emit light. The structure design of the organic material layers and the selection of anode and cathode are critical for the OLED device to fully exhibit luminous efficacy.

In subsequent studies, it was found that when the light emitting layer is sandwiched between $Alq_3$ and NPB, OLED can be improved by doping the light emitting layer with a dopant such that the light energy of the host can be transferred to the dopant for changing the color of light. Therefore, the red, blue, and green light emitting OLED devices could be obtained, which makes OLED advance greatly toward the full-color display. However, in such a situation, the researchers have to consider the physical properties of the materials themselves, such as the energy level difference, thermal properties, morphology, etc. so as to find the optimum materials. The researchers need to do the research and improvement repeatedly in order to meet the requirements.

Organic EL is applied to flat panel displays due to their high illumination, low weight, ultra-thin profile, self-illumination without backlight, low power consumption, wide viewing angle, high contrast, simple fabrication processes and rapid response time. In OLED development, a full-color flat-panel display is the highest goal in development. At present, the red, blue and green doping materials have been successfully developed, but have not yet reached a satisfactory level. There still exists a need to continue research and development of new and better doping materials. In addition, white light OLED is also a recent research focus and expected to be used as a lighting source or LCD screen backlight so as to significantly reduce the volume and weight of the display device using the conventional white light source.

Recently, a new type of fluorescent organic EL device has been developed by Adachi and coworkers. The new organic EL device incorporates the mechanism of thermally activated delayed fluorescence (TADF), which is a promising way to obtain a high efficiency of exciton formation by converting spin-forbidden triplet excitons up to the singlet level through the mechanism of reverse intersystem crossing (RISC). However, there still exists a need for the compound with TADF property and high luminous efficiency.

SUMMARY OF THE INVENTION

According to the reasons described above, an object of the present invention is to provide a novel compound with TADF property and high luminous efficiency. The present invention discloses a delayed fluorescence compound of formula (1), which is used as a delayed fluorescence dopant material, a delayed fluorescence host material, or a phosphorescent host material in a light emitting layer, and/or used in a hole blocking layer and/or an electron transporting layer in order to lower driving voltage and power consumption and to increase luminous efficiency of the organic EL device.

The present invention has the economic advantages for industrial practice. Accordingly, a delayed fluorescence compound that can be used in organic EL devices is disclosed. The delayed fluorescence compound is represented by the following formula (1):

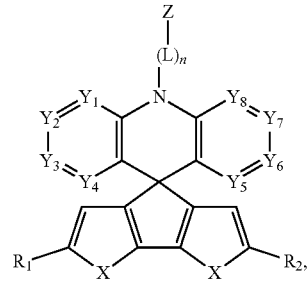

formula (1)

wherein X is O, S, or Se; $Y_1$-$Y_8$ are each independently a nitrogen atom or CR; R, $R_1$, and $R_2$ are each independently selected from the group consisting of a hydrogen atom, a halide, a nitro, a pyridine, a pyrazine, a pyrimidine, a pyridazine, a substituted or unsubstituted alkyl group having 1 to 30 carbon atoms, a substituted or unsubstituted alkenyl group having 1 to 30 carbon atoms, a substituted or unsubstituted aryl group having 6 to 30 carbon atoms, and a substituted or unsubstituted heteroaryl group having 3 to 30 carbon atoms; L represents formula (2):

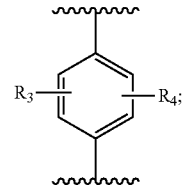

formula (2)

n is 0 or 1; and Z is selected from formulas (3)-(7):

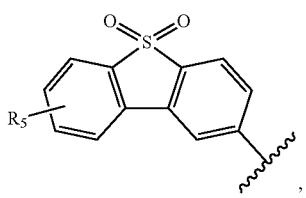
formula (3)

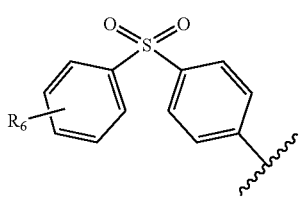
formula (4)

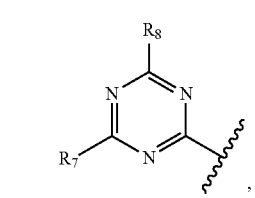
formula (5)

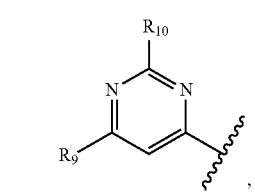
formula (6)

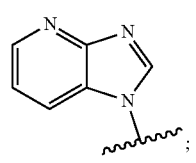
formula (7)

and
wherein $R_3$ to $R_{10}$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted heteroaryl group having 3 to 30 carbon atoms, and a substituted or unsubstituted aralkyl group having 6 to 30 carbon atoms; $Y_2$ and $Y_3$ are optionally connected to each other to form an aromatic or heteroaromatic ring; and $Y_6$ and $Y_7$ are optionally connected to each other to form an aromatic or heteroaromatic ring.

The present invention further discloses an organic electroluminescent device. The organic electroluminescent device comprises a pair of electrodes composed of a cathode and an anode, and a light emitting layer and one or more organic thin film layers between the pair of electrodes. At least one of the light emitting layer and the organic thin film layer comprises the delayed fluorescence compound of formula (1).

DESCRIPTION OF THE PREFERRED EMBODIMENTS

Figure 1:
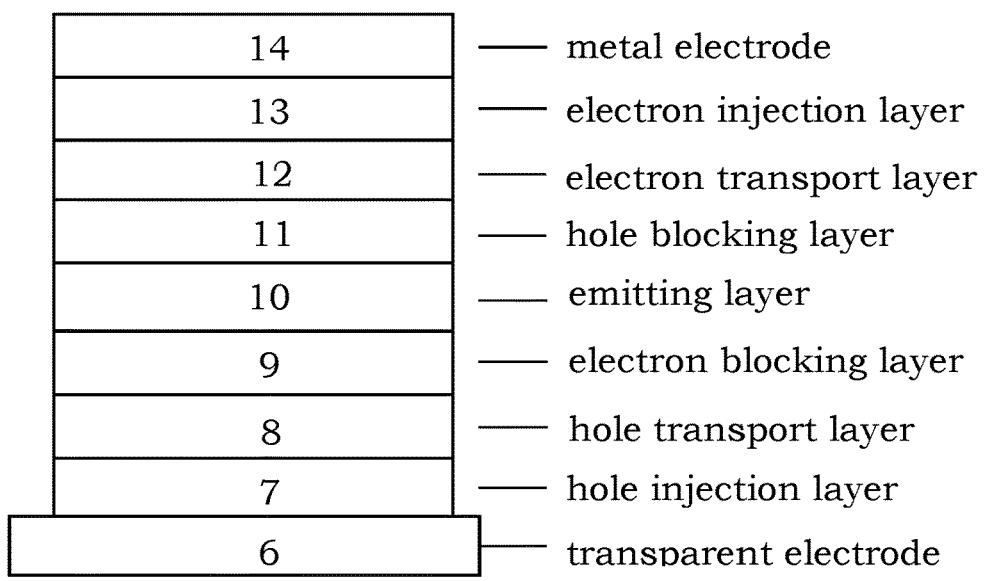
FIG. 1 is a schematic view showing an embodiment of the organic EL device of the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is emitting layer which is deposited onto 9, 11 is hole blocking layer which is deposited onto 10, 12 is electron transport layer which is deposited on to 11, and 13 is electron injection layer which is deposited on to 12.

What probed into the invention is the delayed fluorescence compound and organic EL device using the compound. Detailed descriptions of the production, structure and elements will be provided as follows such that the invention can be fully understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, a delayed fluorescence compound is disclosed. The delayed fluorescence compound is represented by the following formula (1):

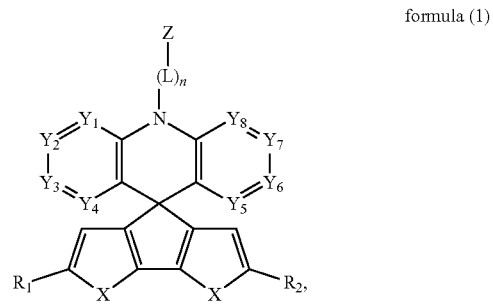
formula (1)

wherein X is O, S, or Se; $Y_1$-$Y_8$ are each independently a nitrogen atom or CR; R, $R_1$, and $R_2$ are each independently selected from the group consisting of a hydrogen atom, a halide, a nitro, a pyridine, a pyrazine, a pyrimidine, a pyridazine, a substituted or unsubstituted alkyl group having 1 to 30 carbon atoms, a substituted or unsubstituted alkenyl group having 1 to 30 carbon atoms, a substituted or unsubstituted aryl group having 6 to 30 carbon atoms, and a substituted or unsubstituted heteroaryl group having 3 to 30 carbon atoms; L represents formula (2):

formula (2)

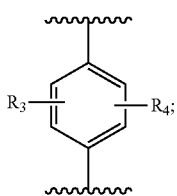

n is 0 or 1; and Z is selected from formulas (3)-(7):

formula (3)

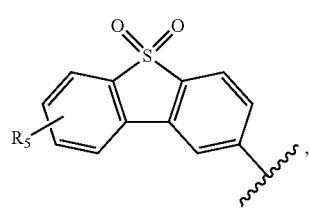

formula (4)

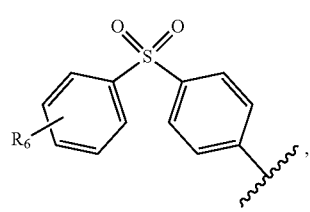

formula (5)

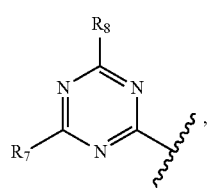

formula (6)

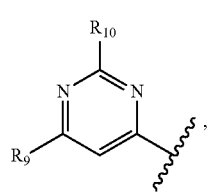

formula (7)

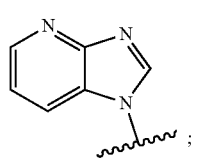

and
wherein $R_3$ to $R_{10}$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted heteroaryl group having 3 to 30 carbon atoms, and a substituted or unsubstituted aralkyl group having 6 to 30 carbon atoms; $Y_2$ and $Y_3$ are optionally connected to each other to form an aromatic or heteroaromatic ring; and $Y_6$ and $Y_7$ are optionally connected to each other to form an aromatic or heteroaromatic ring.

Preferably, the delayed fluorescence compound of formula (1) is one of the following compounds:

C1

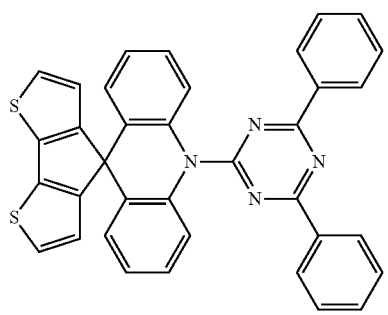

C2

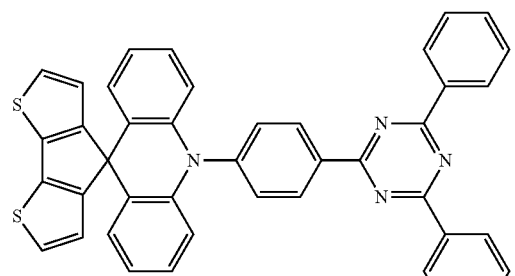

C3

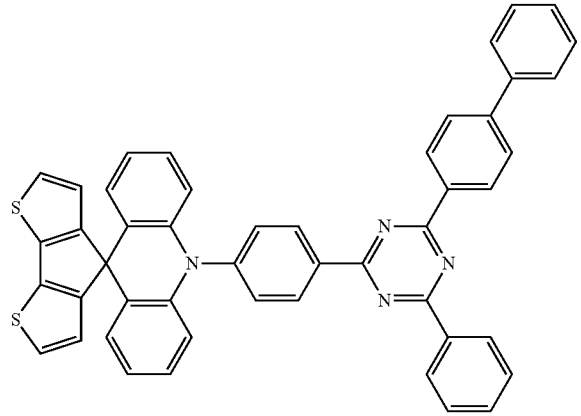

C4

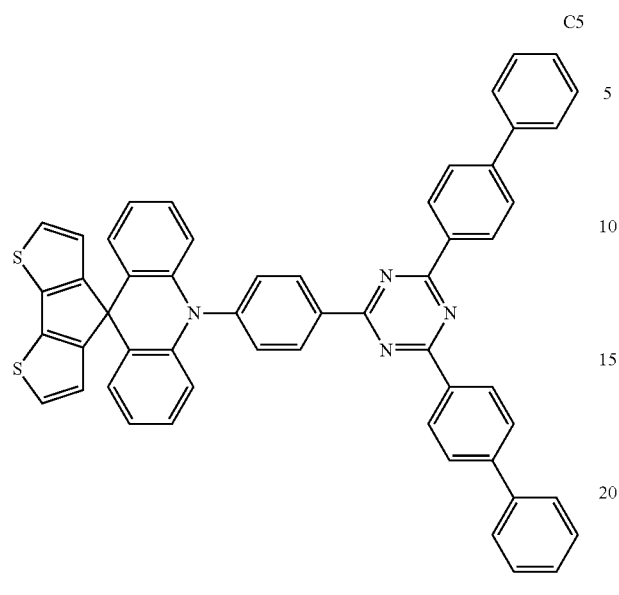
C5
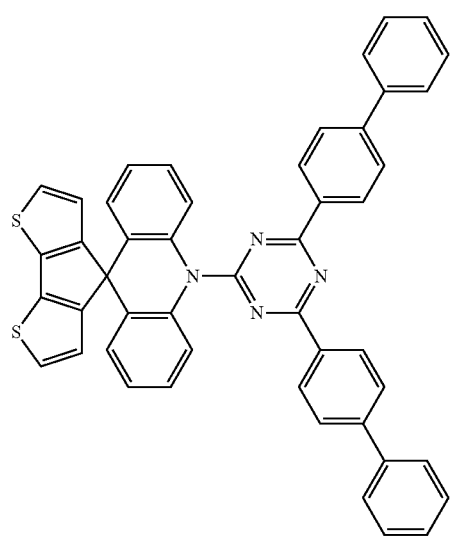
C8
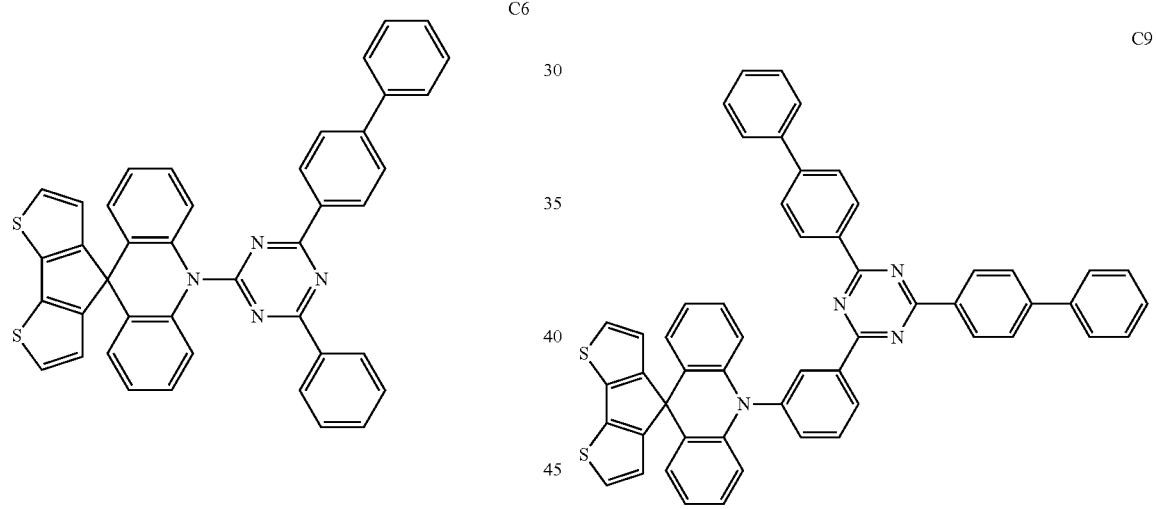
C6
C9
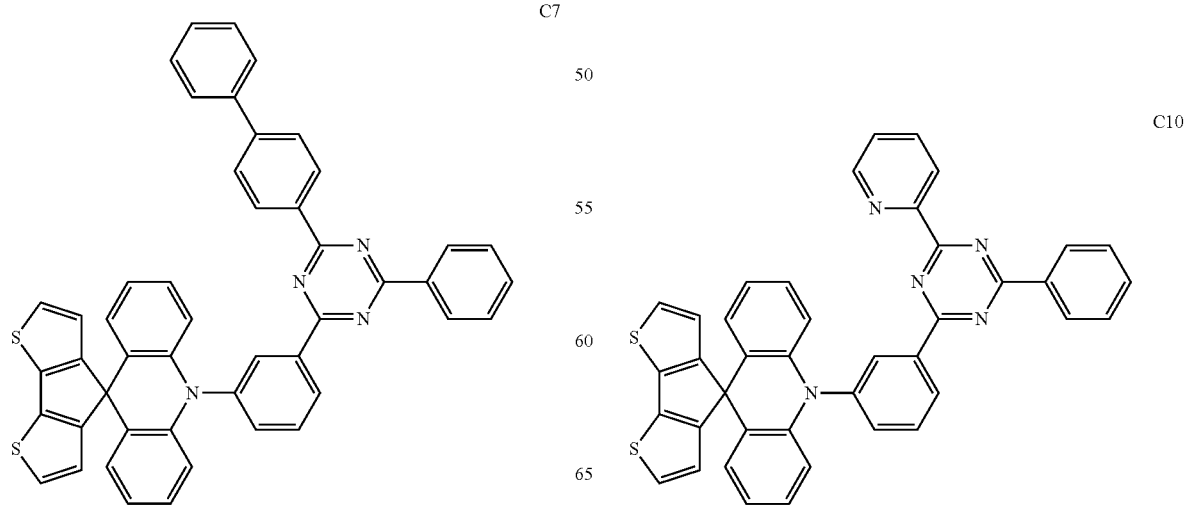
C7
C10

C11
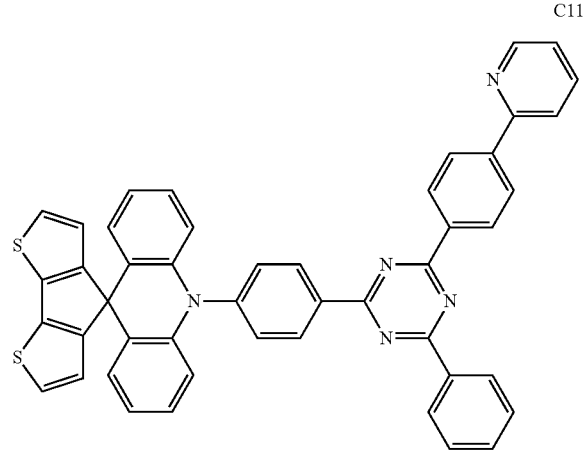
C12
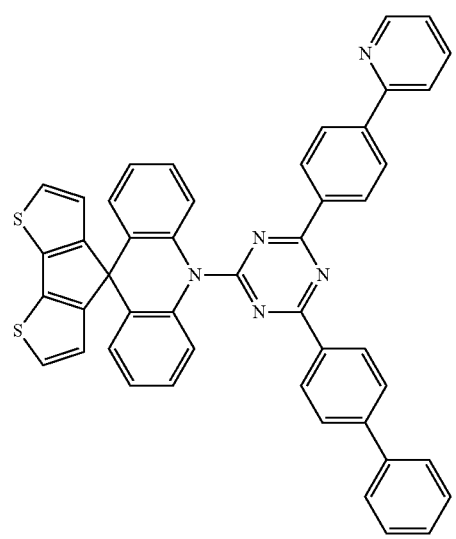
C13
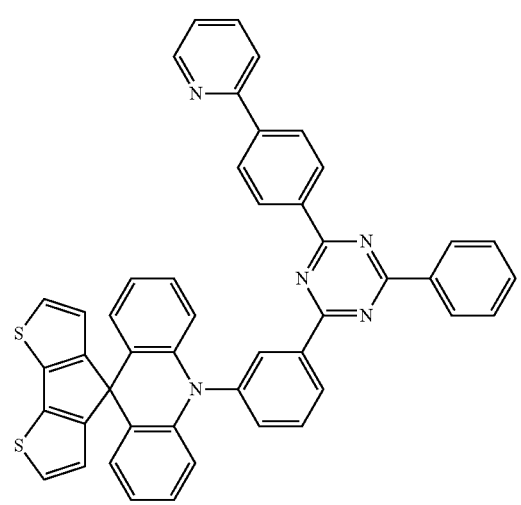
C14
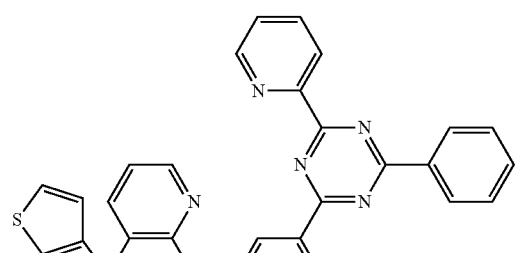
C15
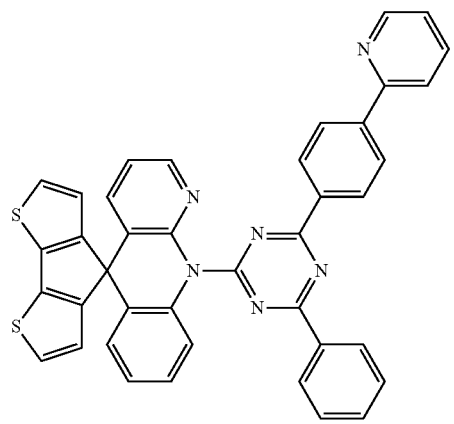
C16
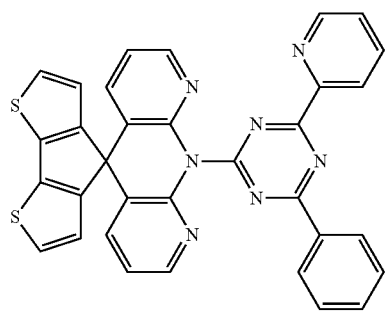
C17
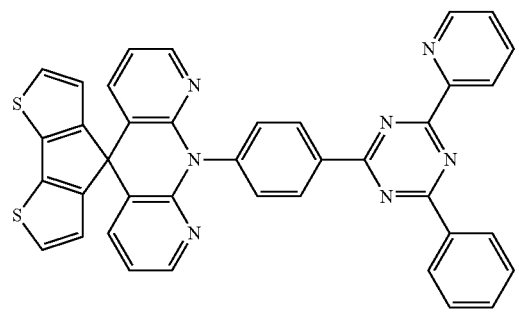

C18
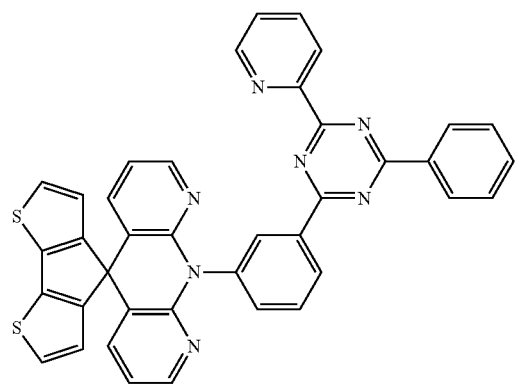
C19
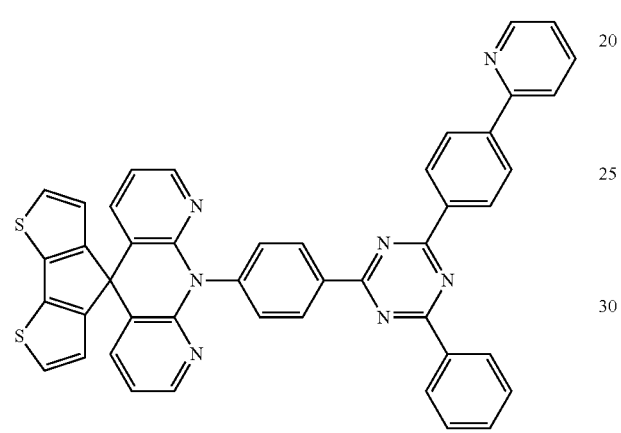
C20
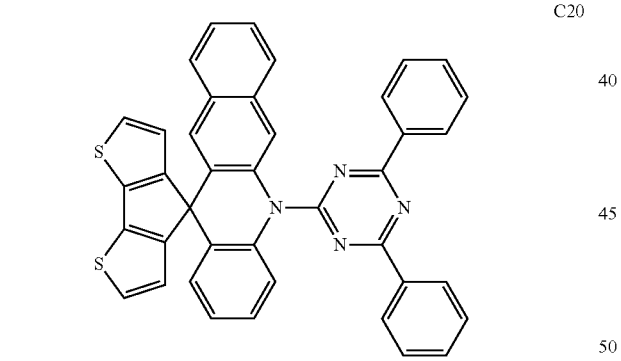
C21
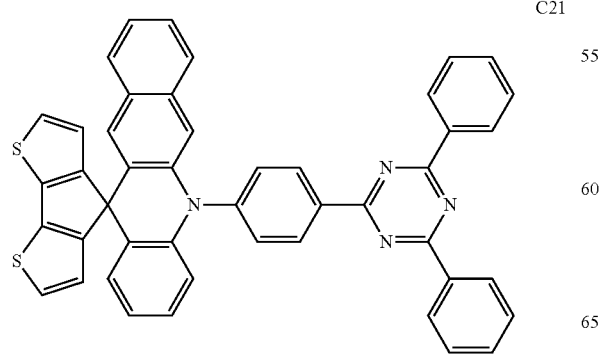
C22
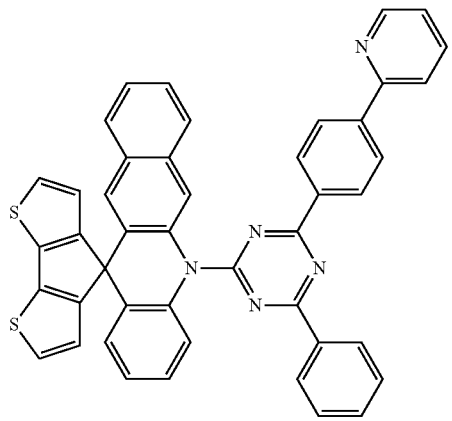
C23
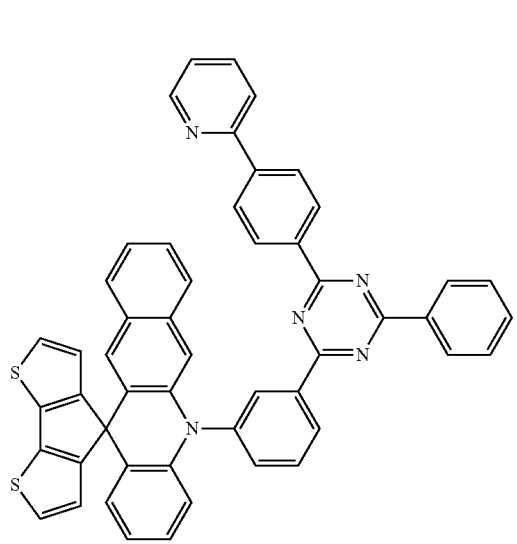
C24
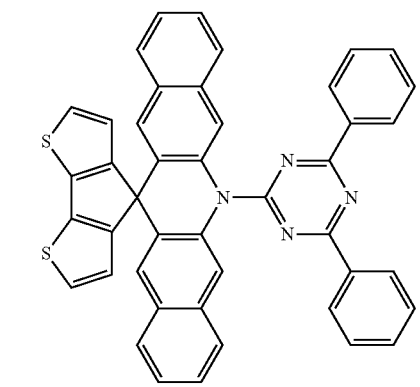

-continued
C25
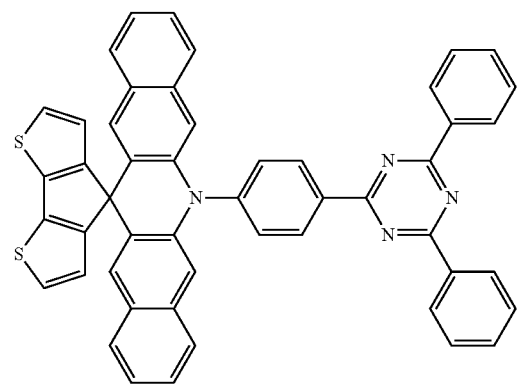
C26
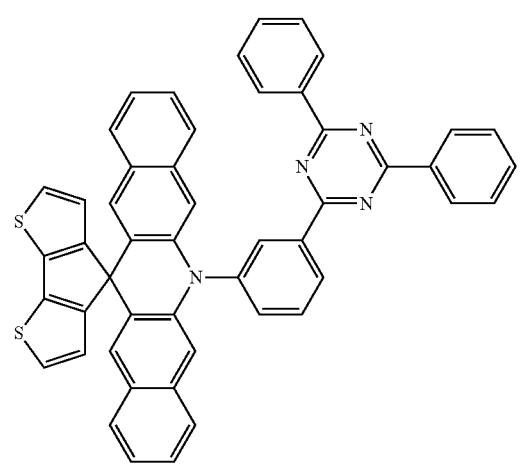
C27
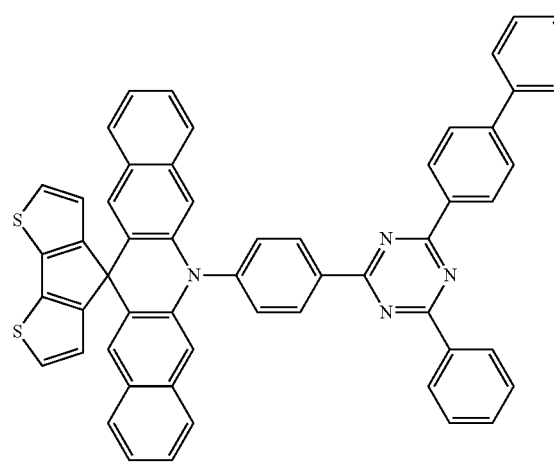
-continued
C28
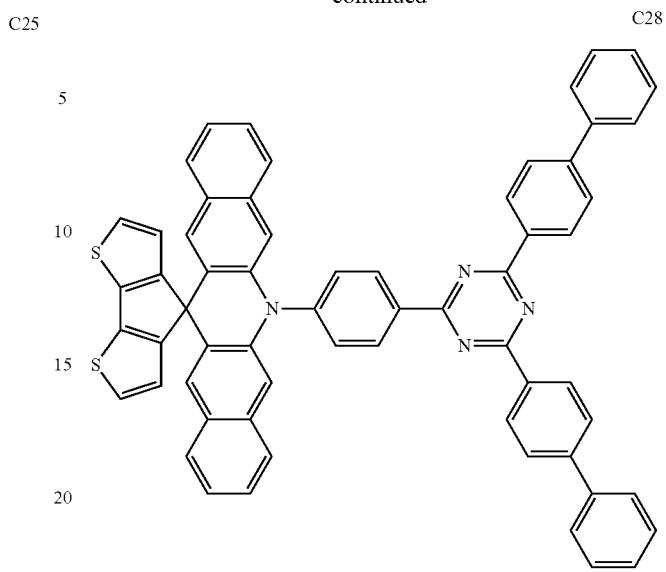
C29
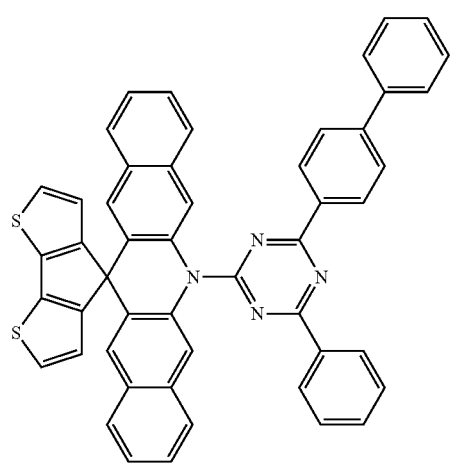
C30
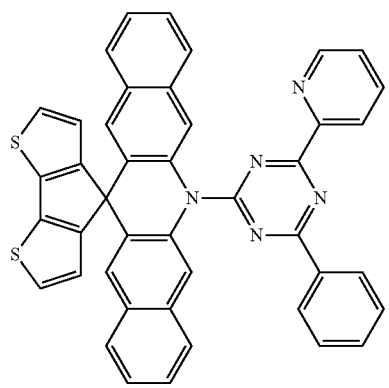

C31
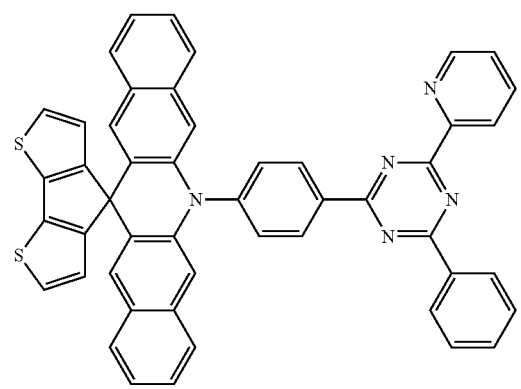
C32
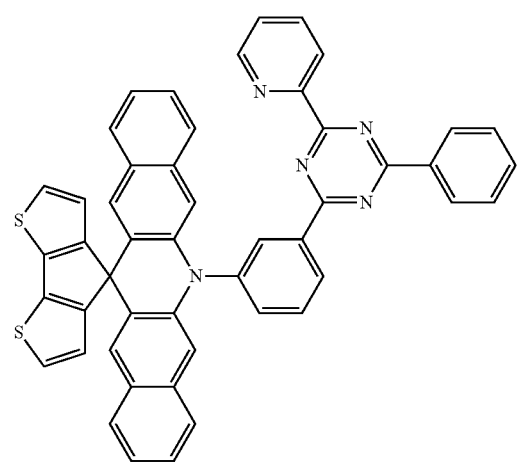
C33
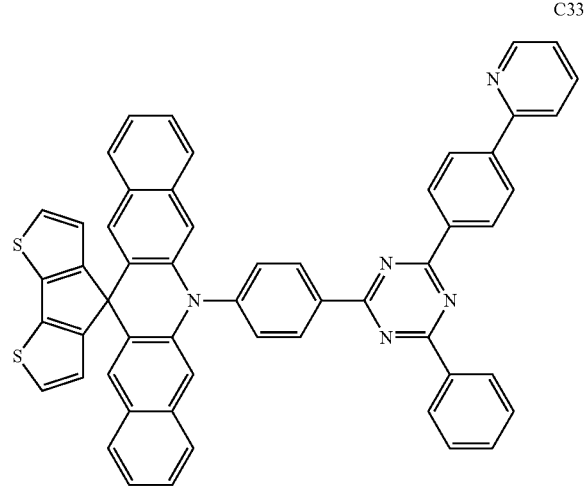
C34
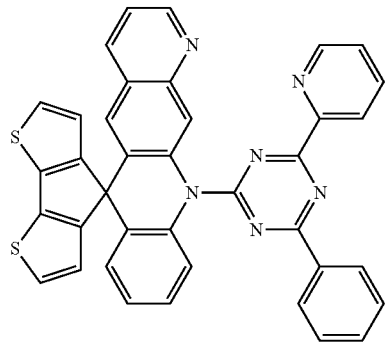
C35
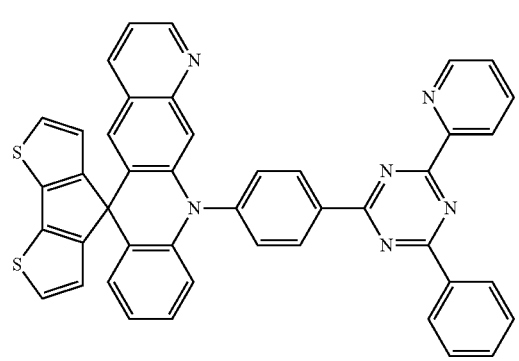
C36
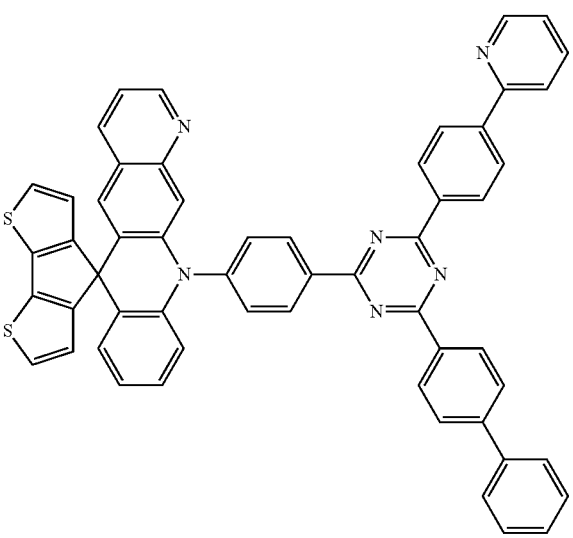

C37
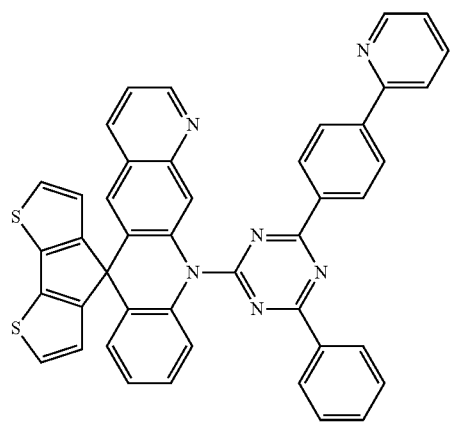
C38
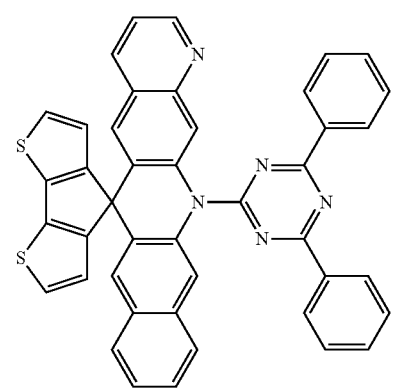
C39
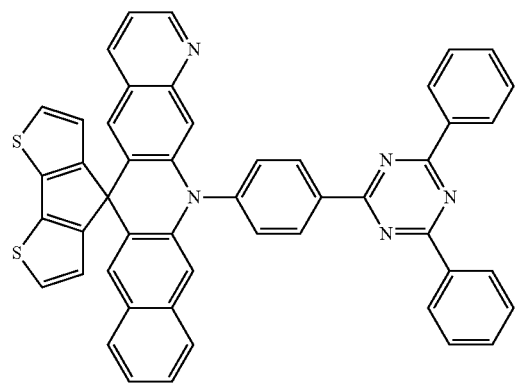
C40
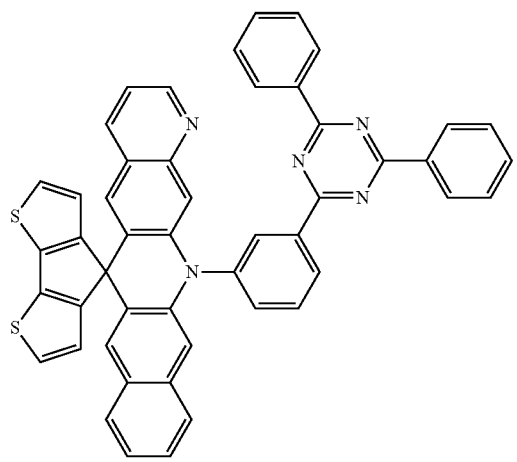
C41
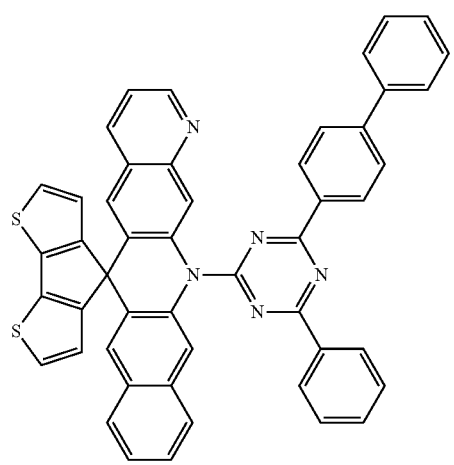
C42
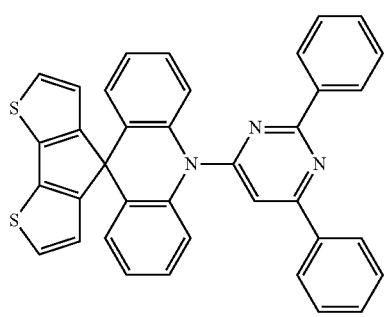
C43
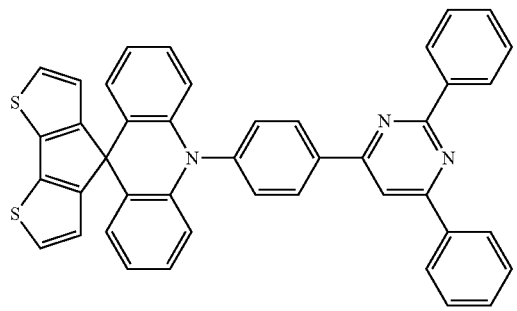

C44
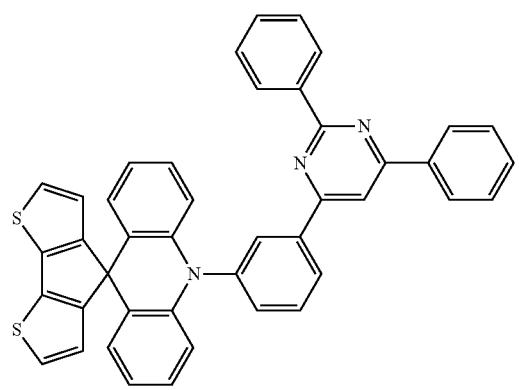
C47
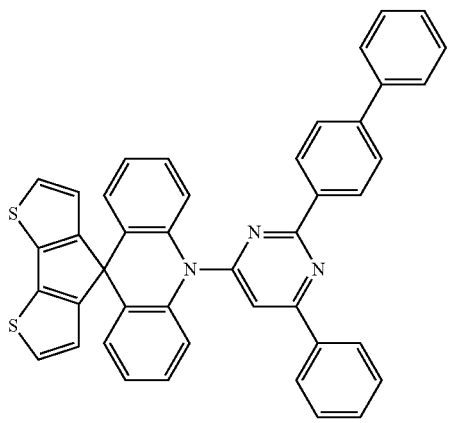
C45
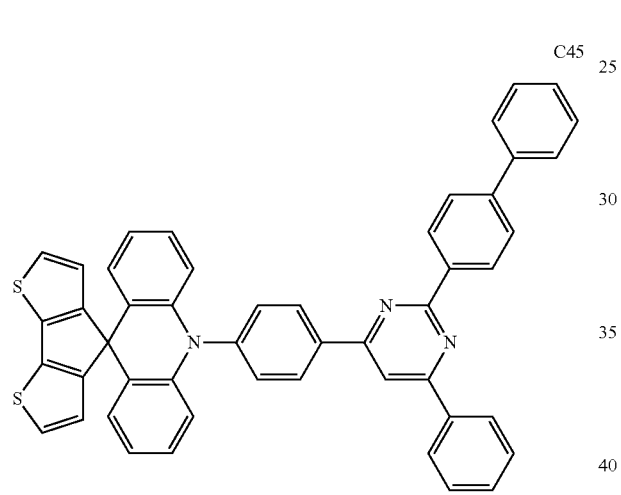
C48
C46
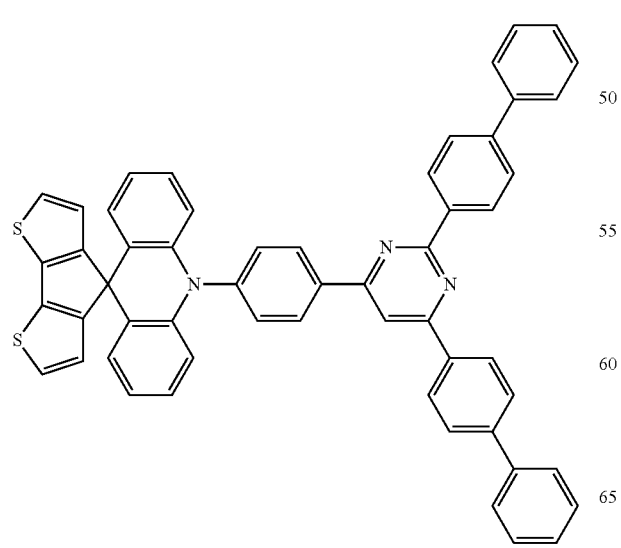
C49
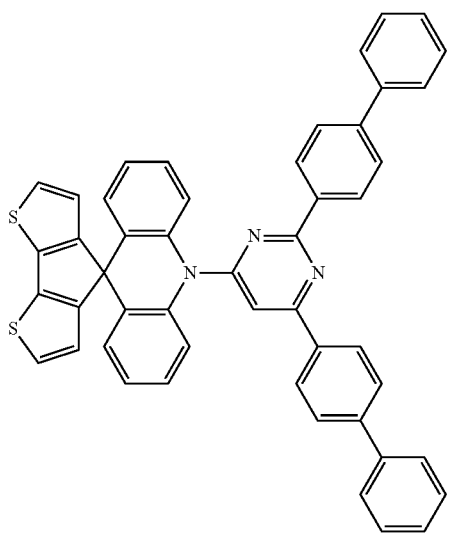

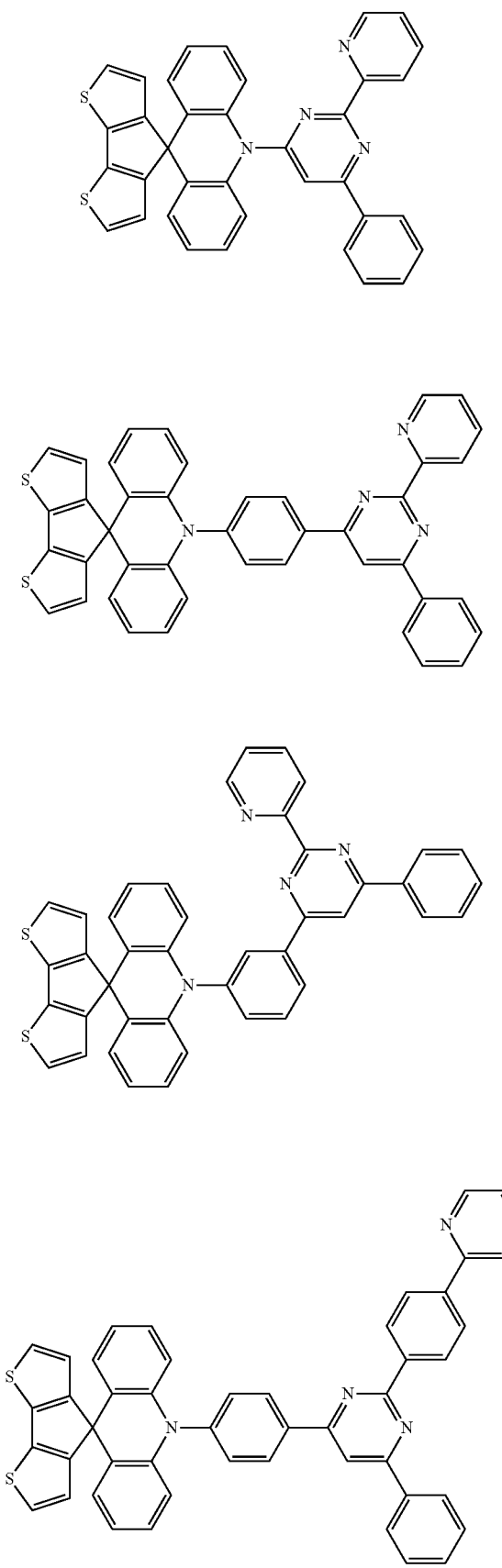
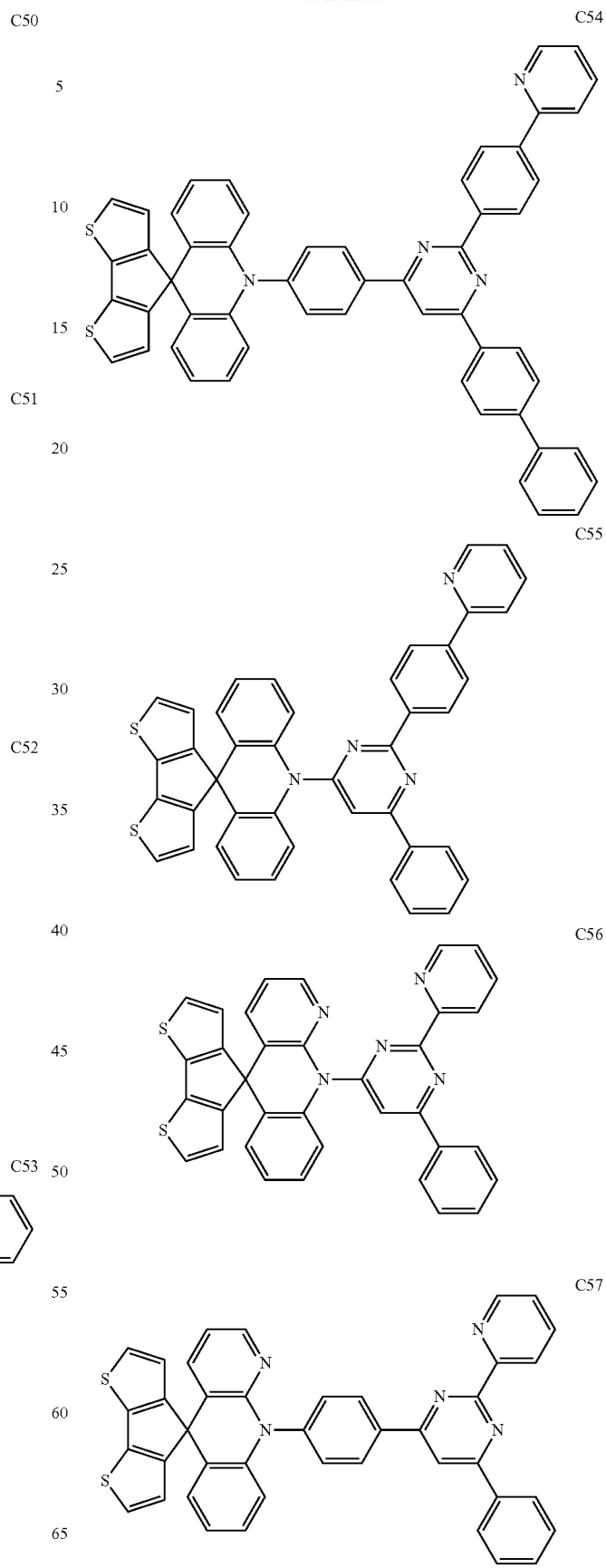

C58
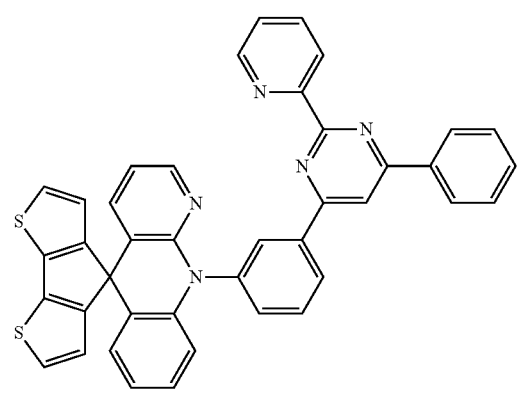
C59
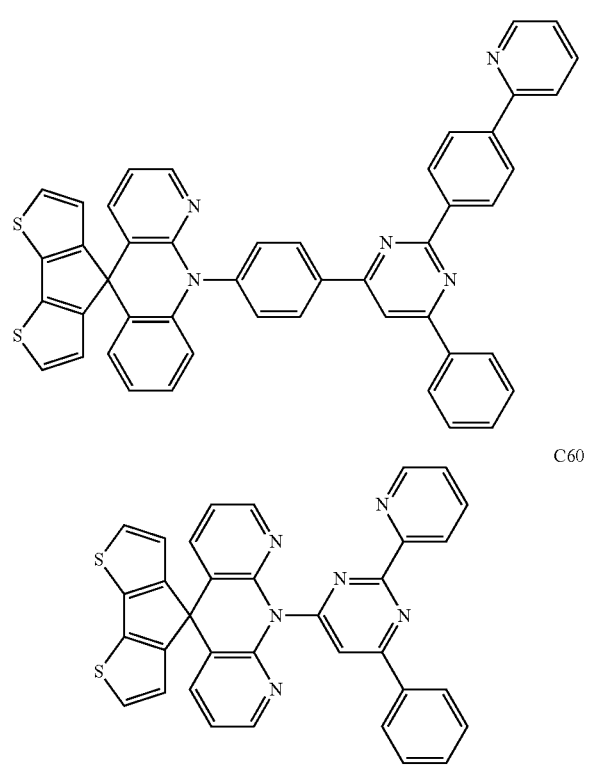
C60
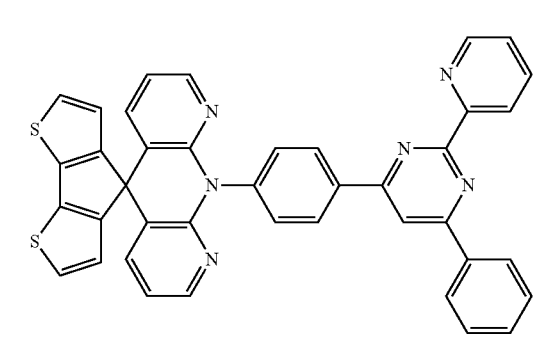
C61
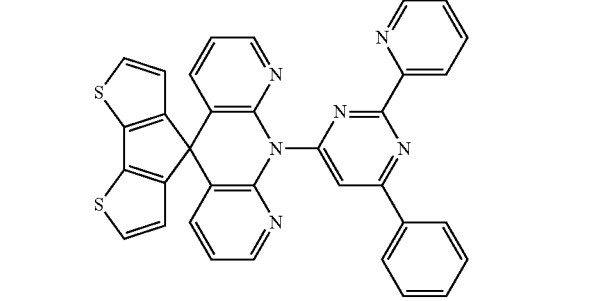
C62
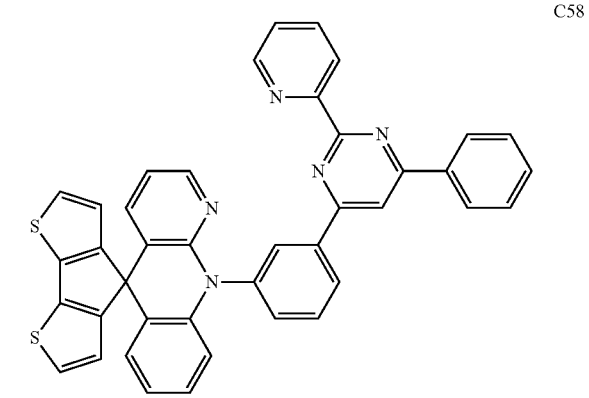
C63
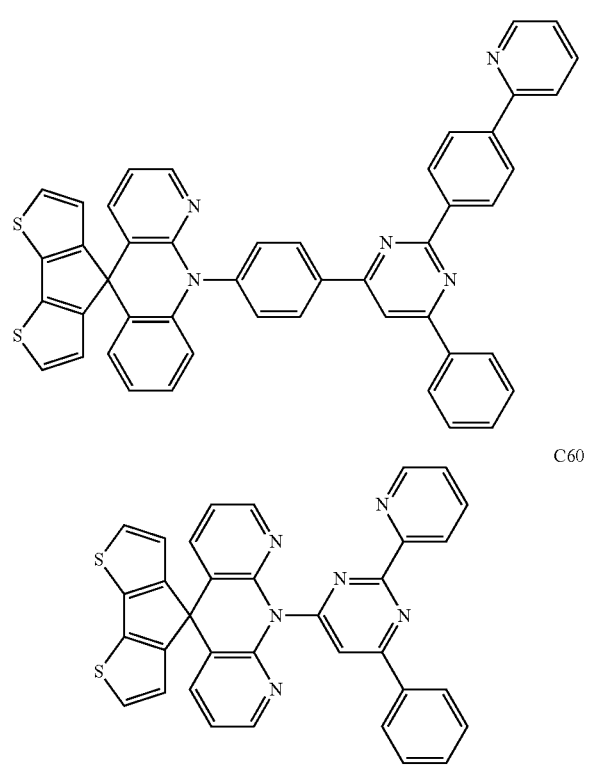
C64
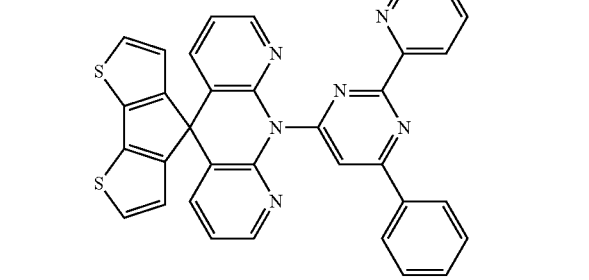

-continued
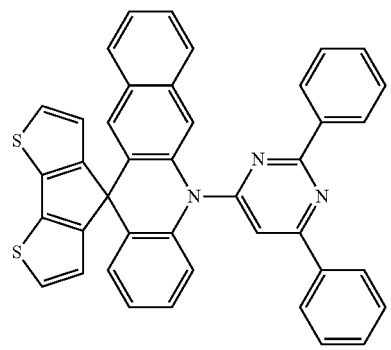
C65
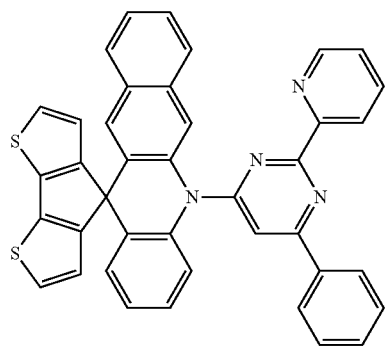
C69
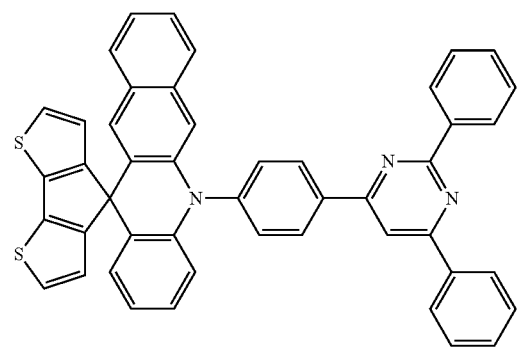
C66
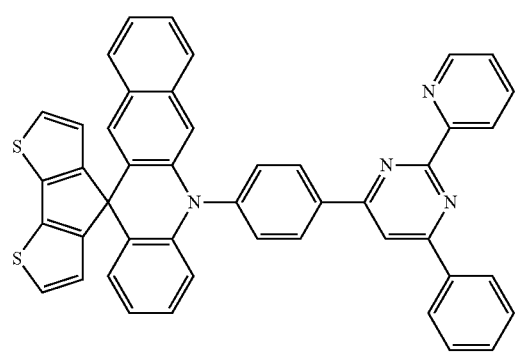
C70
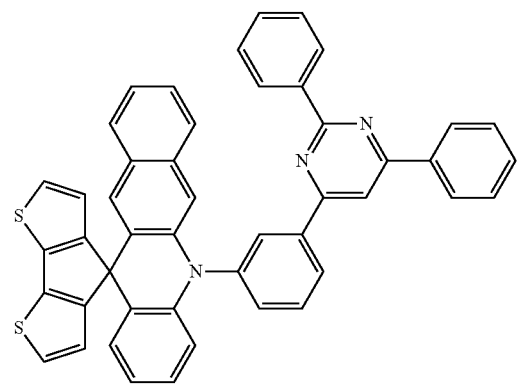
C67
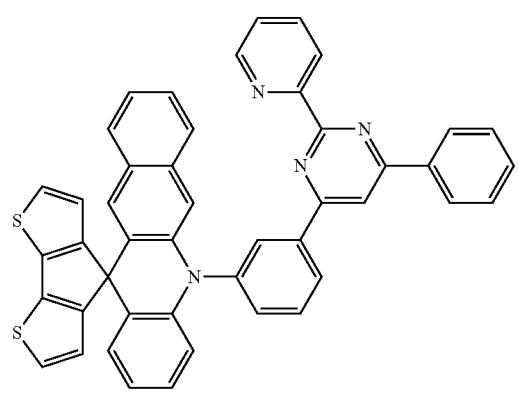
C71
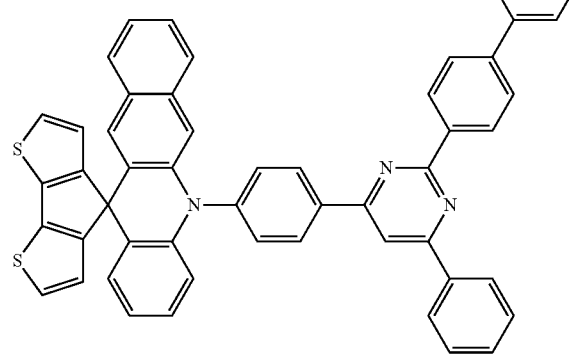
C68
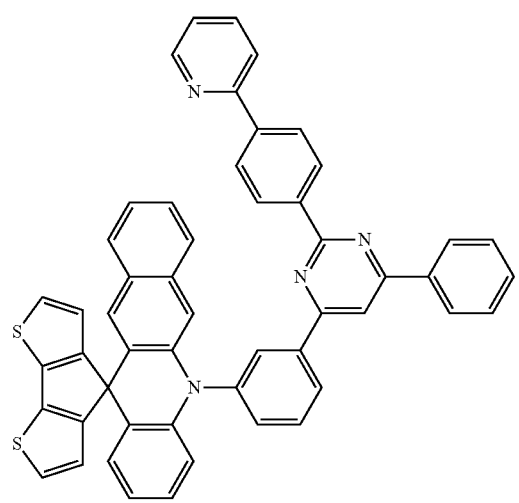
C72

C73
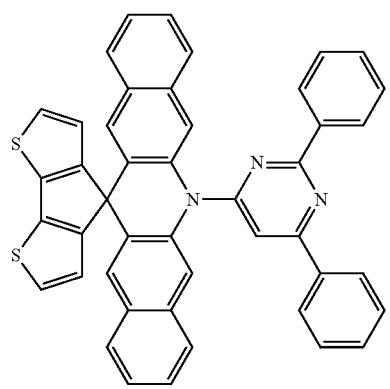
C74
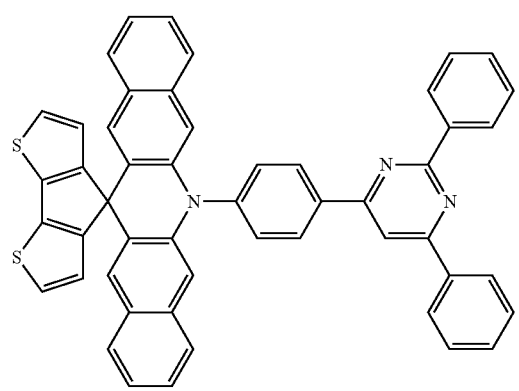
C75
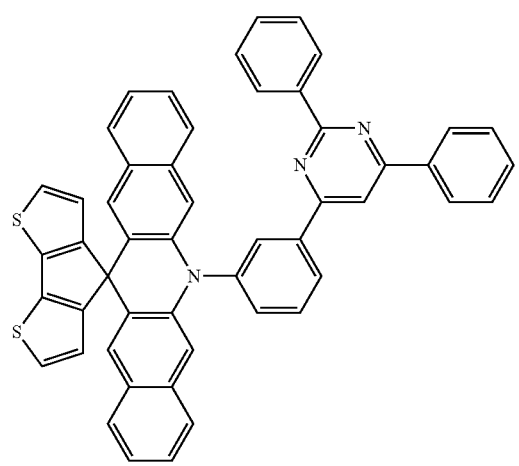
C76
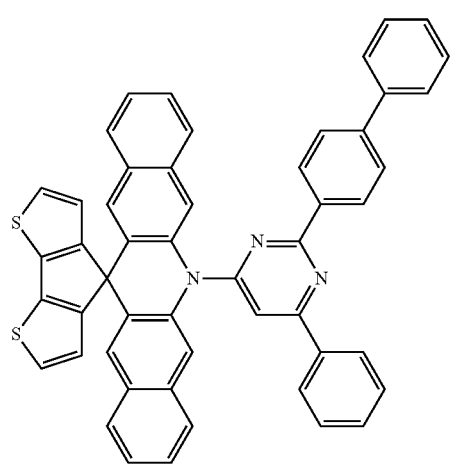
C77
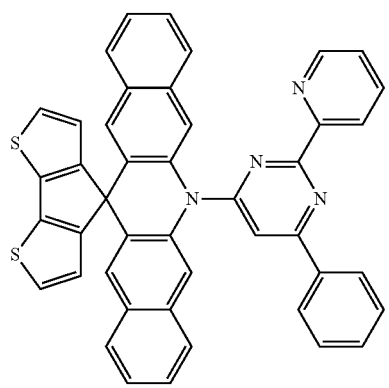
C78
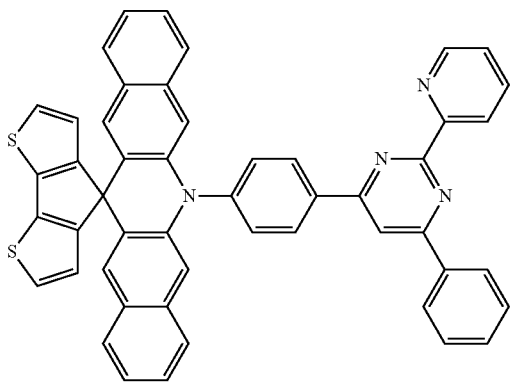

-continued
C79
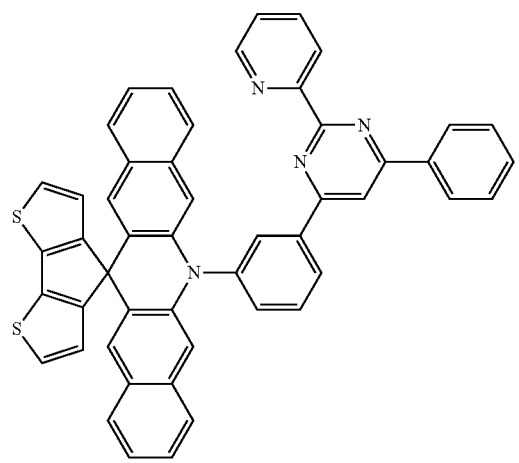
C80
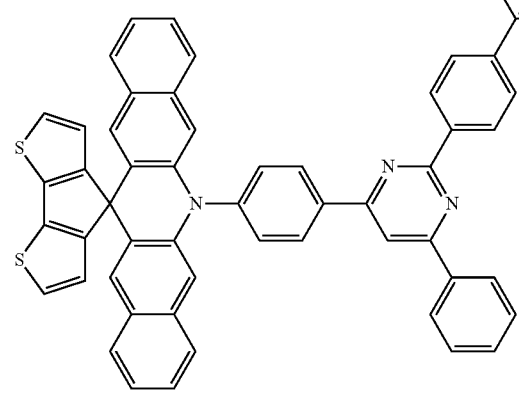
C81
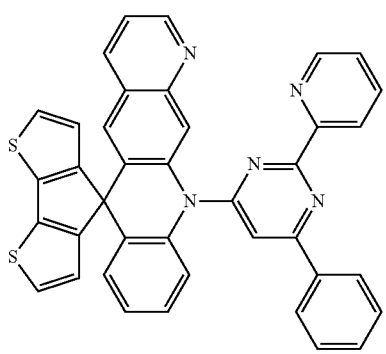
C82
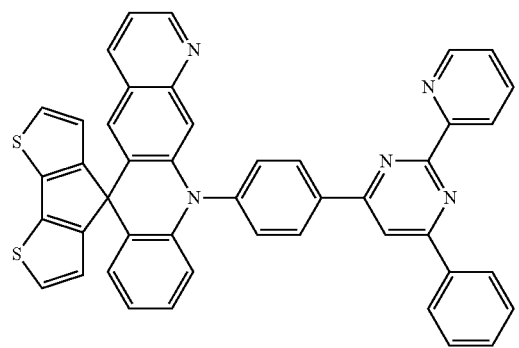
-continued
C83
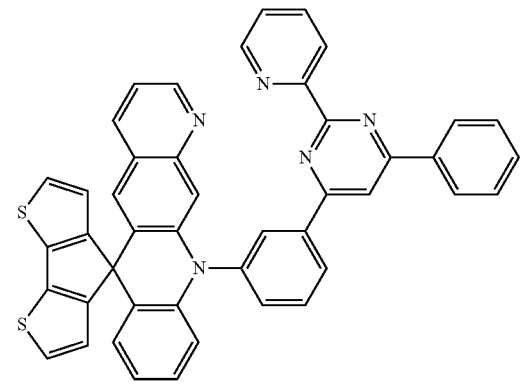
C84
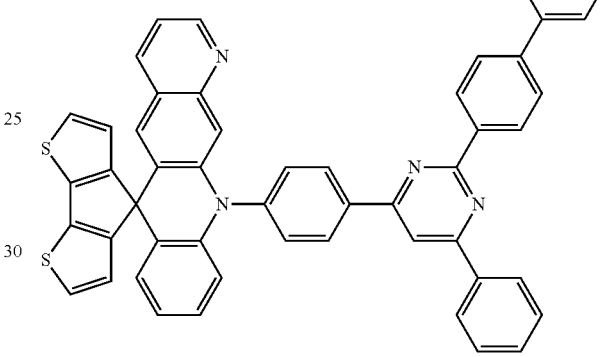
C85
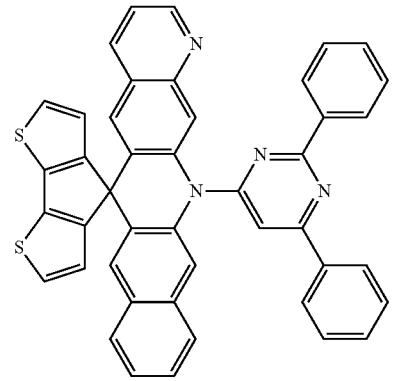
C86
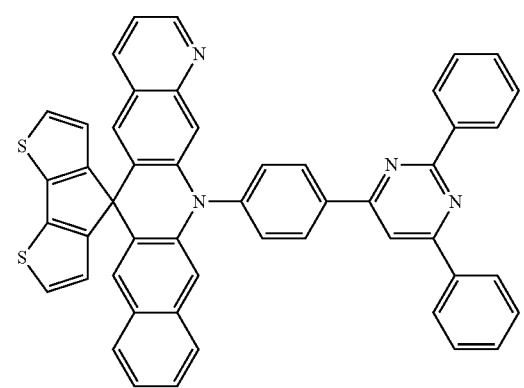

-continued
C87
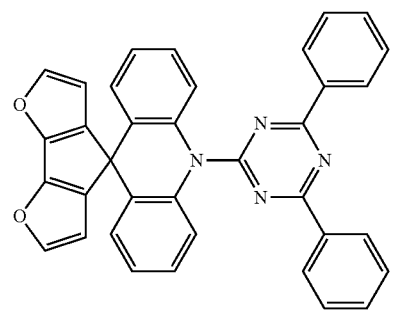
C88
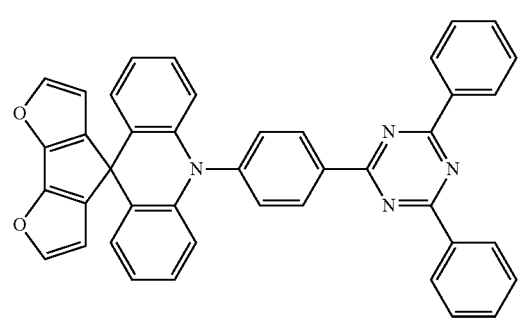
C89
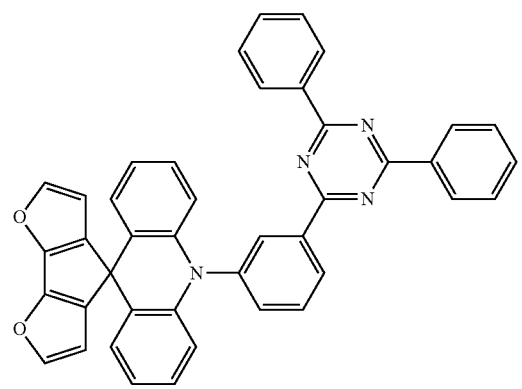
C90
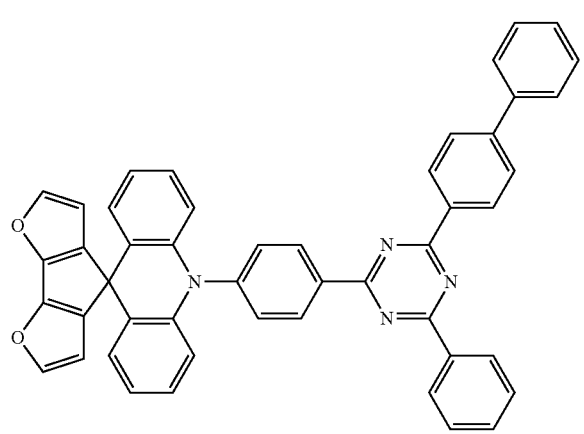
-continued
C91
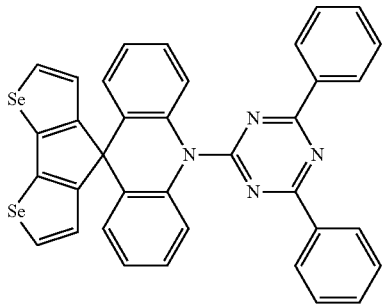
C92
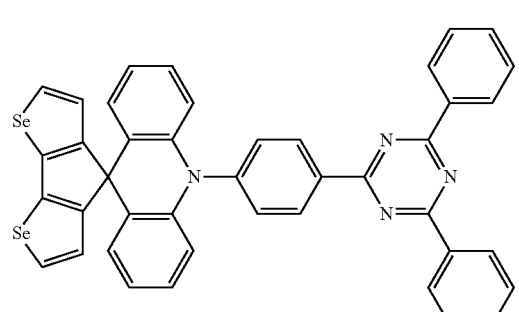
C93
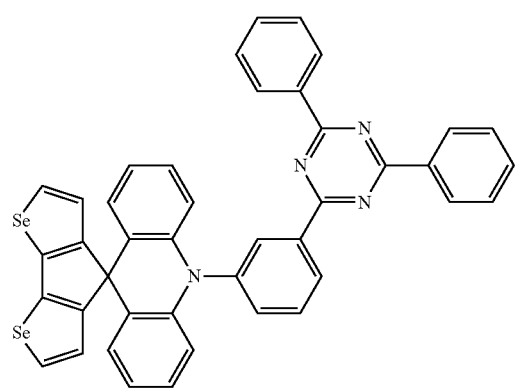
C94
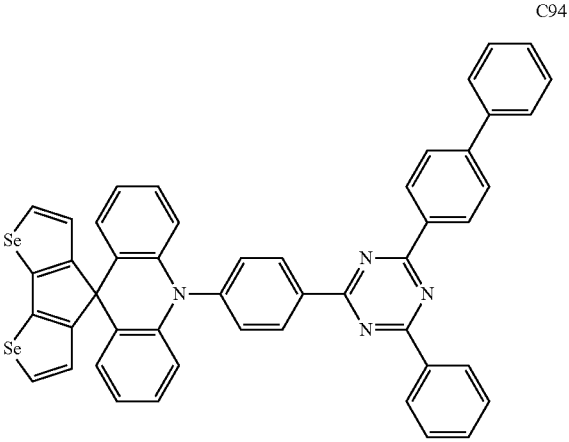

C95 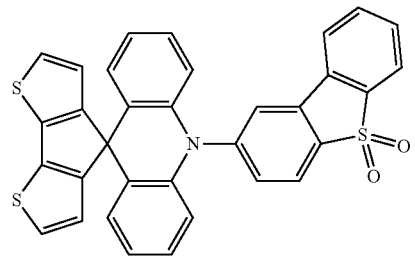
C96 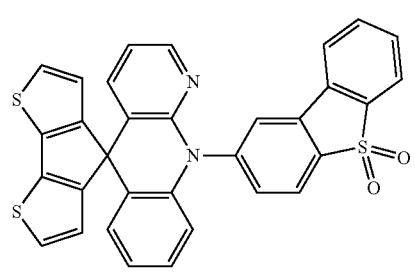
C97 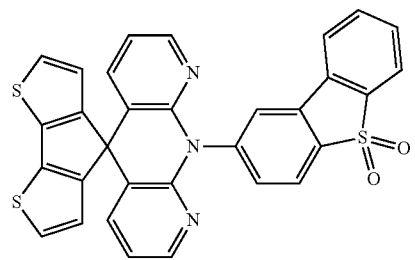
C98 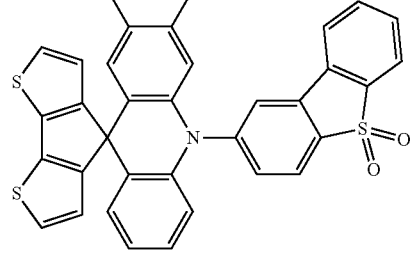
C99 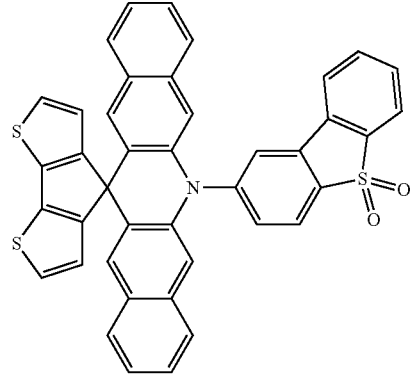
C100 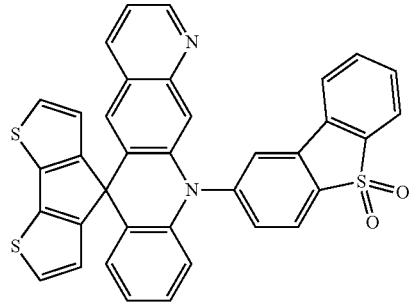
C101 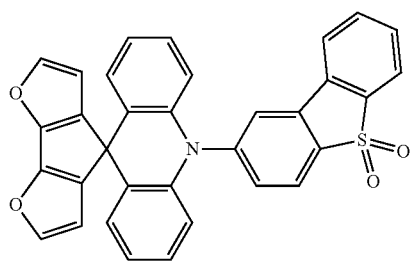
C102 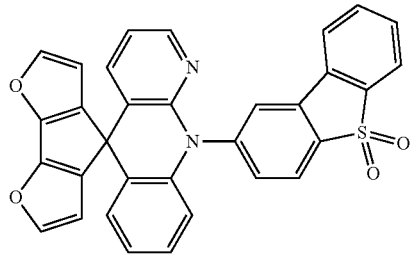
C103 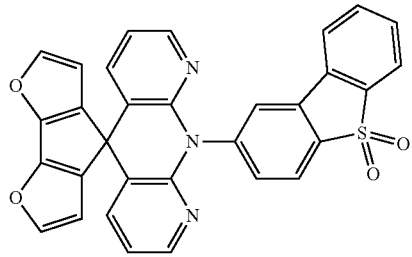
C104 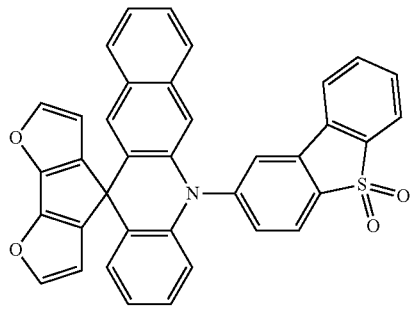

C105
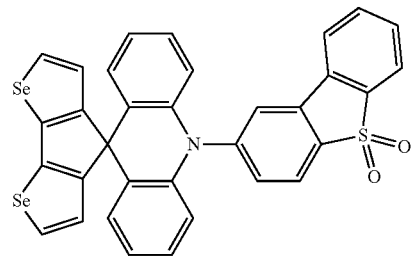
C106
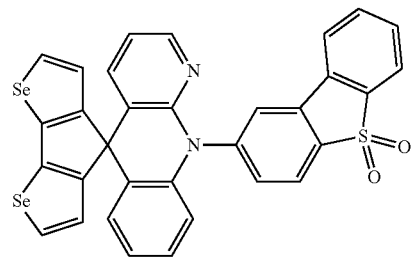
C107
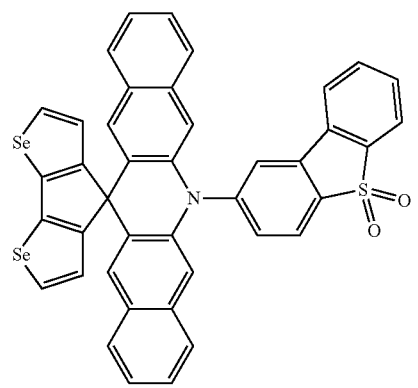
C108
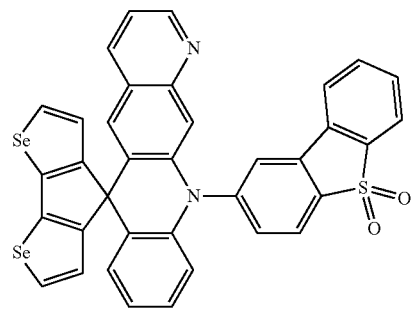
C109
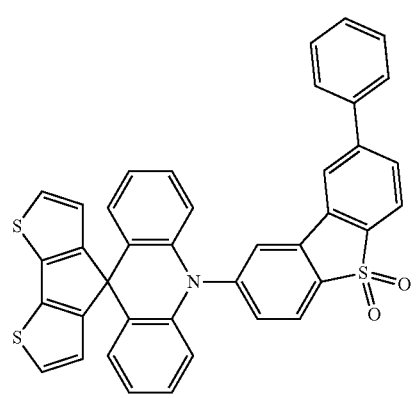
C110
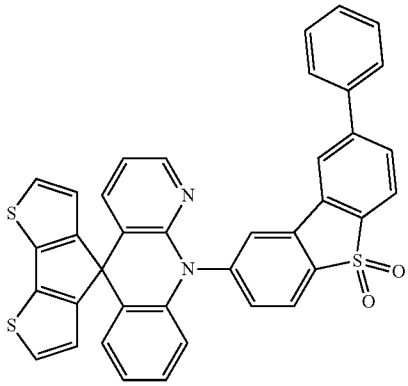
C111
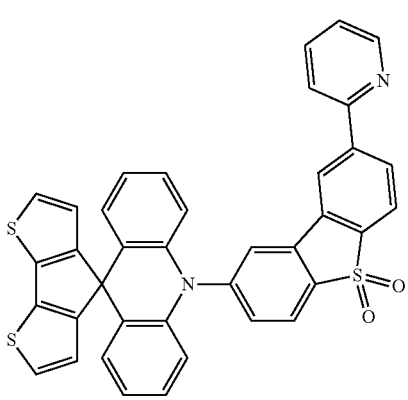
C112
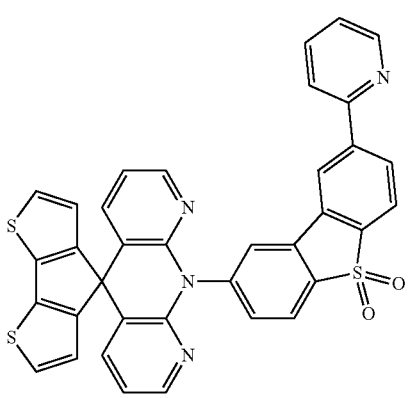
C113
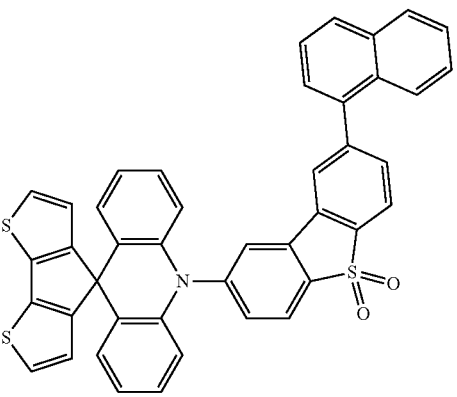

C114
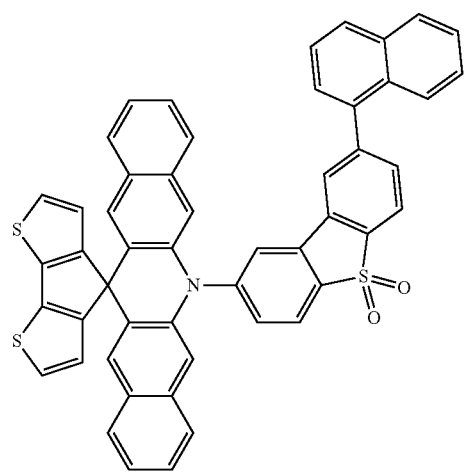
C115
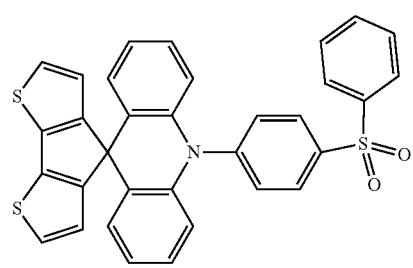
C116
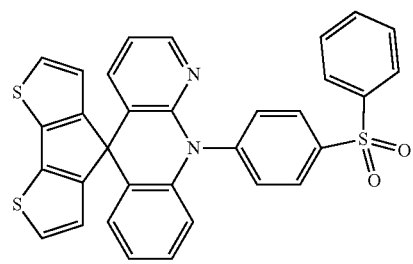
C117
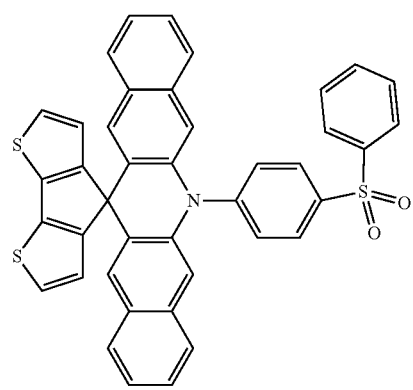
C118
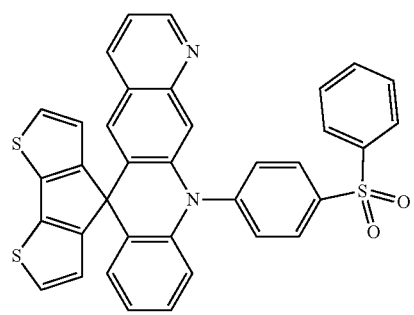
C119
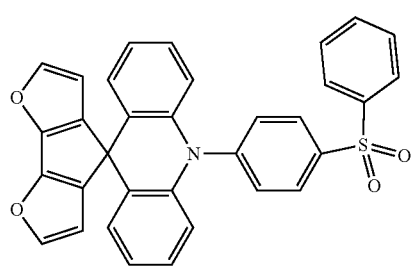
C120
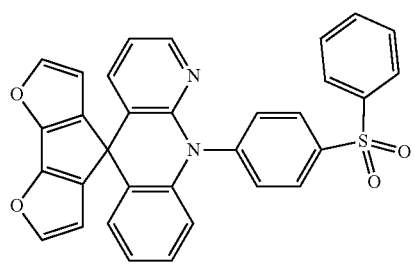
C121
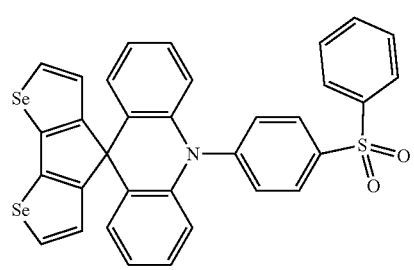
C122
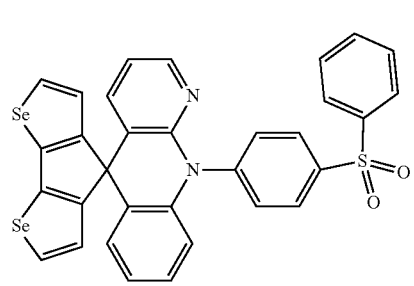

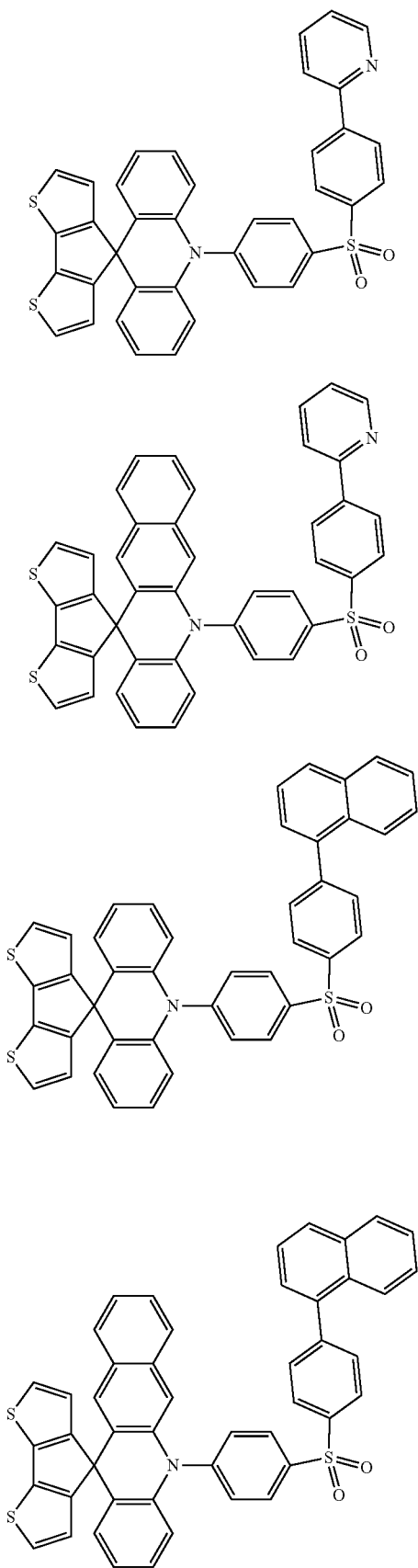
C123
C124
C125
C126
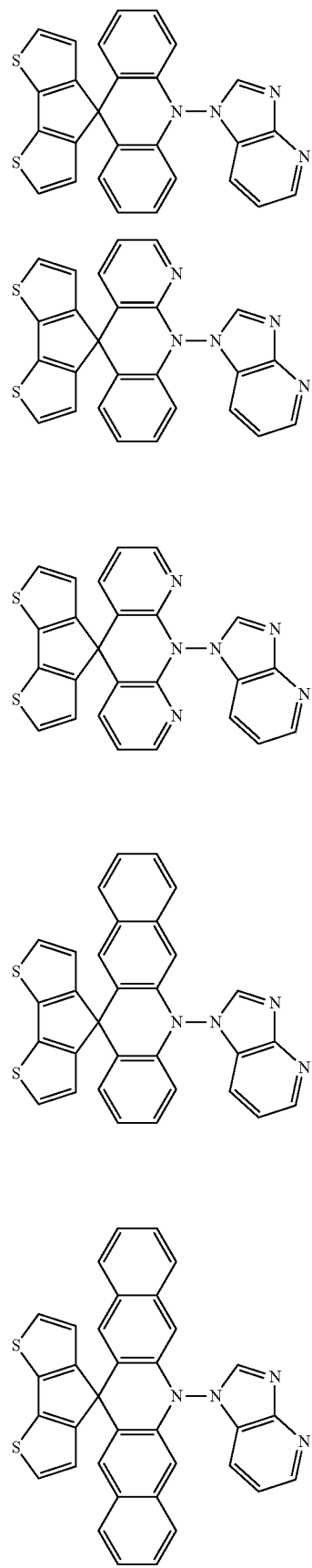
C127
C128
C129
C130
C131

C132 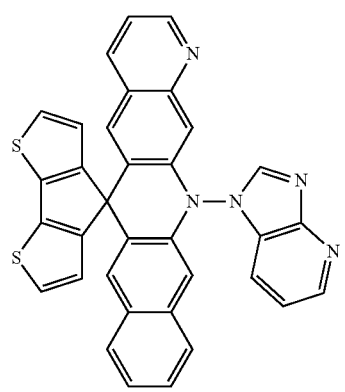
C137 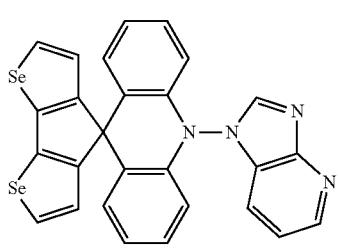
C133 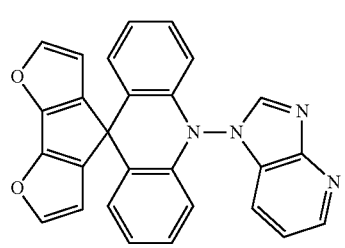
C138 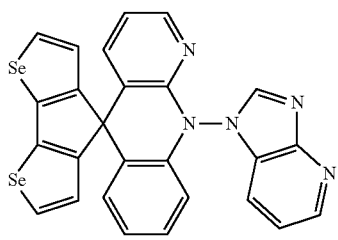
C134 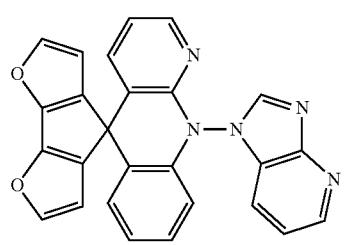
C135 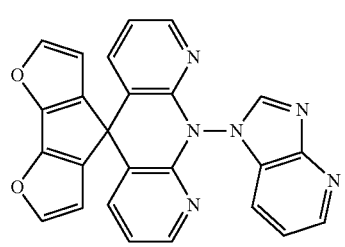
C139 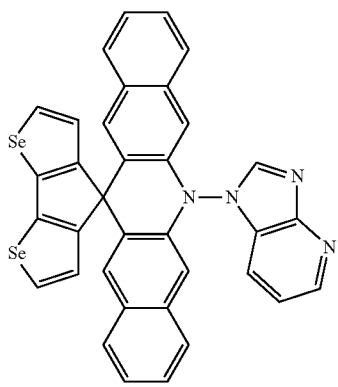
C136 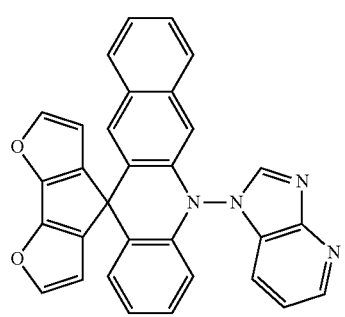
C140 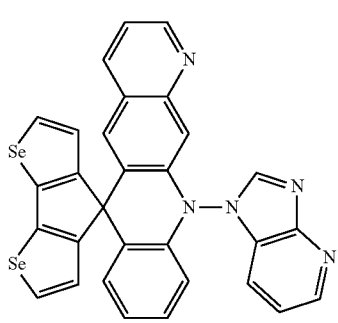

C141
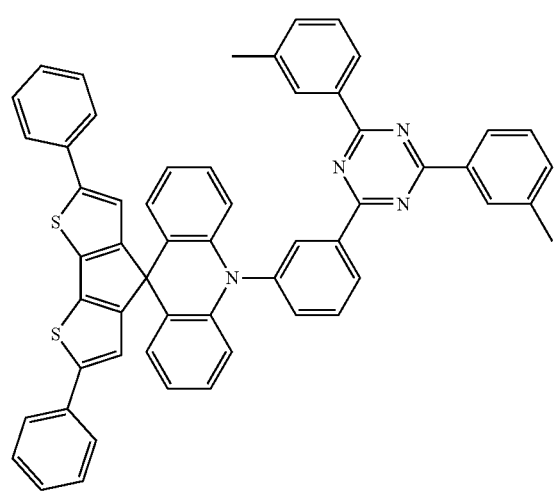
C144
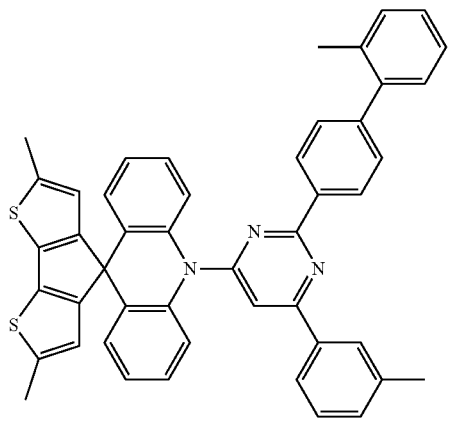
C142
C145
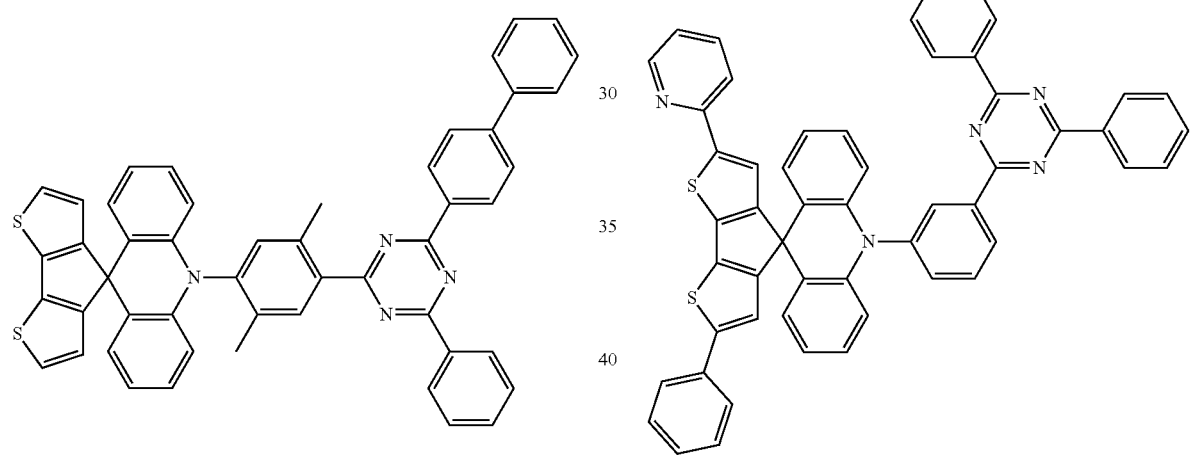
C143
C146
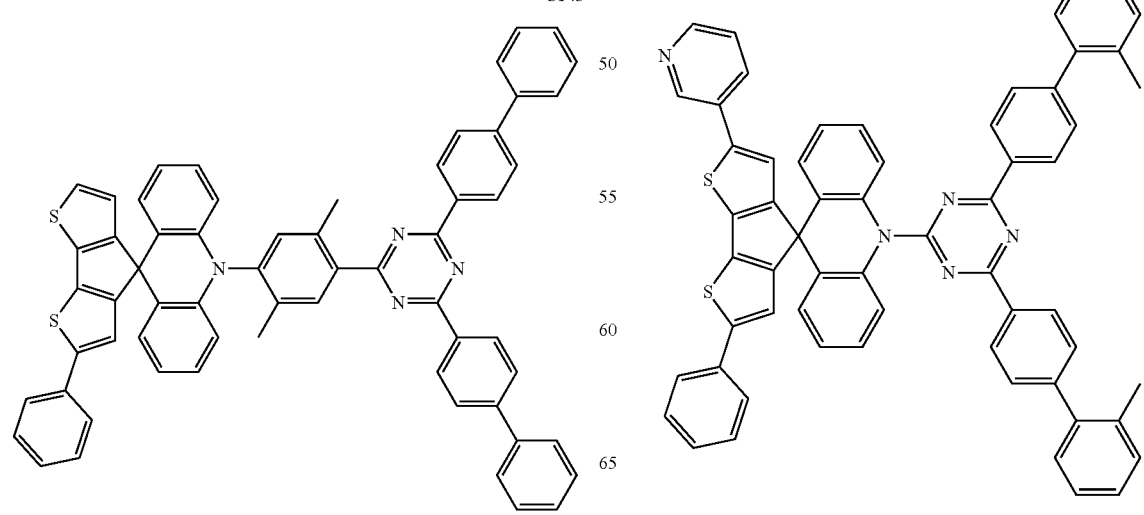

C147
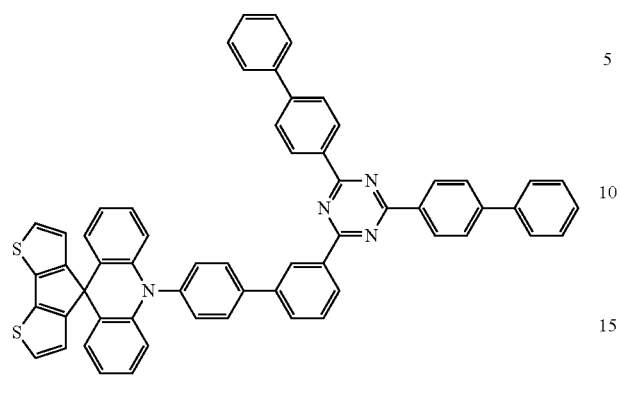
C148
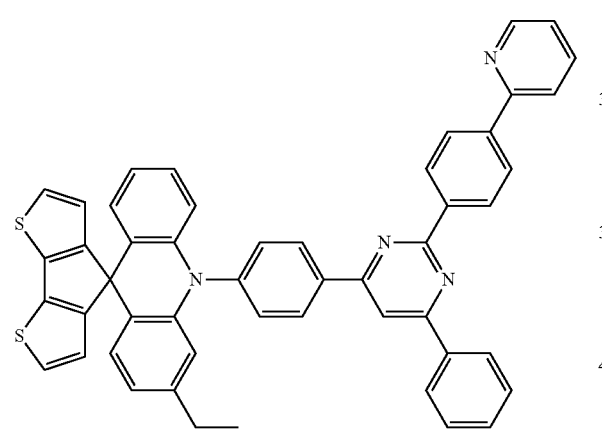
C149
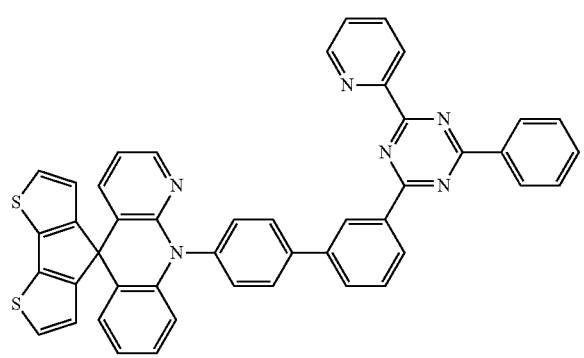
C150
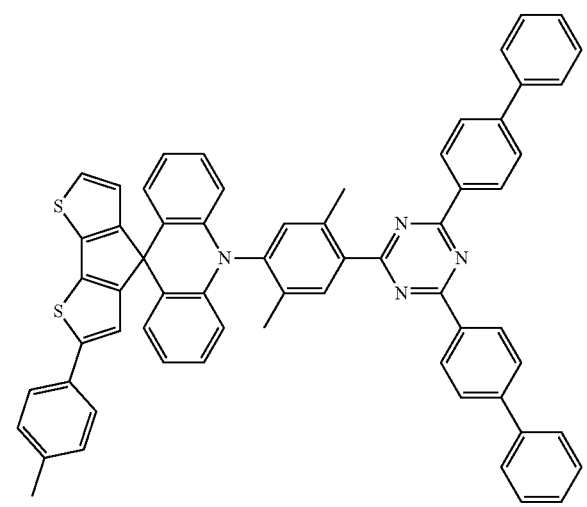
C151
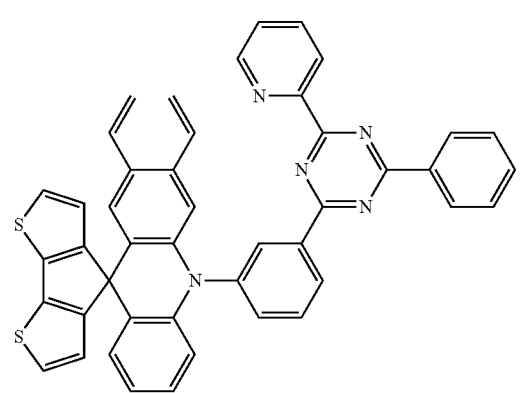
C152
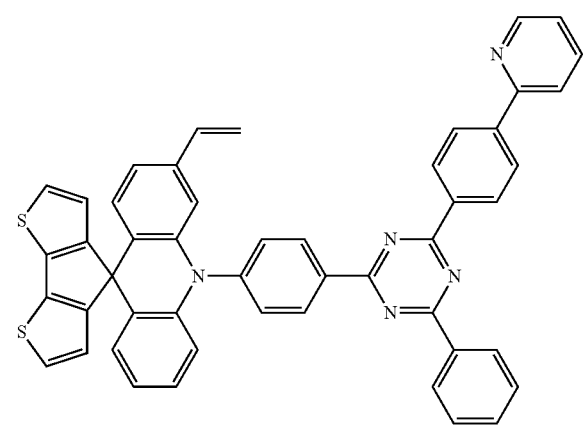

C153
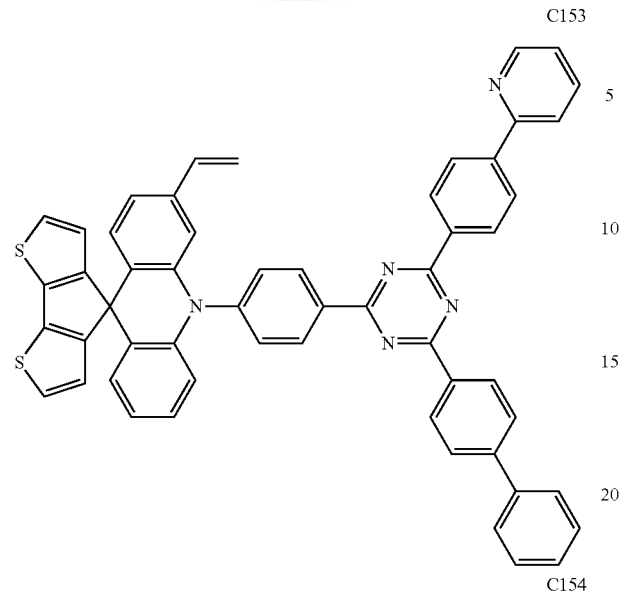
C154
C155
C156
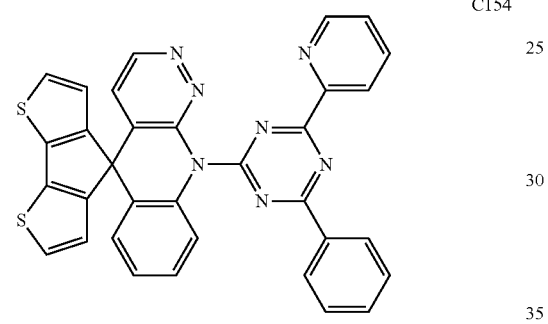
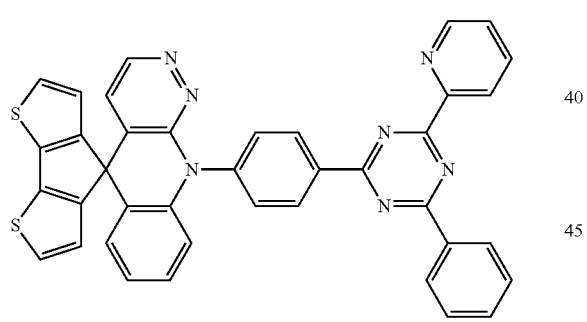
C157
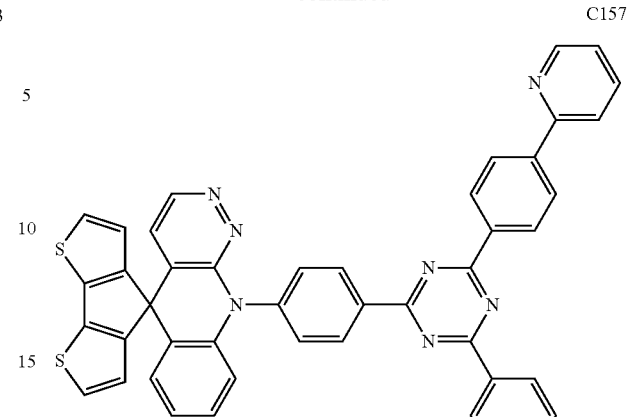
C158
C159
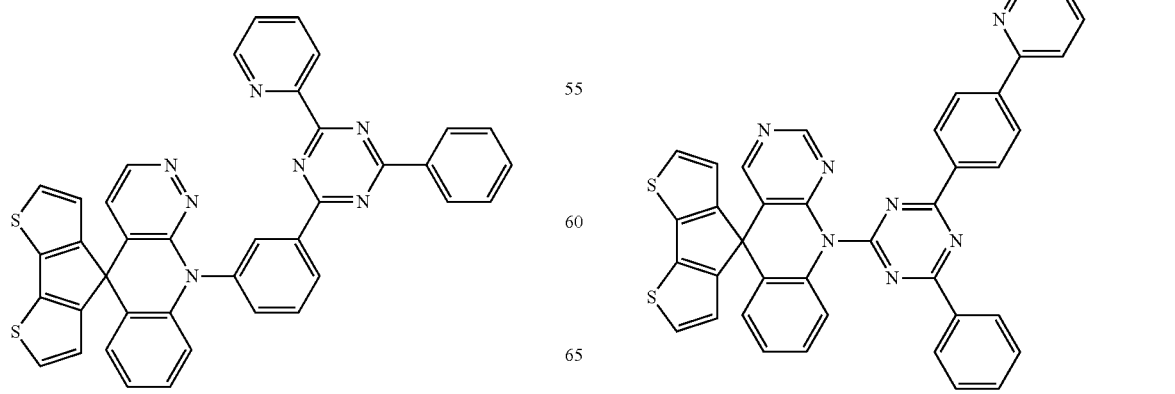

C160
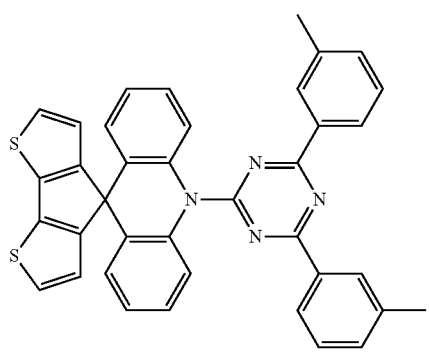
C161
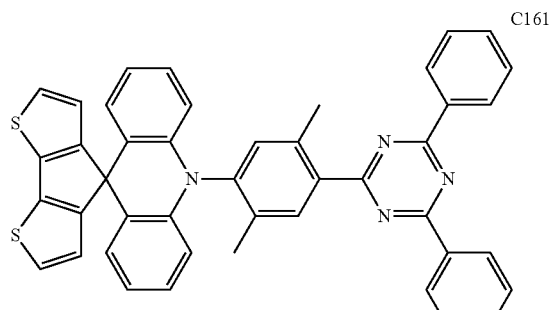
In another embodiment of the present invention, the delayed fluorescence compound may be represented by the following formula (8):
formula (8)
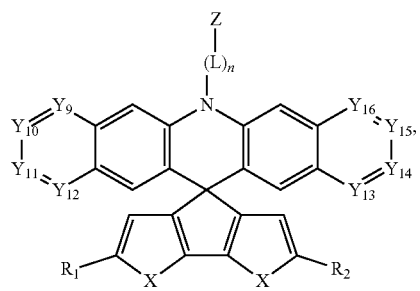
wherein $Y_9$-$Y_{16}$ are each independently a nitrogen atom or CR; and R, $R_1$, $R_2$, X, L, n, and Z have the same meaning as defined above.
Preferably, the delayed fluorescence compound of formula (8) is one of the following compounds:
C24
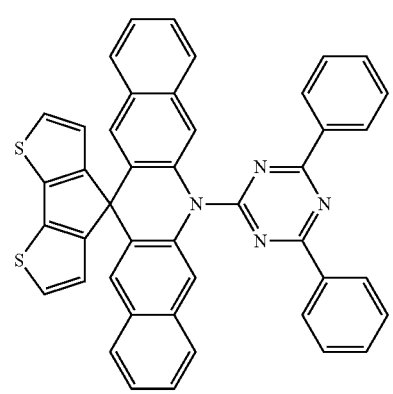
C25
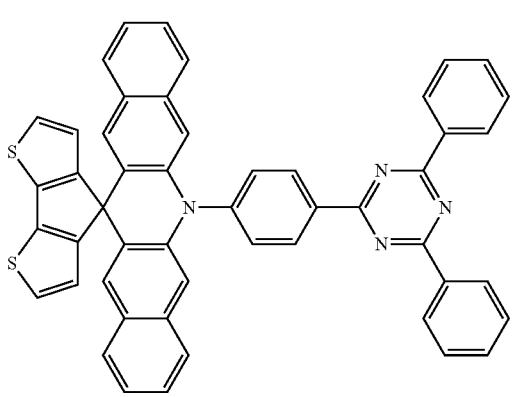
C26
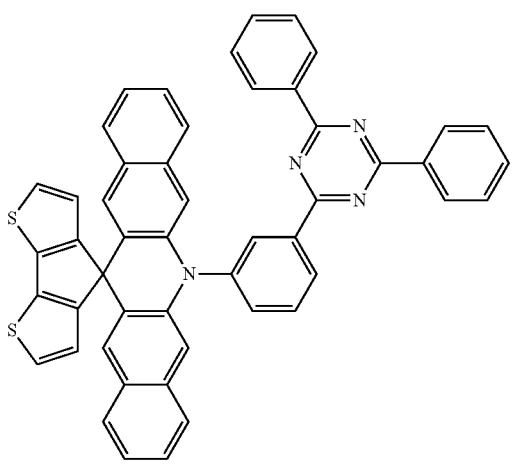

51
-continued
C27
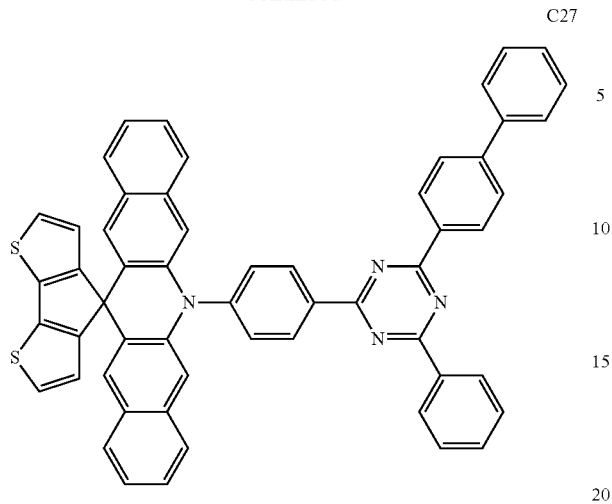
C28
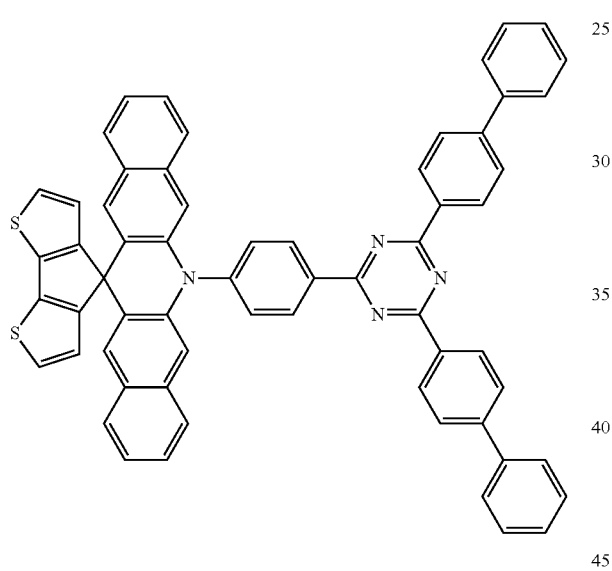
C29
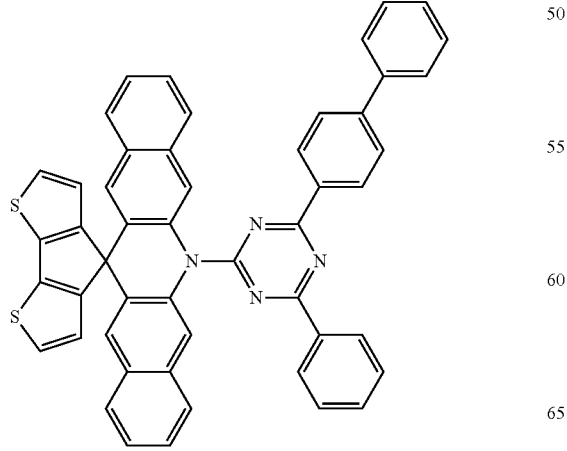
52
-continued
C30
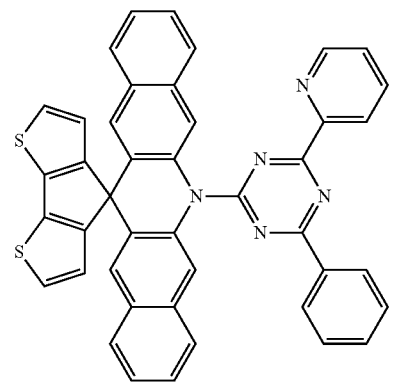
C31
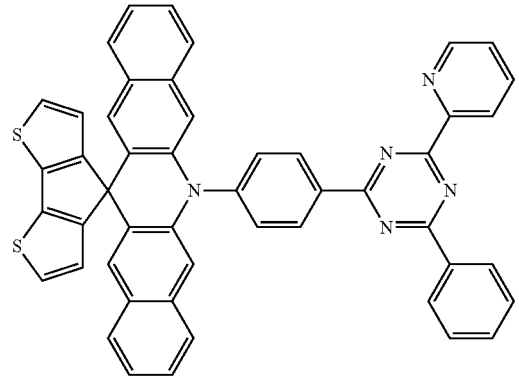
C32
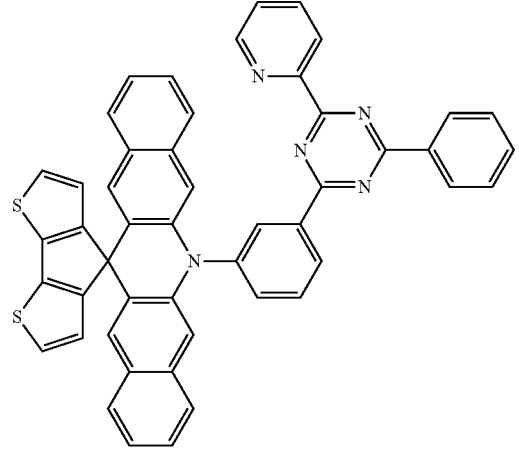

C33
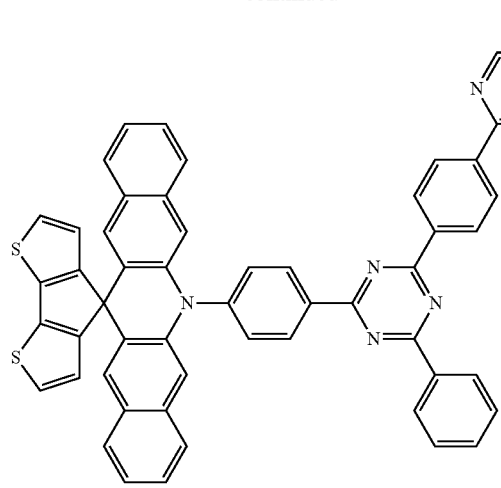
C40
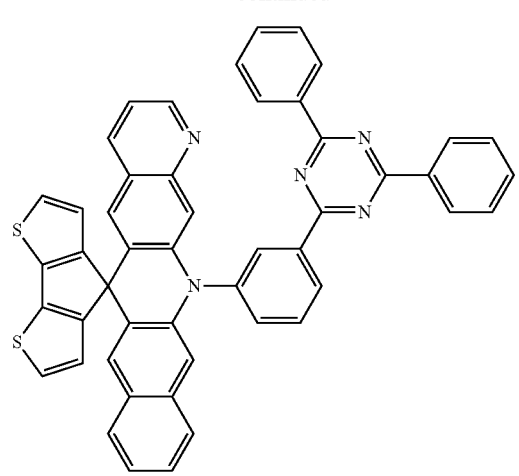
C38
C41
C39
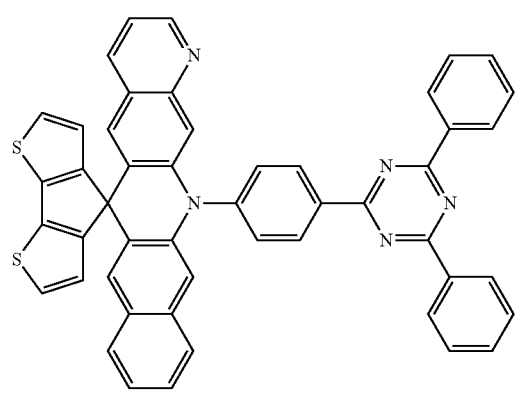
C73
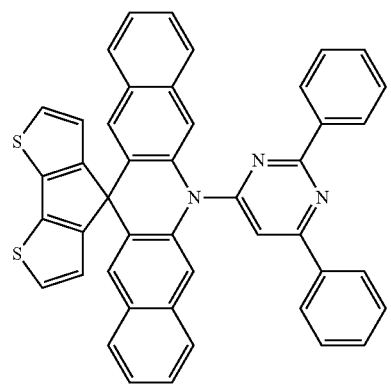

-continued
C74
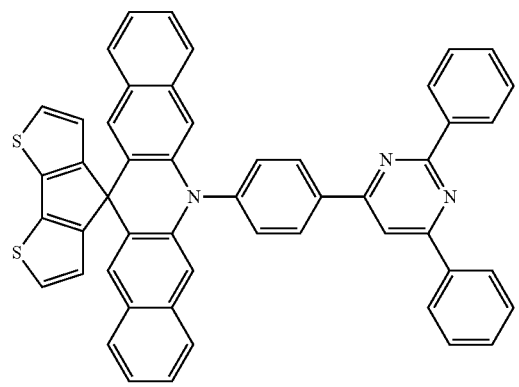
C75
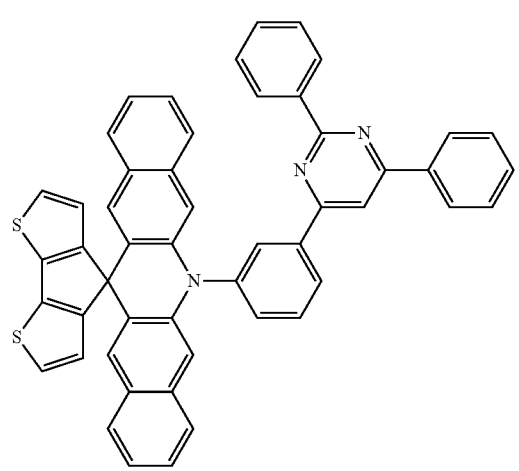
C76
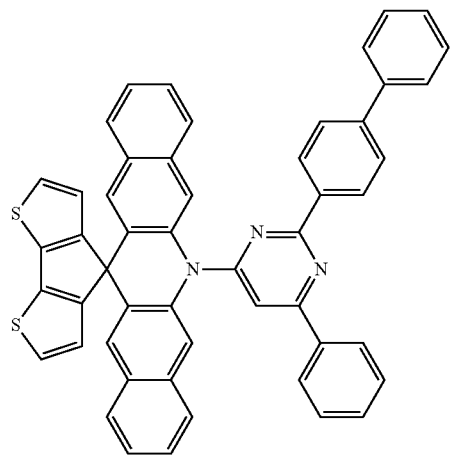
-continued
C77
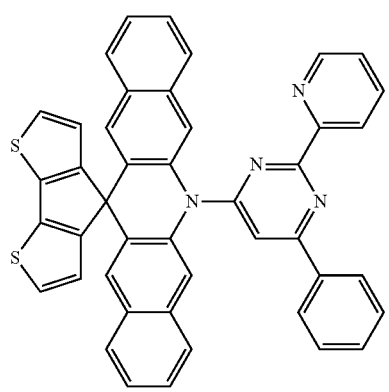
C78
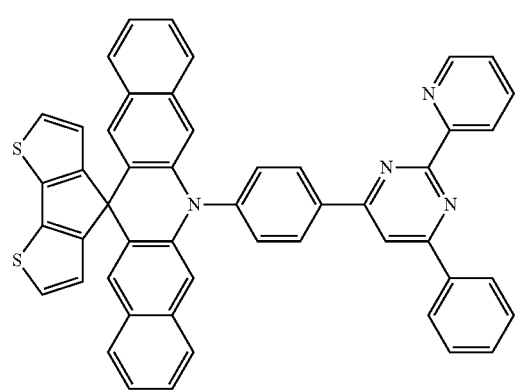
C79
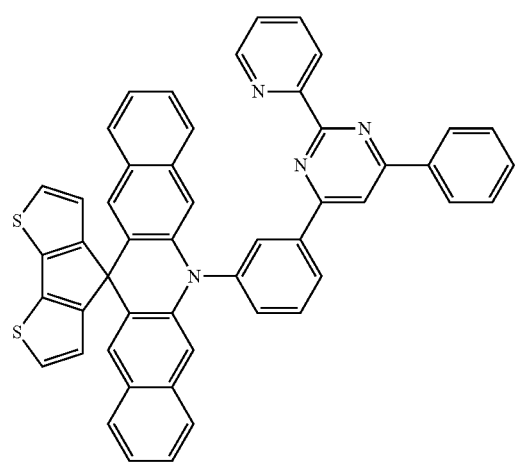

C80
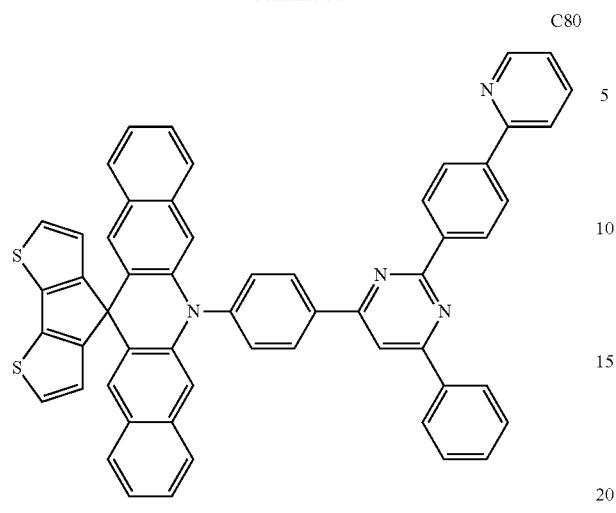
C85
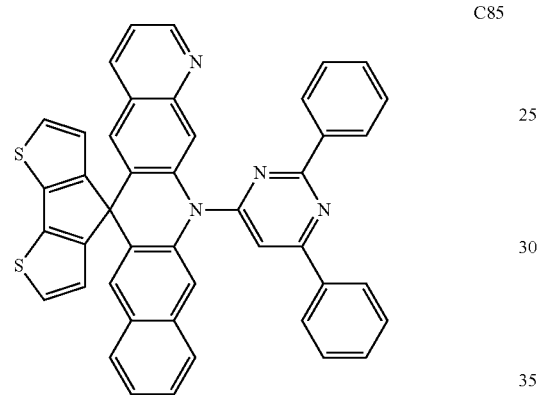
C86
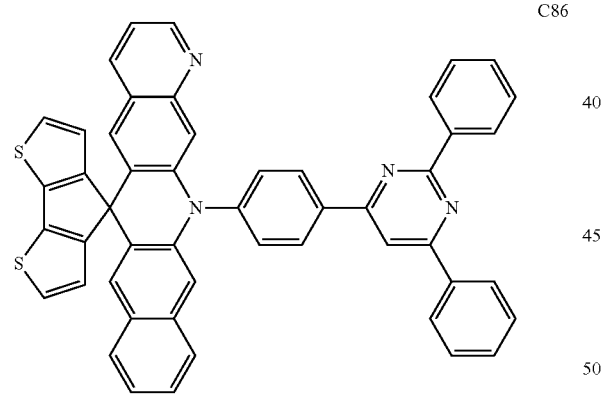
C99
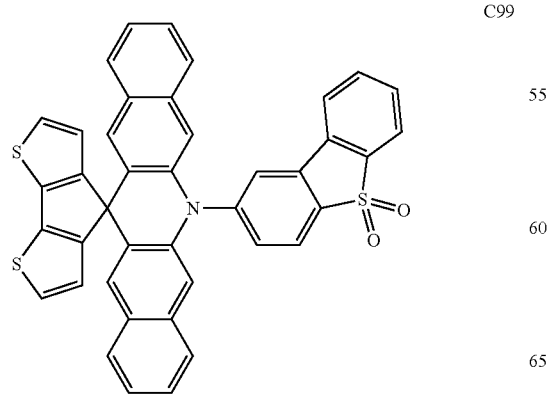
C107
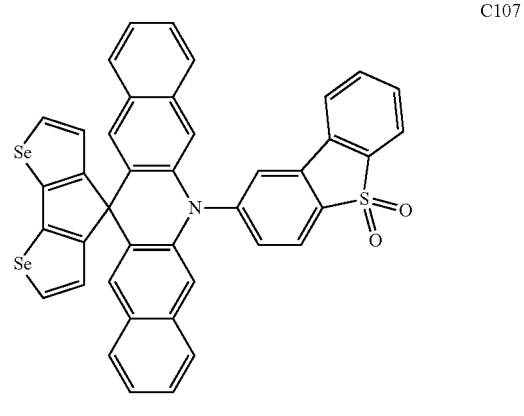
C114
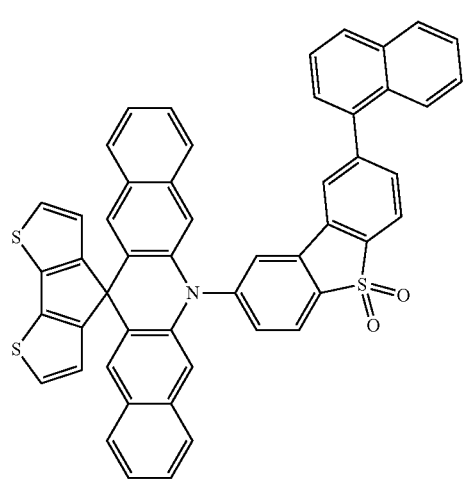
C117
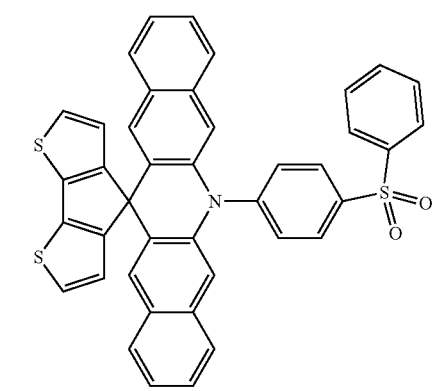
C131
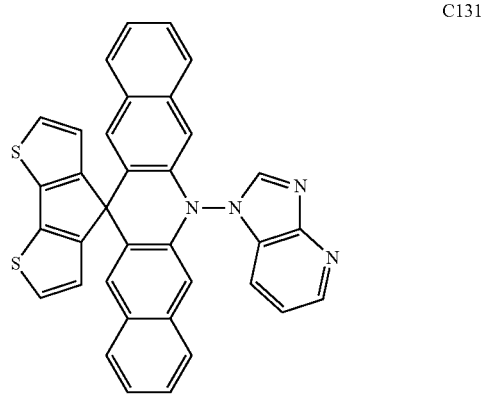 [SMILES: c1ccc2cc3c(cc2c1)N(n1cnc2ncccc21)c1cc2ccccc2cc1C31c2cc[se]c2-c2[se]ccc21]

C132

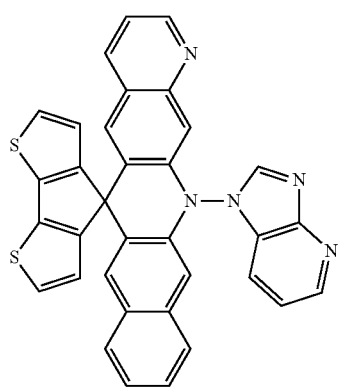

C139

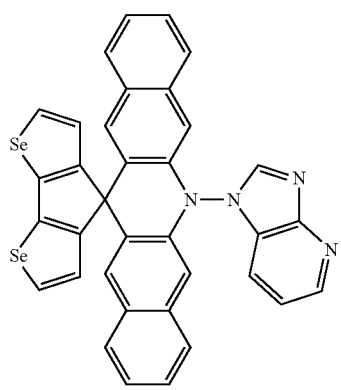

Preferably a difference between a singlet energy of the delayed fluorescence compound and a triplet energy of the delayed fluorescence compound is less than 0.3 eV. In some embodiments, the delayed fluorescence compound is used as a light-emitting material.

In still another embodiment of the present invention, an organic electroluminescent device is disclosed. The organic electroluminescent device comprises a pair of electrodes composed of a cathode and an anode, and a light emitting layer and one or more organic thin film layers between the pair of electrodes. At least one of the light emitting layer and the organic thin film layer comprises the delayed fluorescence compound of formula (1).

In some embodiments, the light emitting layer comprising the delayed fluorescence compound is a delayed fluorescence host material. In some embodiments, the light emitting layer may further comprise a second fluorescence host material. The second fluorescence host material may be H1.

In some embodiments, the light emitting layer comprising the delayed fluorescence compound is a phosphorescent host material. In some embodiments, the light emitting layer may further include a host material, which may be H1, and the delayed fluorescence compound is used as a dopant material. In some embodiments, the light emitting layer may further comprise a second fluorescence dopant material.

In some embodiments, the organic thin film layer may include a hole injection layer, a hole transporting layer, a hole blocking layer, an electron transporting layer, and an electron injection layer, and at least one of the hole injection layer, the hole transporting layer, the hole blocking layer, the electron transporting layer, and the electron injection layer comprises the delayed fluorescence compound.

In some embodiments, the organic thin film layer comprising the delayed fluorescence compound is a hole blocking layer. In some embodiments, the organic thin film layer comprising the delayed fluorescence compound is an electron transporting layer.

In yet another embodiment of the present invention, the organic electroluminescent device is a lighting panel. In a further embodiment of the present invention, the organic electroluminescent device is a backlight panel.

Detailed preparation of the delayed fluorescence compound of the present invention will be clarified by exemplary embodiments below, but the present invention is not limited thereto. EXAMPLES 1 to 7 show the preparation of the delayed fluorescence compound of the present invention, and EXAMPLE 8 shows the fabrication and the testing report of the organic EL device.

EXAMPLE 1

Synthesis of 10H-spiro[acridine-9,4'-cyclopenta[2,1-b:3,4-b']-dithiophene]

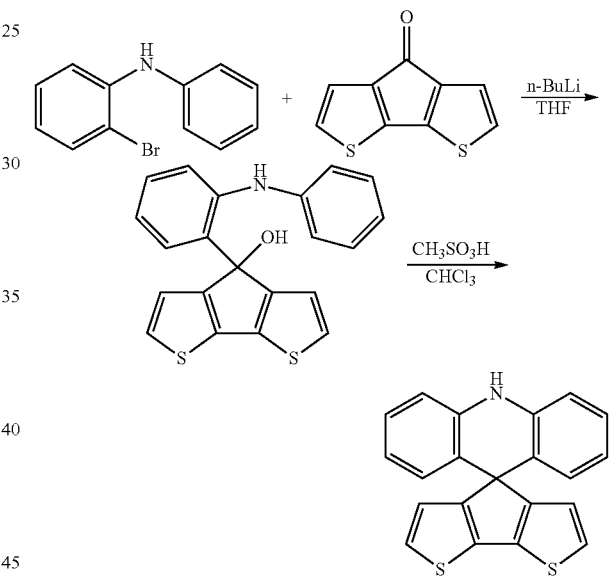

In a 500 ml three-necked flask that had been degassed and filled with nitrogen, 7.1 g (28 mmol) of 2-bromo-N-phenylaniline was dissolved in anhydrous tetrahydrofuran (200 ml) and then cooled to −68° C. Afterwards, 23 ml (58.5 mmol) of n-butyllithium (2.5 M) was slowly added, and then 5 g (26 mmol) of 4'-cyclopenta[2,1-b:3,4-b']dithiophene-4-one dissolved in anhydrous tetrahydrofuran (40 ml) was added. When the mixture was warmed to room temperature after about 15 hours, the organic layer was separated and extracted with chloroform and water, and then the solvent was removed in vacuo to obtain an intermediate. The intermediate, 2.5 g (26 mmol) of methanesulfonic acid, and 100 ml of chloroform were mixed and then heated at 80° C. for 2 hours. After cooling to room temperature, the organic layer was extracted with dichloromethane and NaHCO$_3$(aq), and then dried with anhydrous magnesium sulfate. Afterwards, the solvent was removed and the residue was purified by column chromatography on silica to give 10H-spiro[acridine-9,4'-cyclopenta[2,1-b:3,4-b']dithiophene] (2.67 g, 40%).

Synthesis of Compound C2

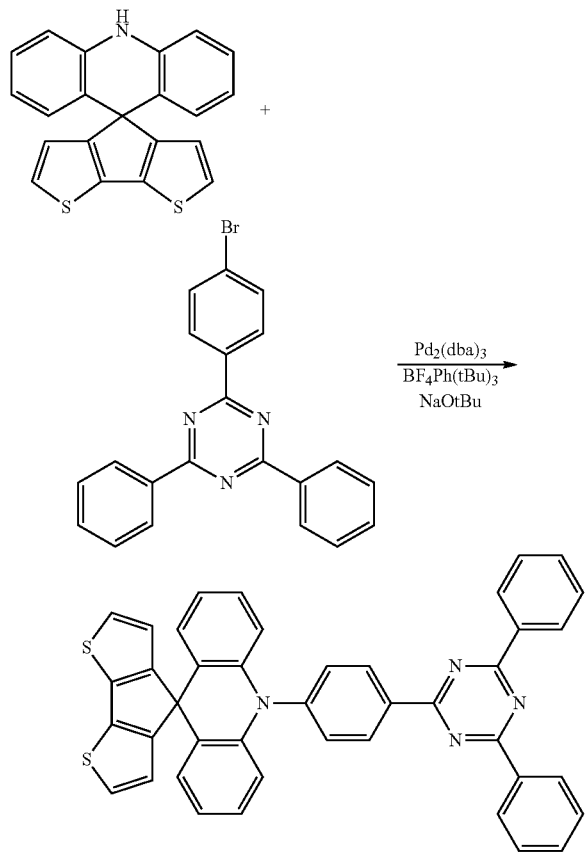

In a 100 ml three-necked flask that had been degassed and filled with nitrogen, 2 g (5.8 mmol) of 10H-spiro[acridine-9,4'-cyclopenta-[2,1-b:3,4-b']-dithiophene], 2.8 g (7 mmol) of 2-(4-bromophenyl)-4,6-diphenyl-1,3,5-triazine, 0.1 g (0.012 mmol) of $Pd_2(dba)_3$, 0.06 g (0.024 mmol) of tri-tert-butylphosphonium tetrafluoroborate, 1.2 g (4.2 mmol) of sodium tert-butoxide, and 40 ml of o-xylene were added, and then heated at 130° C. for 16 hours. After cooling to room temperature, the mixture was filtered to give a solid. The solid was washed with water and MeOH, and then filtered to give compound C2 (3.4 g, 89%) as a dark yellow solid. $^1$H NMR (CDCl$_3$, 500 MHz): chemical shift (ppm) 9.09 (d, 2H), 8.9~8.8 (d, 4H), 7.68~7.58 (m, 8H), 7.17 (d, 2H), 7.02 (d, 2H), 6.98 (m, 2H), 6.67 (d, 4H), 6.46 (d, 2H).

EXAMPLE 2

Synthesis of Compound C3

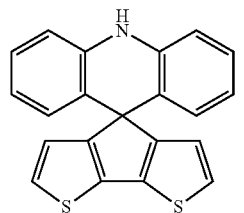

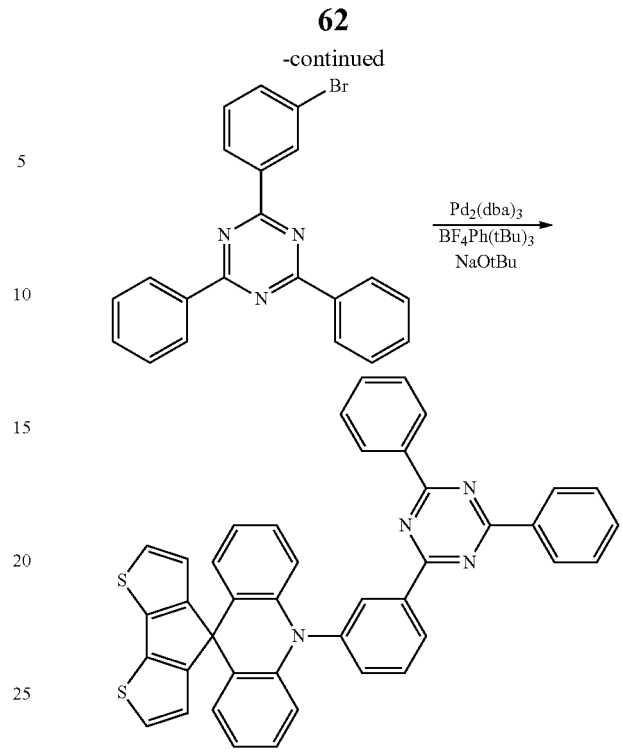

In a 100 ml three-necked flask that had been degassed and filled with nitrogen, 3 g (8.7 mmol) of 10H-spiro[acridine-9,4'-cyclopenta-[2,1-b:3,4-b']-dithiophene], 4.2 g (10.5 mmol) of 2-(3-bromophenyl)-4,6-diphenyl-1,3,5-triazine, 0.15 g (0.018 mmol) of $Pd_2(dba)_3$, 0.09 g (0.036 mmol) of tri-tert-butylphosphonium tetrafluoroborate, 1.8 g (6.3 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C3 (4.5 g, 79%) as a dark yellow solid. $^1$H NMR (CDCl$_3$, 500 MHz): chemical shift (ppm) 9.09 (d, 2H), 8.9~8.8 (d, 4H), 7.68~7.58 (m, 8H), 7.17 (d, 2H), 7.02 (d, 2H), 6.98 (m, 2H), 6.67 (d, 4H), 6.46 (d, 2H).

EXAMPLE 3

Synthesis of Compound C95

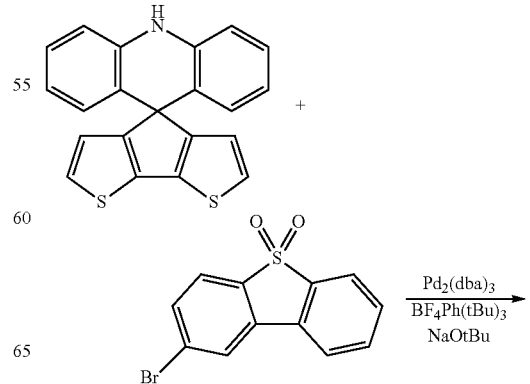

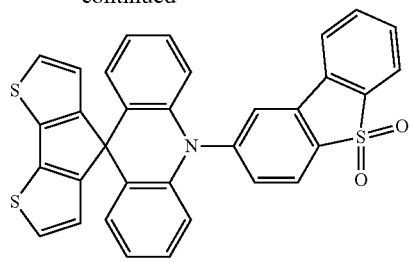

In a 100 ml three-necked flask that had been degassed and filled with nitrogen, 3 g (8.7 mmol) of 10H-spiro[acridine-9,4'-cyclopenta-[2,1-b:3,4-b']-dithiophene], 3.1 g (10.5 mmol) of 2-bromodibenzo[b,d]thiophene5,5-dioxide, 0.15 g (0.018 mmol) of $Pd_2(dba)_3$, 0.09 g (0.036 mmol) of tri-tert-butylphosphonium tetrafluoroborate, 1.8 g (6.3 mmol) of sodium tert-butoxide, and 60 ml of toluene were added, and then heated at 130° C. for 16 hours. After cooling to room temperature, the mixture was filtered to give a solid. The solid was washed with water and MeOH, and then filtered to give compound C95 (4.1 g, 70%) as a dark yellow solid. $^1$H NMR (CDCl$_3$, 500 MHz): chemical shift (ppm) 7.95-7.91 (m, 3H), 7.60 (d, 1H), 7.50 (d, 1H), 7.45~7.44 (d, 2H), 7.18 (d, 2H), 7.08 (d, 2H), 6.96 (m, 2H), 6.68 (d, 4H), 6.48 (d, 2H).

EXAMPLE 4

Synthesis of Compound C115

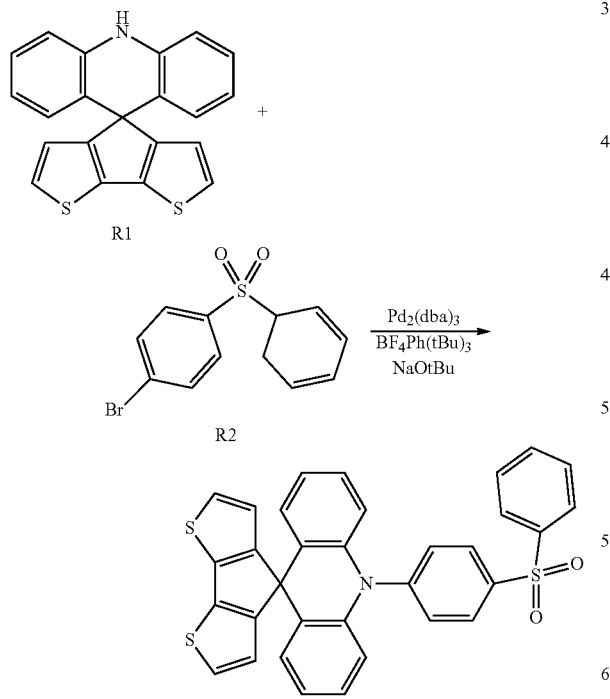

In a 100 ml three-necked flask that had been degassed and filled with nitrogen, 3 g (8.7 mmol) of R1, 3.14 g (10.5 mmol) of R2, 0.15 g (0.018 mmol) of $Pd_2(dba)_3$, 0.09 g (0.036 mmol) of tri-tert-butylphosphonium tetrafluoroborate, 1.8 g (6.3 mmol) of sodium tert-butoxide, and 60 ml of toluene were added, and then heated at 130° C. for 16 hours. After cooling to room temperature, the mixture was filtered to give a solid. The solid was washed with water and MeOH, and then filtered to give compound C115 (3.9 g, 80%) as a dark yellow solid. MS (m/z, EI$^+$):559.72

EXAMPLE 5

Synthesis of Compound C44

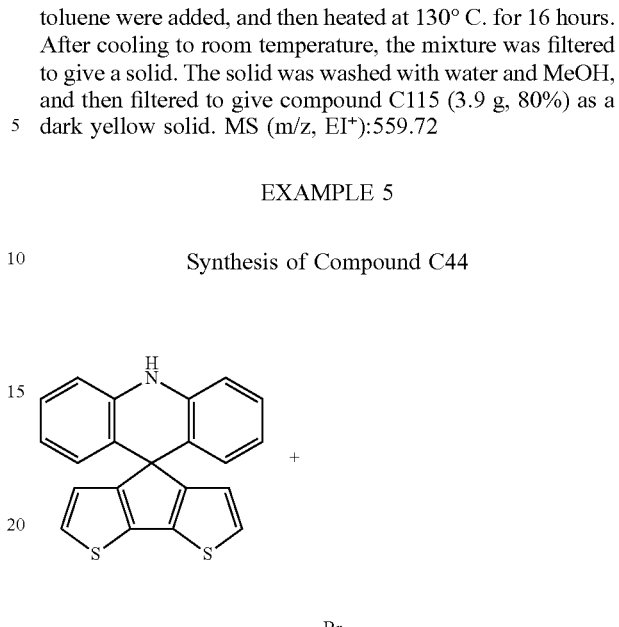

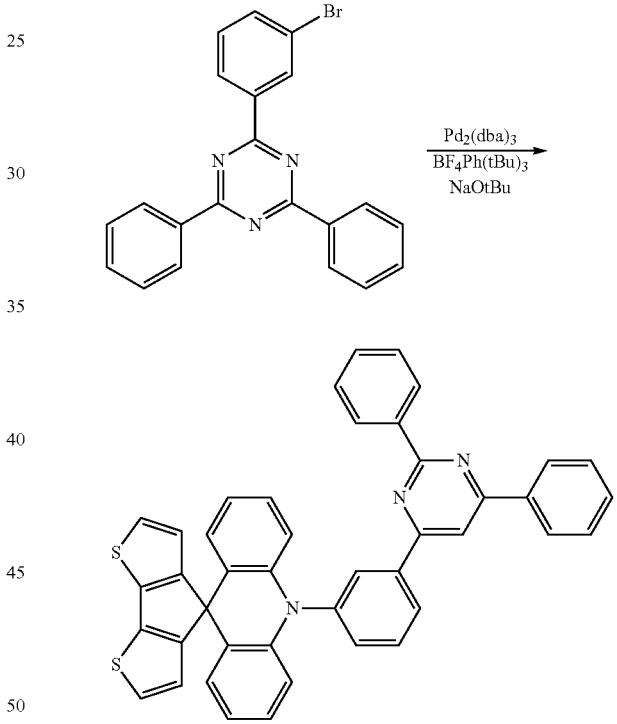

In a 100 ml three-necked flask that had been degassed and filled with nitrogen, 3 g (8.7 mmol) of 10H-spiro[acridine-9,4'-cyclopenta-[2,1-b:3,4-b']-dithiophene], 4.06 g (10.5 mmol) of 2-(3-bromophenyl)-2,6-diphenyl-pyrimidine, 0.15 g (0.018 mmol) of $Pd_2(dba)_3$, 0.09 g (0.036 mmol) of tri-tert-butylphosphonium tetrafluoroborate, 1.8 g (6.3 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C44 (4.08 g, 60%) as a dark orange solid. $^1$H NMR (CDCl$_3$, 500 MHz): chemical shift (ppm) 9.09 (d, 2H), 8.9 ~8.8 (d, 4H), 7.68~7.58 (m, 8H), 7.17 (d, 2H), 7.02 (d, 2H), 6.98 (m, 2H), 6.67 (d, 4H), 6.46 (d, 2H).

EXAMPLE 6

Synthesis of Compound C127

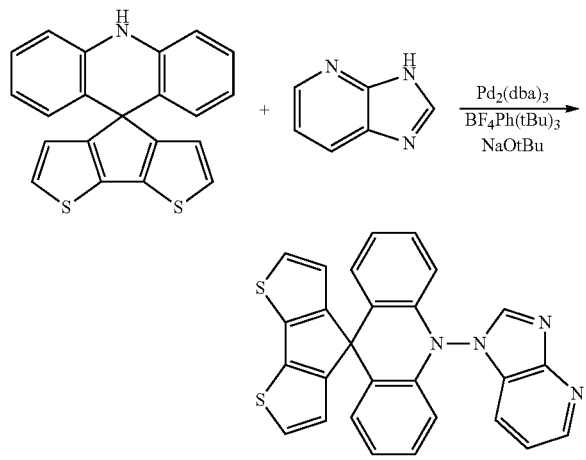

In a 100 ml three-necked flask that had been degassed and filled with nitrogen, 3 g (8.7 mmol) of 10H-spiro[acridine-9,4'-cyclopenta-[2,1-b:3,4-b']-dithiophene], 1.25 g (10.5 mmol) of 3H-imidazo[4,5-b]pyridine, 0.15 g (0.018 mmol) of Pd$_2$(dba)$_3$, 0.09 g (0.036 mmol) of tri-tert-butylphosphonium tetrafluoroborate, 1.8 g (6.3 mmol) of sodium tert-butoxide, and 60 ml of o-xylene were added, and then heated at 130° C. for 16 hours. After cooling to room temperature, the mixture was filtered to give a solid. The solid was washed with water and MeOH, and then filtered to give compound C127 (3.4 g, 60%) as a dark orange solid. MS (m/z, EI$^{30}$):460.57

EXAMPLE 7

Synthesis of 6'H-spiro[cyclopenta[2,1-b:3,4-b']dithiophene-4,13'-dibenzo[b] acridine

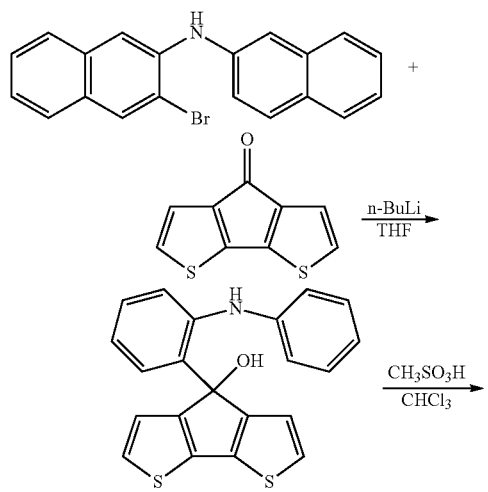

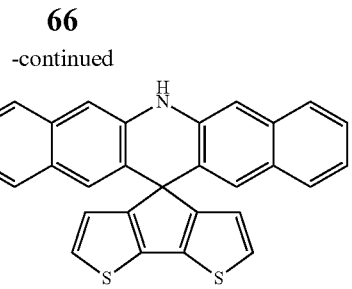

In a 500 ml three-necked flask that had been degassed and filled with nitrogen, 7.1 g (20 mmol) of 3-bromo-N-(naphthalene-2-yl)naphthalene-2-amine was dissolved in anhydrous tetrahydrofuran (200 ml) and then cooled to −68° C. Afterwards, 17 ml (41.7 mmol) of n-butyllithium (2.5 M) was slowly added, and then 3.3 g (18.6 mmol) of 4'-cyclopenta[2,1-b:3,4-b']-dithiophene-4-one dissolved in anhydrous tetrahydrofuran (40 ml) was added. When the mixture was warmed to room temperature after about 15 hours, the organic layer was separated and extracted with chloroform and water, and then the solvent was removed in vacuo to obtain an intermediate. The intermediate, 1.8 g (18.6 mmol) of methanesulfonic acid, and 100 ml of chloroform were mixed and then heated at 80° C. for 2 hours. After cooling to room temperature, the organic layer was extracted with dichloromethane and NaHCO$_3$(aq), and then dried with anhydrous magnesium sulfate. Afterwards, the solvent was removed and the residue was purified by column chromatography on silica to give 6'H-spiro[cyclopenta[2,1-b:3,4-b']-dithiophene-4,13'-dibenzo[b]acridine (3 g, 40%).

Synthesis of Compound C25

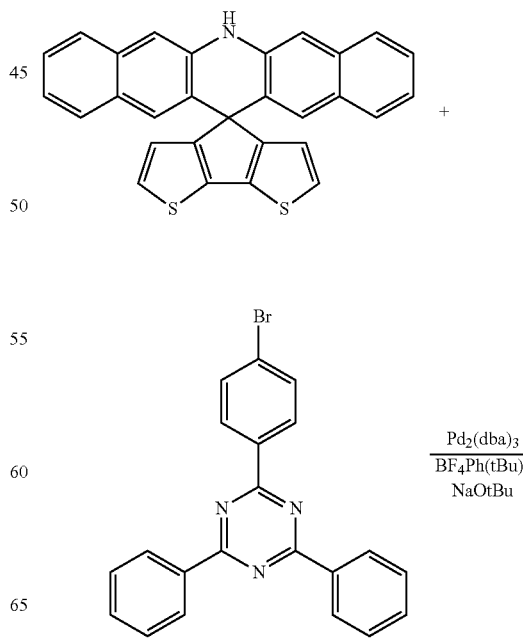

-continued

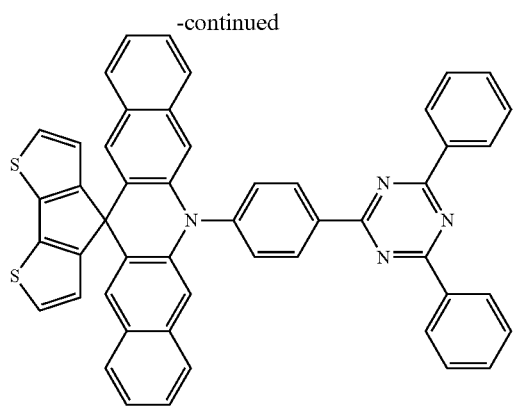

In a 100 ml three-necked flask that had been degassed and filled with nitrogen, 2.57 g (5.8 mmol) of 6'H-spiro[cyclopenta[2,1-b:3,4-b']dithiophene-4,13'-dibenzo[b]acridine, 2.8 g (7 mmol) of 2-(4-bromophenyl)-4,6-diphenyl-1,3,5-triazine, 0.1 g (0.012 mmol) of $Pd_2(dba)_3$, 0.06 g (0.024 mmol) of tri-tert-butylphosphonium tetrafluoroborate, 1.2 g (4.2 mmol) of sodium tert-butoxide, and 40 ml of o-xylene were added, and then heated at 130° C. for 16 hours. After cooling to room temperature, the mixture was filtered to give a solid. The solid was washed with water and MeOH, and then filtered to give compound C25 (3 g, 68%) as a dark yellow solid. MS (m/z, EI$^+$):750.94

Measurement Method of Delayed Fluorescence Compound for Photophysical Properties Photophysical Characterization: Synthesized compounds were subject to purification by temperature-gradient sublimation in high vacuum before use in subsequent studies. Thin films for photophysical characterization were prepared by thermal evaporation on quartz substrates at 1-2 A/sec in a vacuum chamber with a base pressure of <$10^{-6}$ torr. Absorption spectra of the resulting thin films and dilute solutions were characterized by a UV-vis-NIR spectrophotometer (UV-1650 PC, Shimadzu). Photoluminescence (PL) spectra, photoluminescence quantum yields (PLQYs), and phosphorescence spectra were characterized by a spectrofluorimeter (FluoroMax-P, Horiba Jobin Yvon Inc.). PLQYs of thin films or dilute solutions were determined using this spectrofluorimeter equipped with a calibrated integrating sphere. The selected monochromatic excitation light was used to excite samples placed in the calibrated integrating sphere. By comparing the spectral intensities of the monochromatic excitation light and the PL emission, the PL quantum yields were determined. Phosphorescence spectra of thin films or dilute solutions were conducted at 77K (the liquid nitrogen temperature) by the spectrofluorometer equipped with a microsecond flash lamp as the pulsed excitation source. A 10-ms delay time was inserted between the pulsed excitation and the collection of the emission spectrum. Time-resolved PL (PL decay curves) was measured by monitoring the decay of the intensity at the PL peak wavelength using the time-correlated single-photon counting technique with a fluorescence lifetime system (FluoroCube, Horiba JobinYvon Inc.) and nanosecond pulsed light excitation from a UV light-emitting diode (300 nm). The samples were placed in a vacuum cryostat chamber with the temperature control. The PL spectra of the prompt and delayed components were collected using this same fluorescence lifetime system with a 200-ns delay time and a 10-us delay time between the pulsed excitation and the collection of the emission spectrum. Electrochemical Characterization: Cyclic voltammetry by a CHI 619B potentiostat was used to measure oxidation/reduction potentials. The oxidation potential was determined by cyclic voltammetry (CV) using 0.1 M n-Bu4NPF6 (TBAPF6) in $CH_2Cl_2$ as a supporting electrolyte and a scan rate of 100 mVs-1. The reduction potential was recorded using 0.1 M n-Bu4NClO4 (TBAP) in DMF as a supporting electrolyte and a scan rate of 100 mVs–1. A standard 3-electrode cell comprising silver/silver chloride (Ag/AgCl), a platinum wire and a glassy carbon electrode as the reference, counter, and working electrodes, respectively, were used. All potentials were recorded versus Ag/AgCl (saturated) as a reference electrode. Oxidation of the ferrocene/ferrocenium (Fc/Fc+) redox couple in CH2Cl2/TBAPF6 occurs at E'o=+0.47V and reduction of the ferrocene/ferrocenium (Fc/Fc+) redox couple in DMF/TBAP occurs at E"o=+0.51 V vs. Ag/AgCl (saturated) collecting the total emission fluxes with a calibrated integrating-sphere measurement system.

Figure 2:
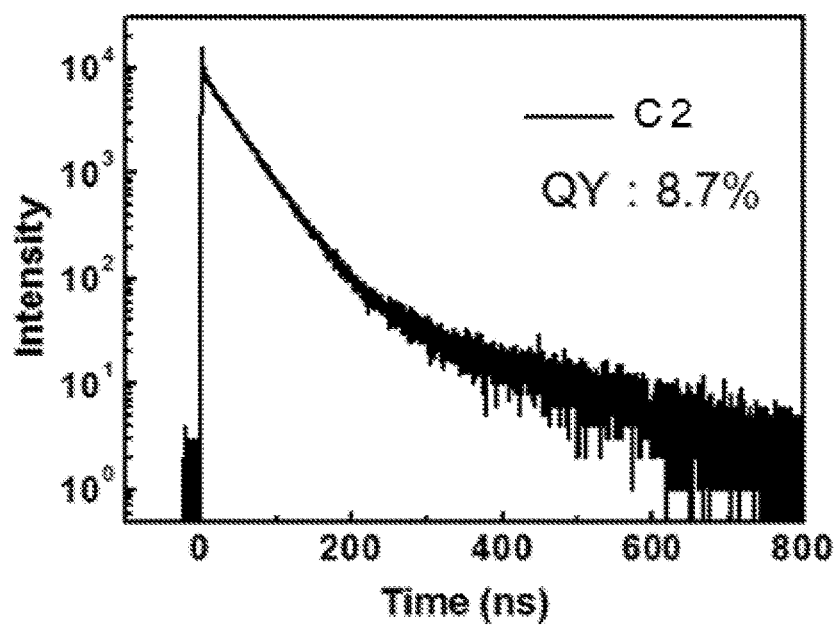
FIG. 2 is a graph showing the transient decay curve of compound C2 and demonstrating the delayed fluorescence property and PLQY.
Figure 3:
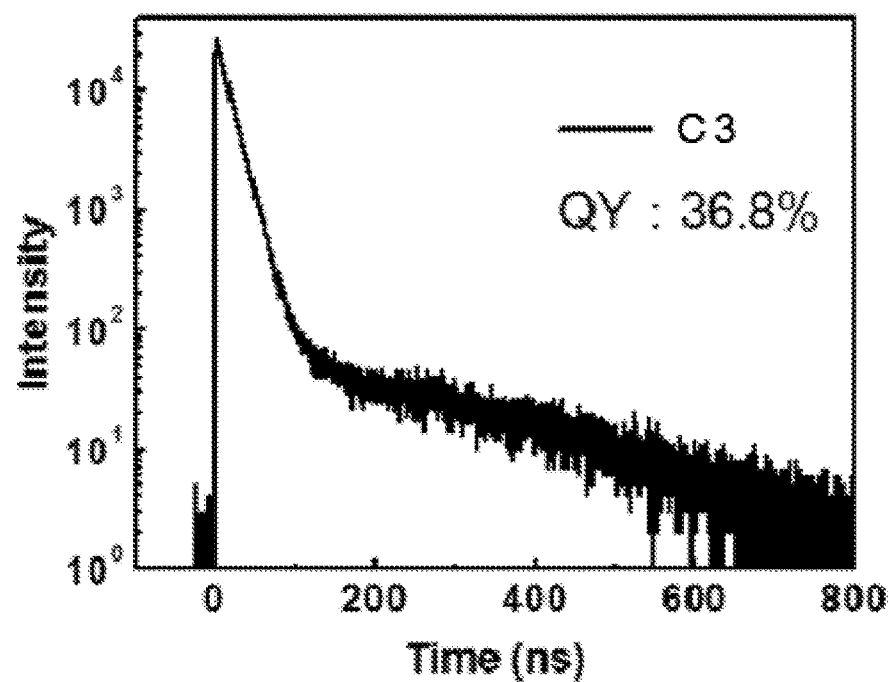
FIG. 3 is a graph showing the transient decay curve of compound C3 and demonstrating the delayed fluorescence property and PLQY.
Figure 4:
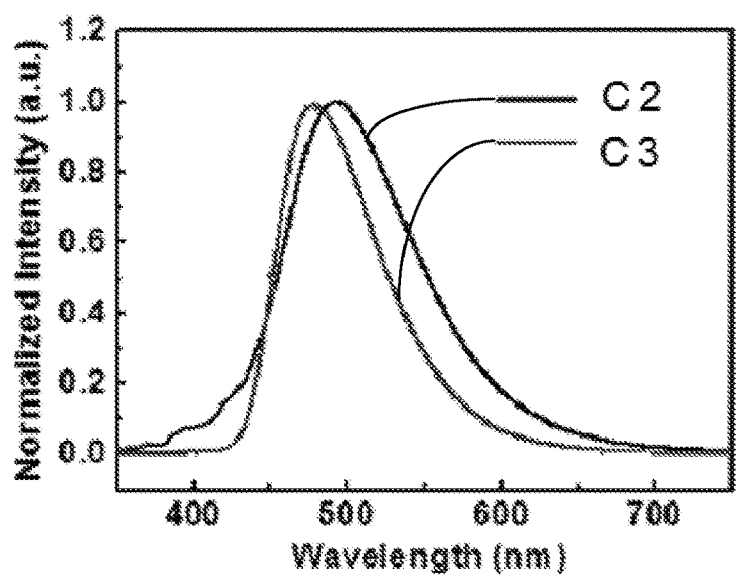
FIG. 4 is a graph showing the photoluminescence (PL) spectra of compounds C2 and C3.

FIG. 2 and FIG. 3 show the transient decay curves of compounds C2 and C3 dissolved in toluene solution. It is obvious from the curves that the delayed fluorescence compounds of the present invention have delayed fluorescence property. FIG. 4 shows the measurement of the photoluminescence spectra of compounds C2 and C3.

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, and N4,N4'-di(biphenyl-4-yl)-N4,N4'-diphenylbiphenyl-4,4'-diamine (HT1) is used as the hole transporting layer, N-(biphenyl-4-yl)-9,9-dimethyl-N-(4'-phenylbiphenyl-4-yl)-9H-fluoren-2-amine (EB2) is used as electron blocking layer, H1 used as phosphorescent host and delayed fluorescence host for comparable or standard with the present invention. The chemical structure shown below:

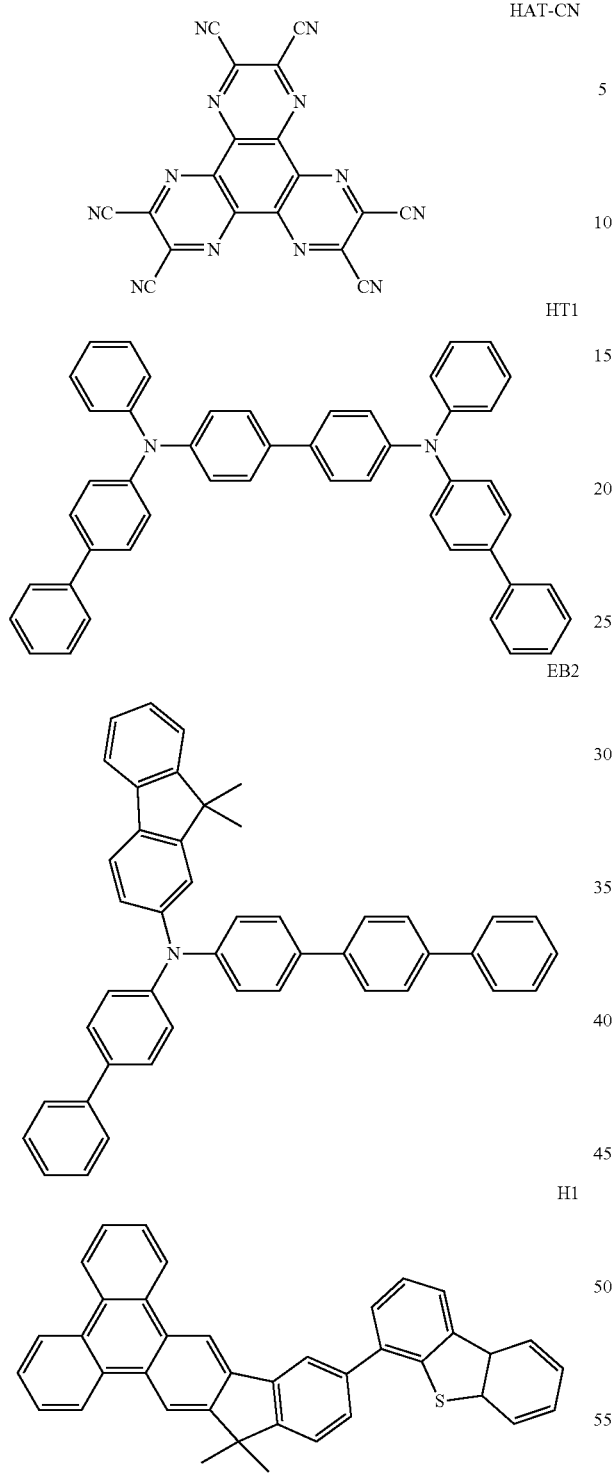
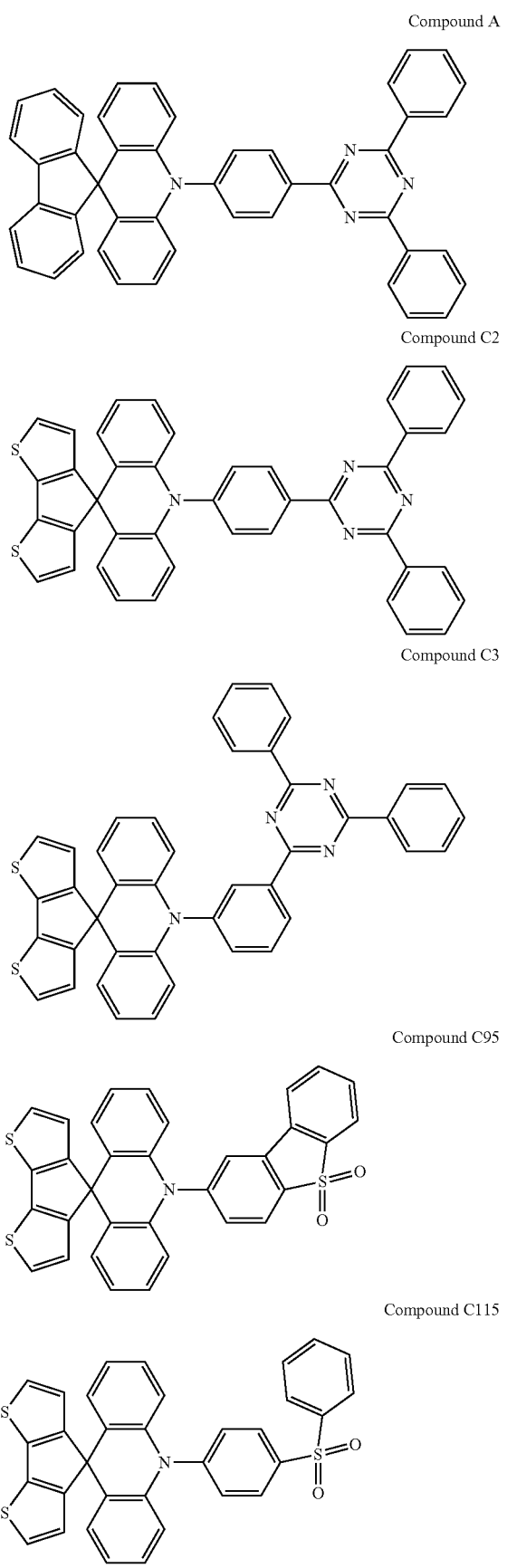

The following delayed fluorescence Examples prepared in the present invention can be verified and used as the delayed fluorescence dopant material, the delayed fluorescence host material, or the phosphorescent host material in the light emitting layer, and/or used in the hole blocking layer and/or the electron transporting layer of the organic EL device. Compound A is used as a compared delayed fluorescence dopant in the present invention. (Compound A is from DOI: 10.1002/adma.201601675.)

-continued

Compound C44

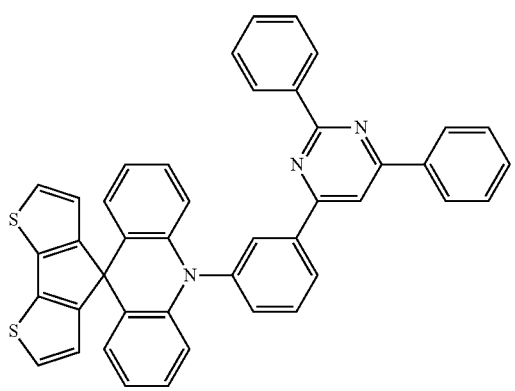

Compound C127

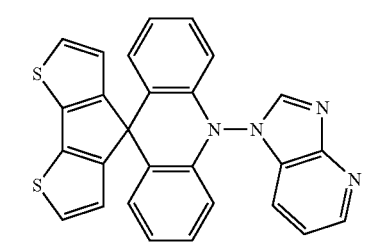

Compound 25

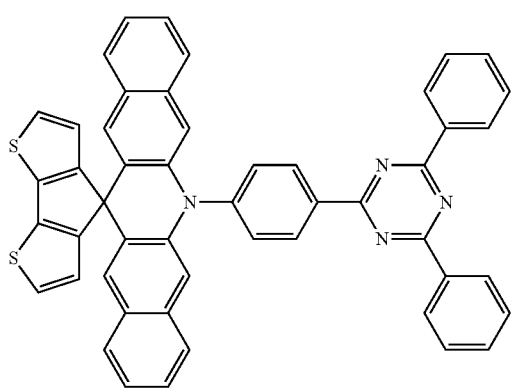

Organic iridium complexes are widely used as phosphorescent dopant for light emitting layer, Ir(ppy)₃ are widely used for phosphorescent green dopant of light emitting layer for organic EL device.

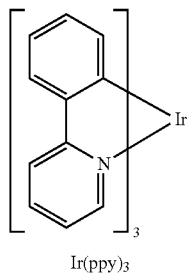

Ir(ppy)₃

2,2',2"-(1,3,5-benzinetriyl)-tris(1-phenyl-1-H-benzimidazole) (TPBi) and HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The chemical structures of conventional OLED materials for producing control and comparable organic EL devices in this invention are shown as follows:

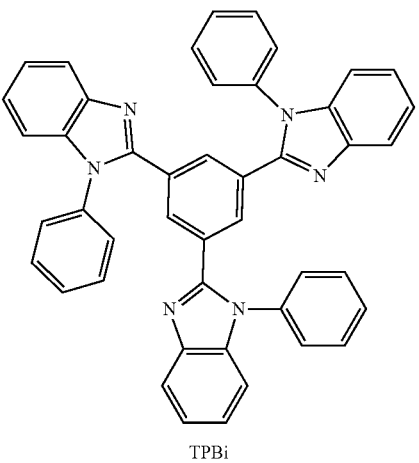

TPBi

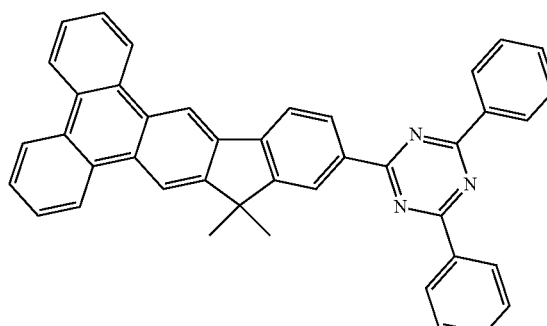

ET2

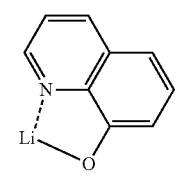

LiQ

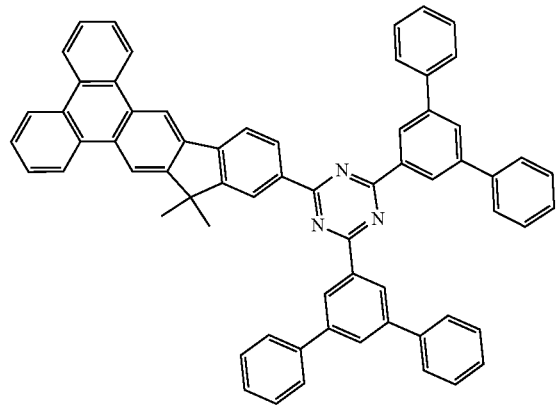

HB3

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li$_2$O. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 8

Using a procedure analogous to the above mentioned general method, organic EL device having the following device structure was produced (see FIG. 1). Device: ITO/HAT-CN (20 nm)/HT1 (110 nm)/EB2 (5 nm)/Host+10%~30% dopant (30 nm)/HBM (10 nm)/ETM doped 40% LiQ (35 nm)/LiQ (1 nm)/Al (160 nm). The I-V-B testing reports (at 1000 nits) of organic EL devices are shown in Table 1.

TABLE 1

| Dopant (%) | Host | HBM | ETM | Voltage (V) | Efficiency (cd/A) |
|---|---|---|---|---|---|
| A (20%) | H1 | TPBi | ET2 | 5.0 | 10 |
| C2 (20%) | H1 | TPBi | ET2 | 4.9 | 14 |
| C3 (20%) | H1 | TPBi | ET2 | 4.8 | 20 |
| C44 (25%) | H1 | TPBi | ET2 | 5.0 | 18 |
| C25 (25%) | H1 | TPBi | ET2 | 4.9 | 13 |
| C2 (20%) | C127 | TPBi | ET2 | 4.8 | 14 |
| Ir(ppy)$_3$(8%) | H1 | HB3 | ET2 | 4.9 | 10 |
| Ir(ppy)$_3$(8%) | C127 | HB3 | ET2 | 4.8 | 14 |
| Ir(ppy)$_3$(8%) | H1 | C115 | ET2 | 4.8 | 15 |
| Ir(ppy)$_3$(8%) | H1 | C95 | ET2 | 4.7 | 16 |
| Ir(ppy)$_3$(8%) | H1 | HB3 | C2 | 4.9 | 19 |
| Ir(ppy)$_3$(8%) | H1 | HB3 | C3 | 4.8 | 20 |

In the above preferred embodiments for organic EL device testing (see Table 1), we show that the delayed fluorescence compound of formula (1) used as the thermally activated delayed fluorescence (TADF) dopant material, the delayed fluorescence host material, or the phosphorescent host material in the light emitting layer, or used in the hole blocking layer or the electron transporting layer of the organic EL device of the present invention display better performance than the organic EL materials of prior arts. In particular, compound C3 used as the delayed fluorescence dopant material of the organic EL device shows better efficiency than compound A.

To sum up, the present invention discloses the delayed fluorescence compound, which can be used as the delayed fluorescence dopant material, the delayed fluorescence host material, or the phosphorescent host material in the light emitting layer, and/or used in the hole blocking layer and/or the electron transporting layer of the organic EL device. The mentioned delayed fluorescence compound is represented by the following formula (1):

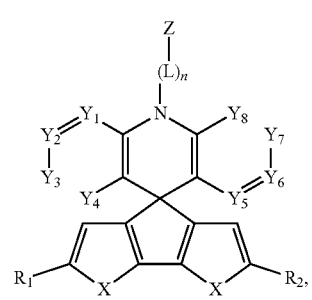

formula (1)

wherein X is O, S, or Se; Y$_1$-Y$_8$ are each independently a nitrogen atom or CR; R, R$_1$, and R$_2$ are each independently selected from the group consisting of a hydrogen atom, a halide, a nitro, a pyridine, a pyrazine, a pyrimidine, a pyridazine, a substituted or unsubstituted alkyl group having 1 to 30 carbon atoms, a substituted or unsubstituted alkenyl group having 1 to 30 carbon atoms, a substituted or unsubstituted aryl group having 6 to 30 carbon atoms, and a substituted or unsubstituted heteroaryl group having 3 to 30 carbon atoms; L represents formula (2):

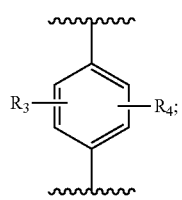

formula (2)

n is 0 or 1; and Z is selected from formulas (3)-(7):

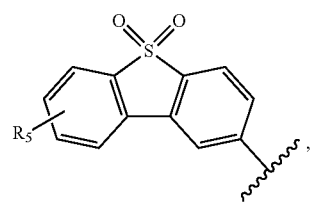

formula (3)

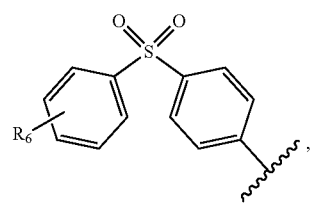

formula (4)

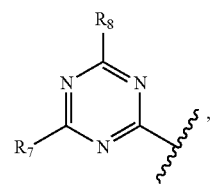

formula (5)

-continued

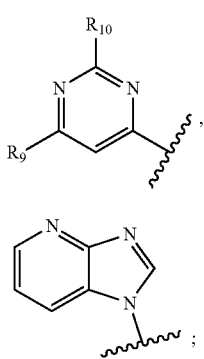
formula (6)

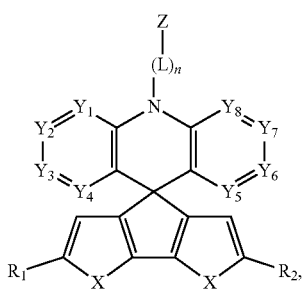
formula (7)

and
wherein $R_3$ to $R_{10}$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted heteroaryl group having 3 to 30 carbon atoms, and a substituted or unsubstituted aralkyl group having 6 to 30 carbon atoms; $Y_2$ and $Y_3$ are optionally connected to each other to form an aromatic or heteroaromatic ring; and $Y_6$ and $Y_7$ are optionally connected to each other to form an aromatic or heteroaromatic ring.

The invention claimed is:

1. A delayed fluorescence compound of formula (1):

formula (1)

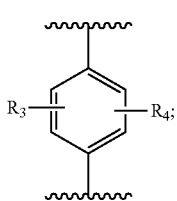

wherein X is O, S, or Se; $Y_1$-$Y_8$ are each independently a nitrogen atom or CR; R, $R_1$, and $R_2$ are each independently selected from the group consisting of a hydrogen atom, a halide, a nitro, a pyridine, a pyrazine, a pyrimidine, a pyridazine, a substituted or unsubstituted alkyl group having 1 to 30 carbon atoms, a substituted or unsubstituted alkenyl group having 1 to 30 carbon atoms, a substituted or unsubstituted aryl group having 6 to 30 carbon atoms, and a substituted or unsubstituted heteroaryl group having 3 to 30 carbon atoms; L represents formula (2):

formula (2)

n is 0 or 1; and Z is selected from formulas (3)-(7):

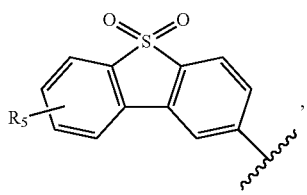
formula (3)

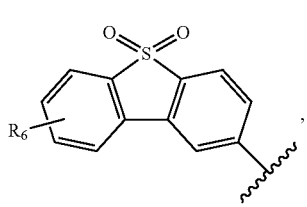
formula (4)

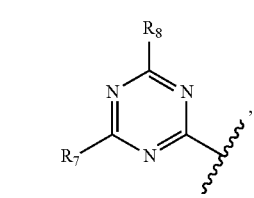
formula (5)

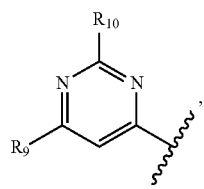
formula (6)

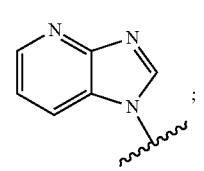
formula (7)

and
wherein $R_3$ to $R_{10}$ are each independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted heteroaryl group having 3 to 30 carbon atoms, and a substituted or unsubstituted aralkyl group having 6 to 30 carbon atoms; $Y_2$ and $Y_3$ are optionally connected to each other to form an aromatic or heteroaromatic ring; and $Y_6$ and $Y_7$ are optionally connected to each other to form an aromatic or heteroaromatic ring.

2. The delayed fluorescence compound of claim 1, comprising a structure of formula (8):

formula (8)

wherein $Y_9$-$Y_{16}$ are each independently a nitrogen atom or CR; and R, $R_1$, $R_2$, X, L, n, and Z have the same meaning as defined in claim 1.

3. The delayed fluorescence compound of claim 1, wherein the delayed fluorescence compound is one of the following compounds:

C1

C2

C3

C4

C5

C6

-continued
C7
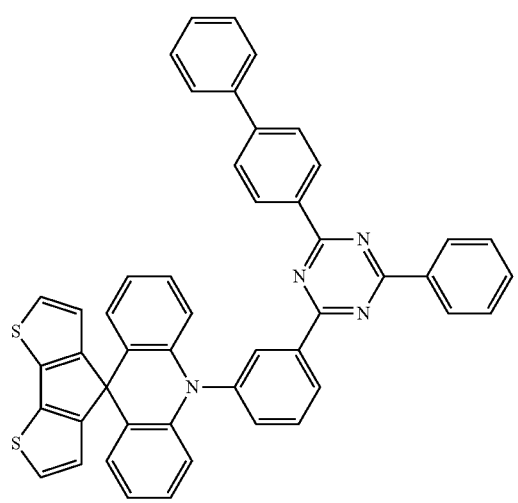
C8
C9
-continued
C10
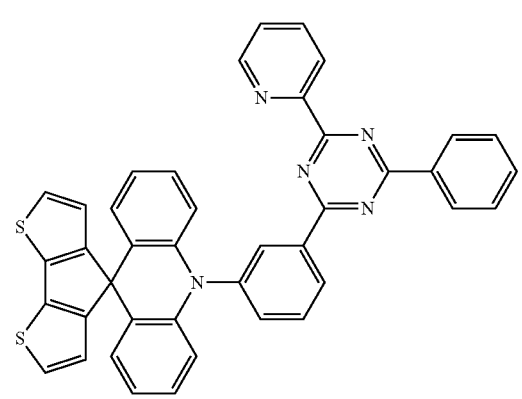
C11
C12
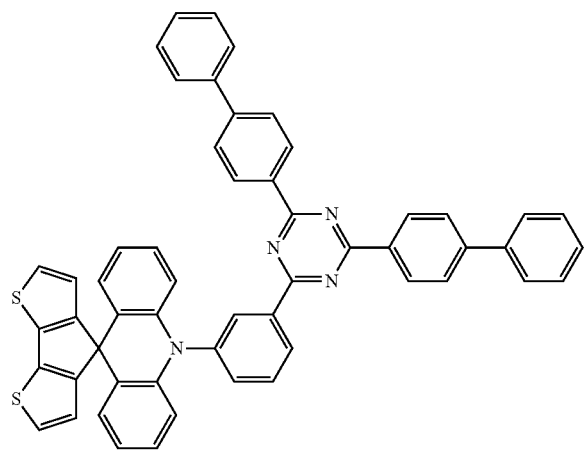

C13
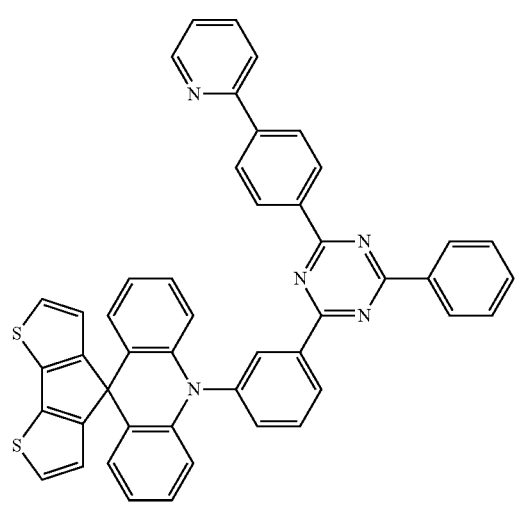
C14
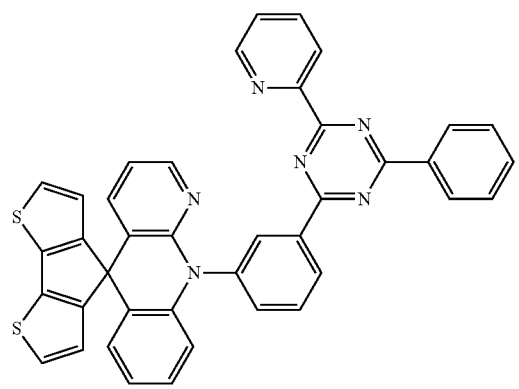
C15
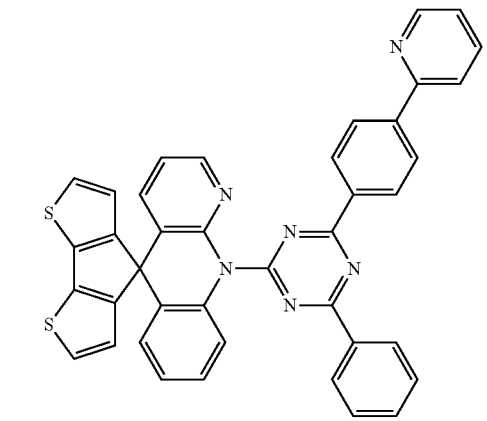
C16
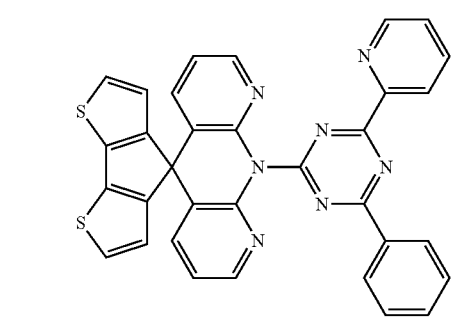
C17
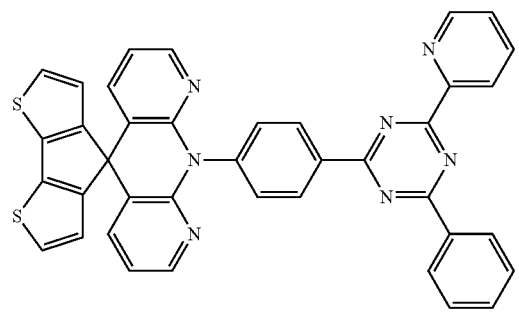
C18
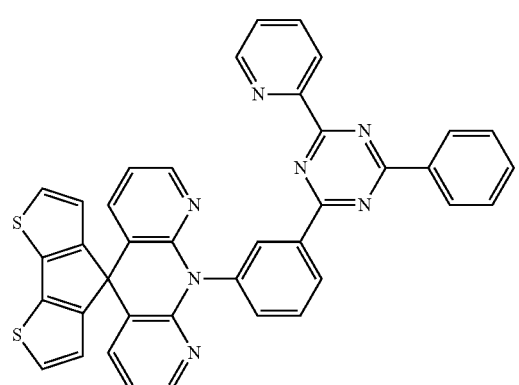
C19
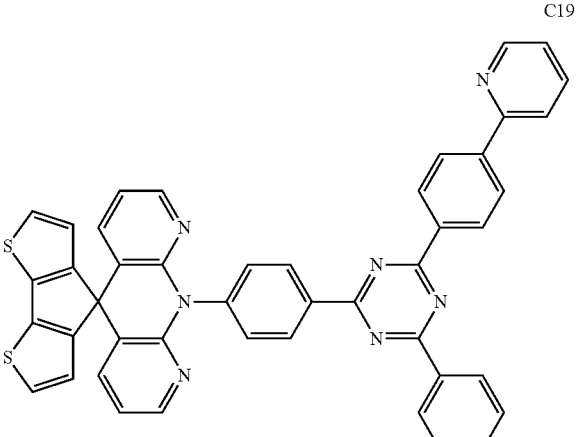
C20
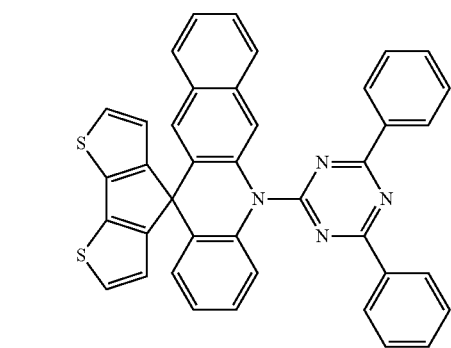

C21
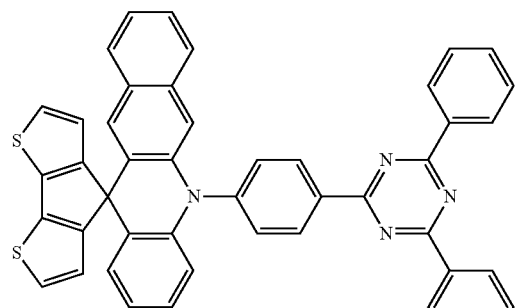
C22
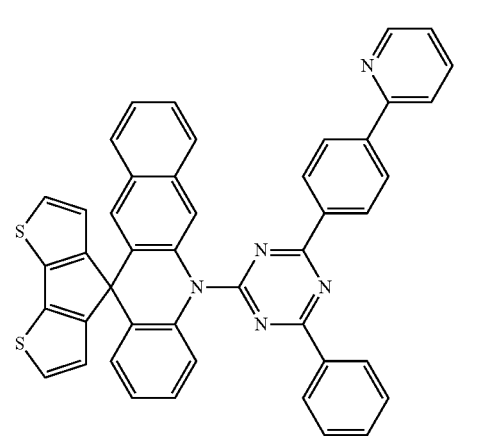
C23
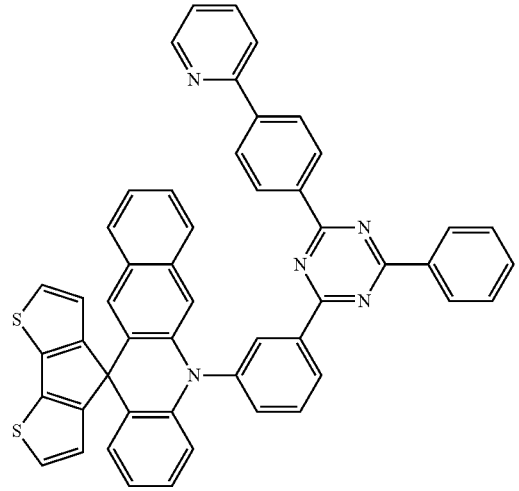
C24
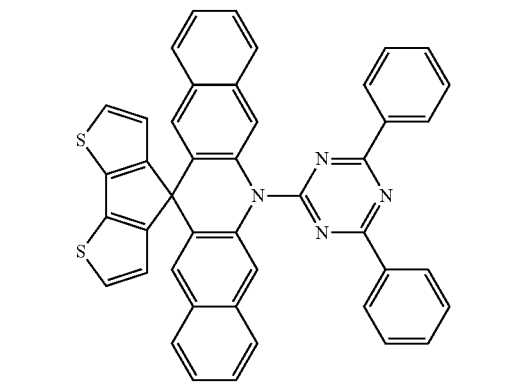
C25
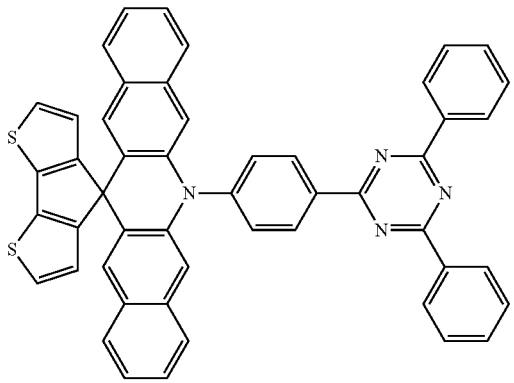
C26
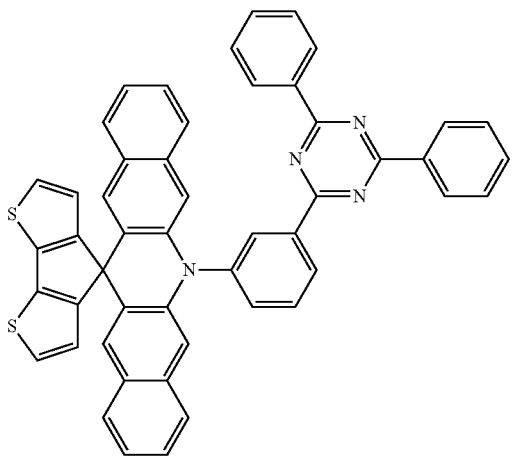
C27
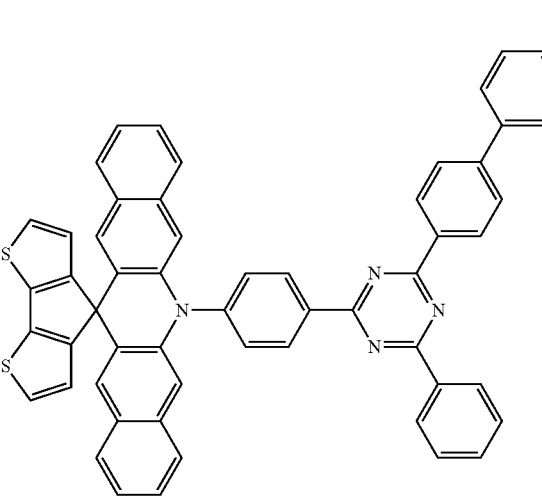

-continued
C28
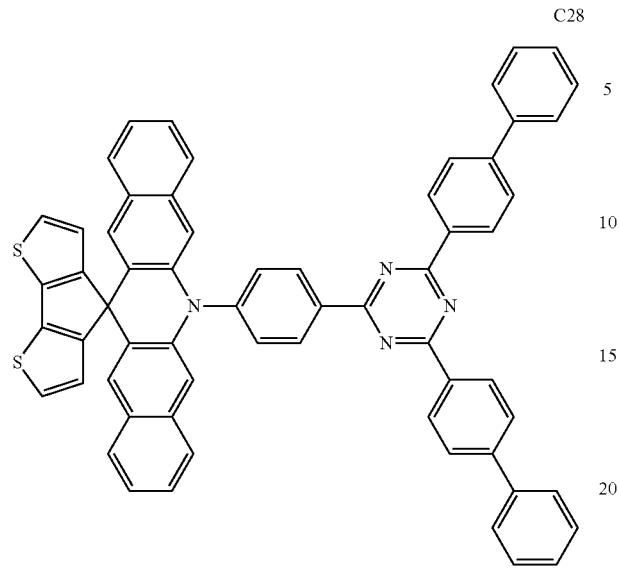
C29
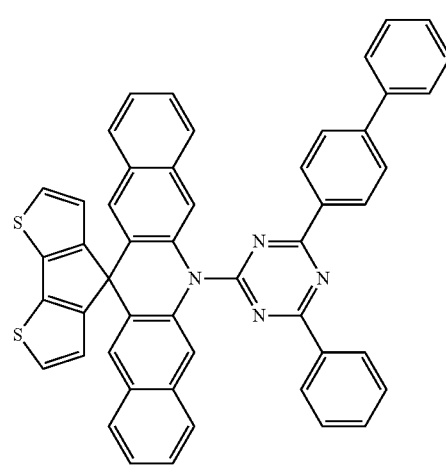
C30
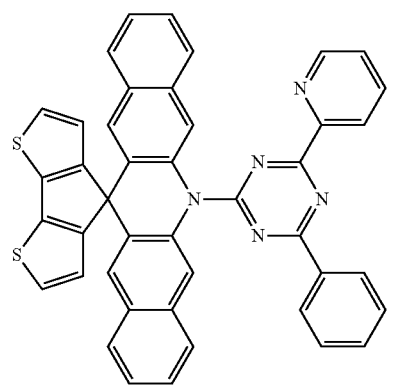
-continued
C31
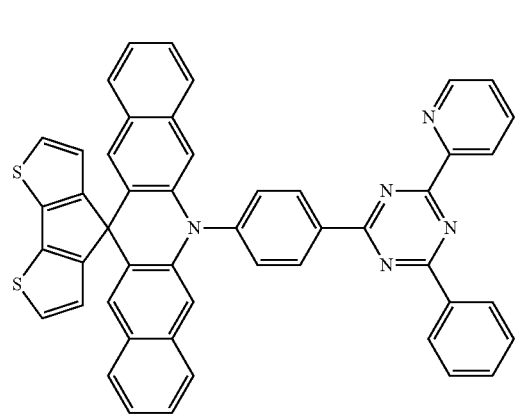
C32
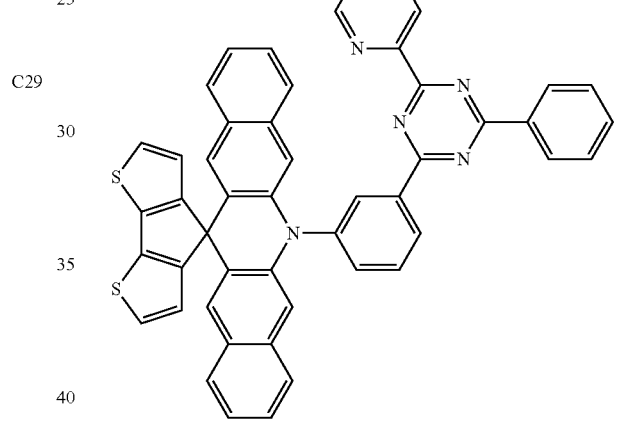
C33
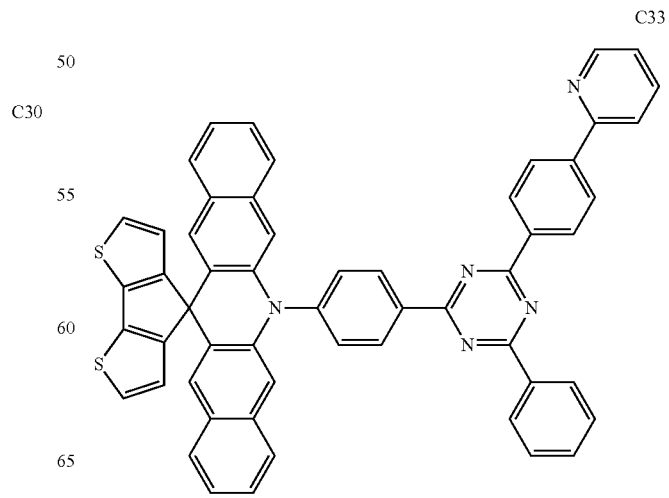

87
-continued
C34
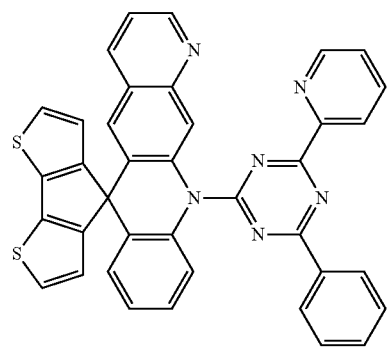
C35
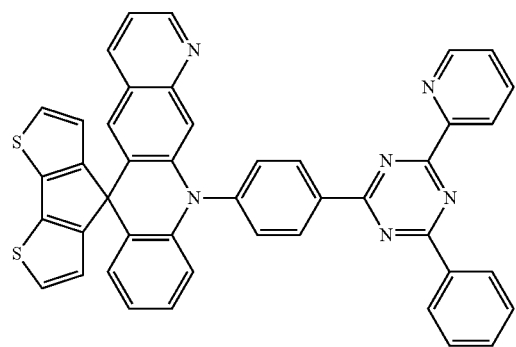
C36
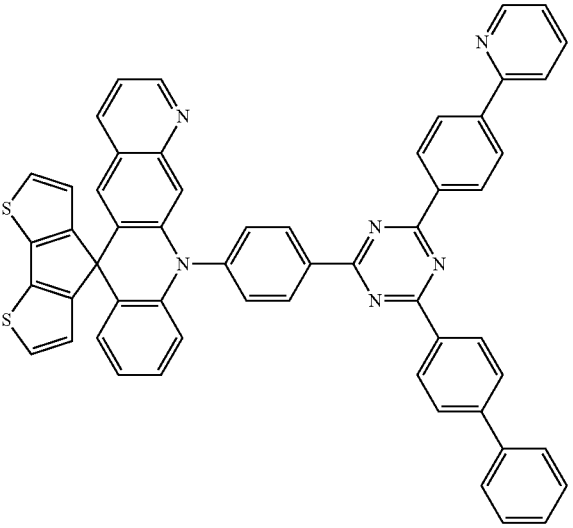
88
-continued
C37
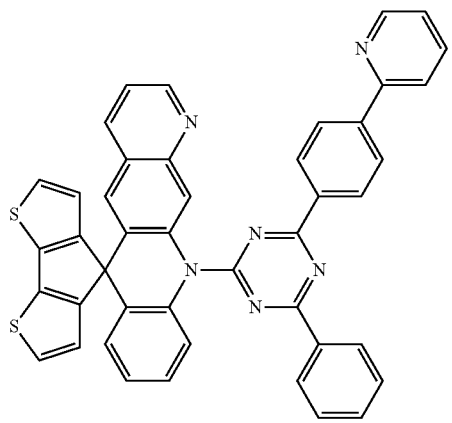
C38
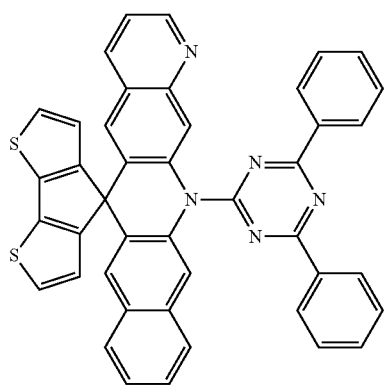
C39
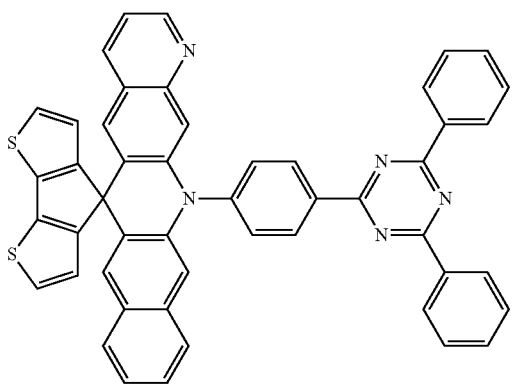
C40
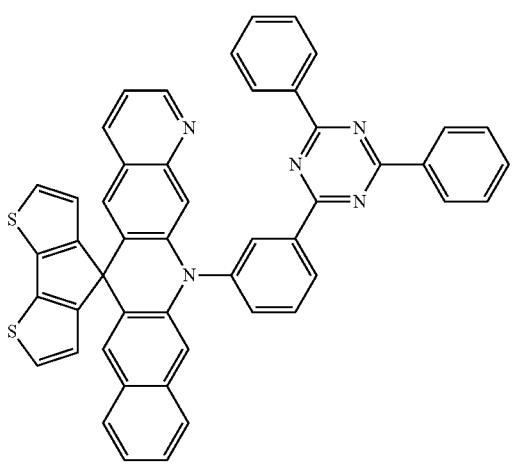

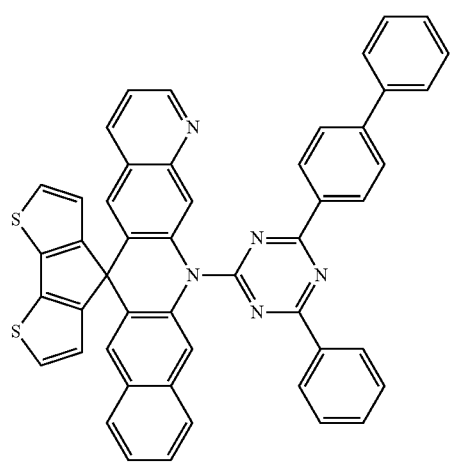
C41
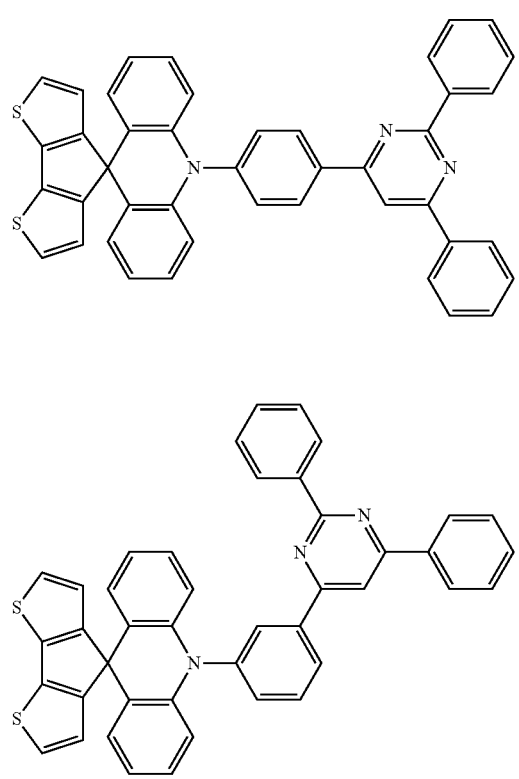
C42
C43
C44
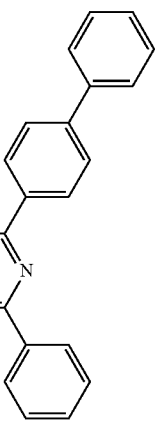
C45
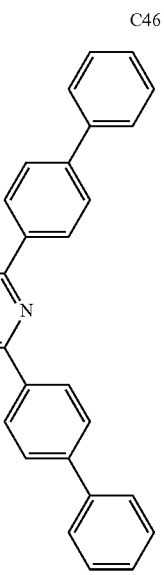
C46
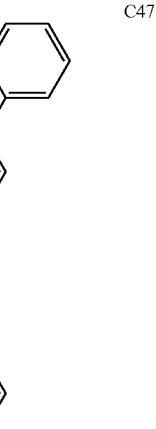
C47

C48
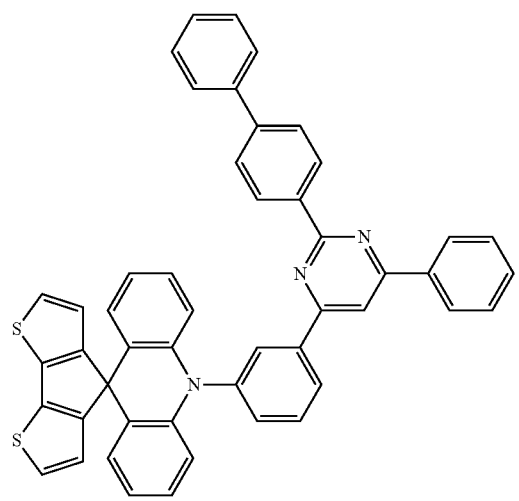
C49
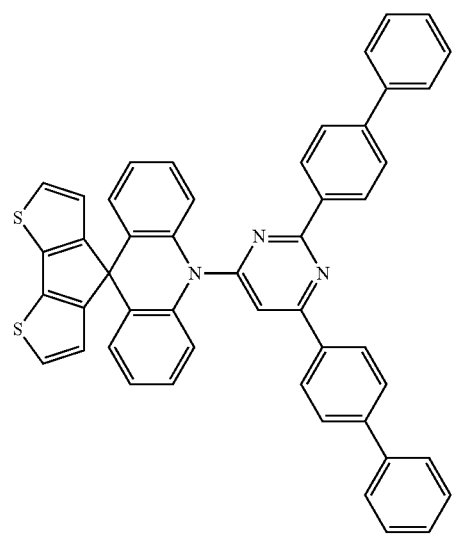
C50
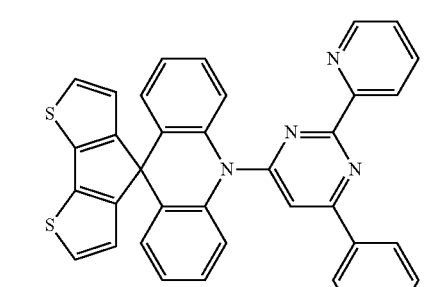
C51
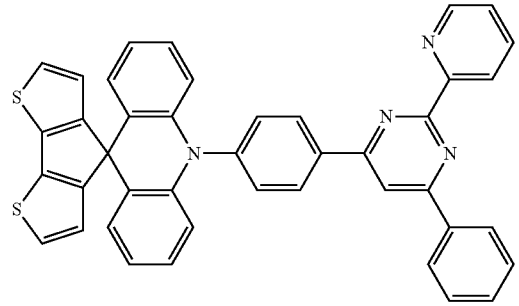
C52
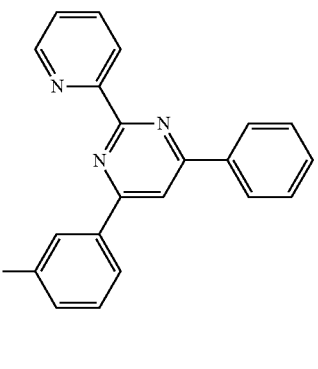
C53
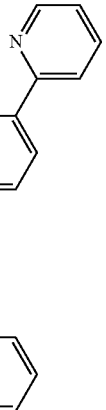
C54

C55
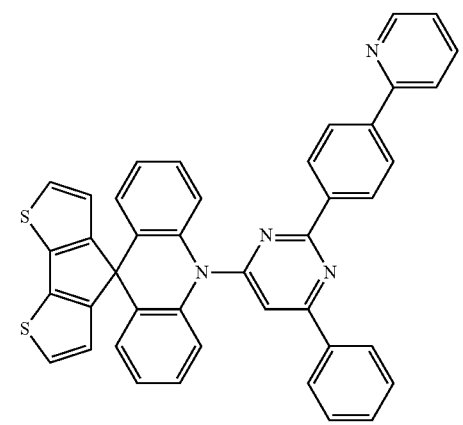
C56
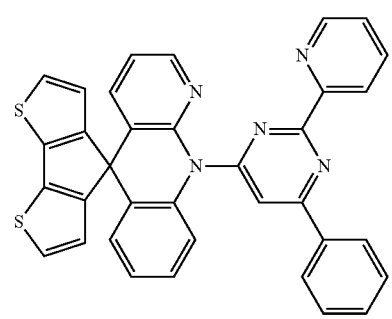
C57
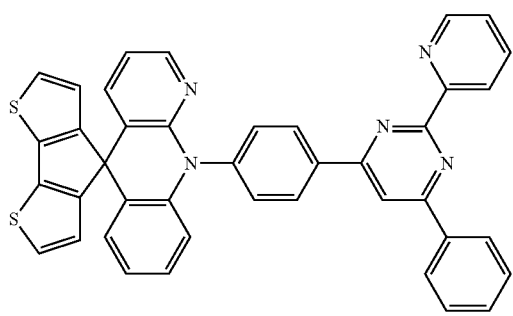
C58
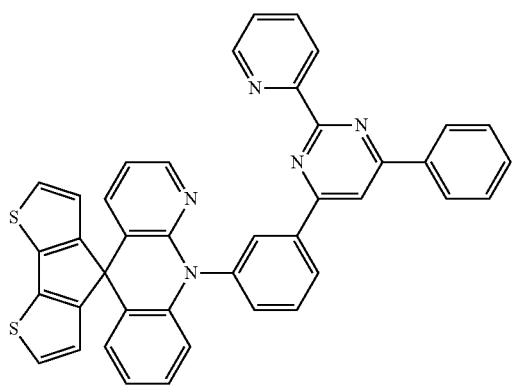
C59
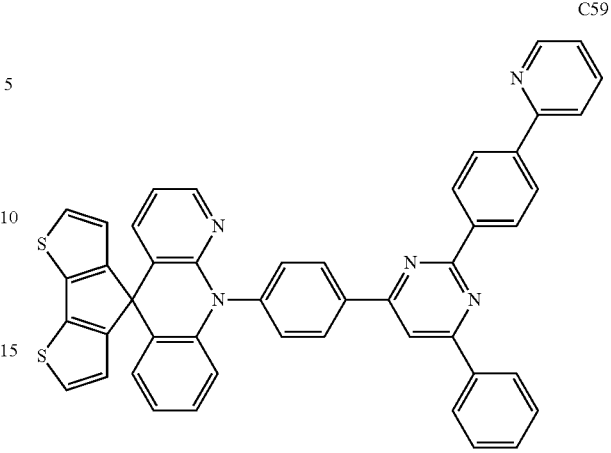
C60
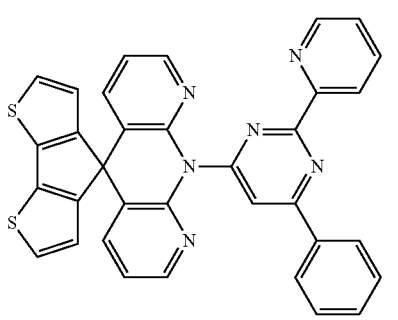
C61
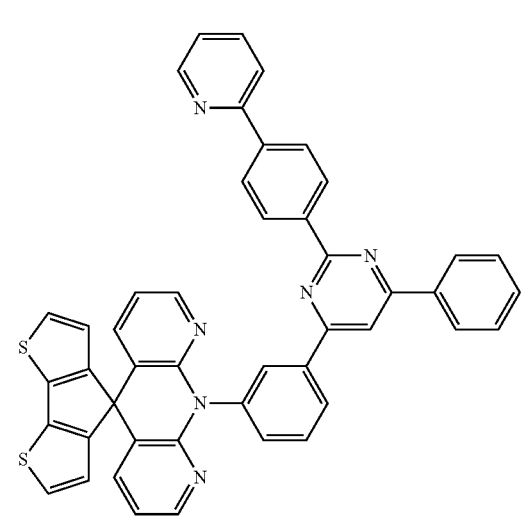
C62

C63
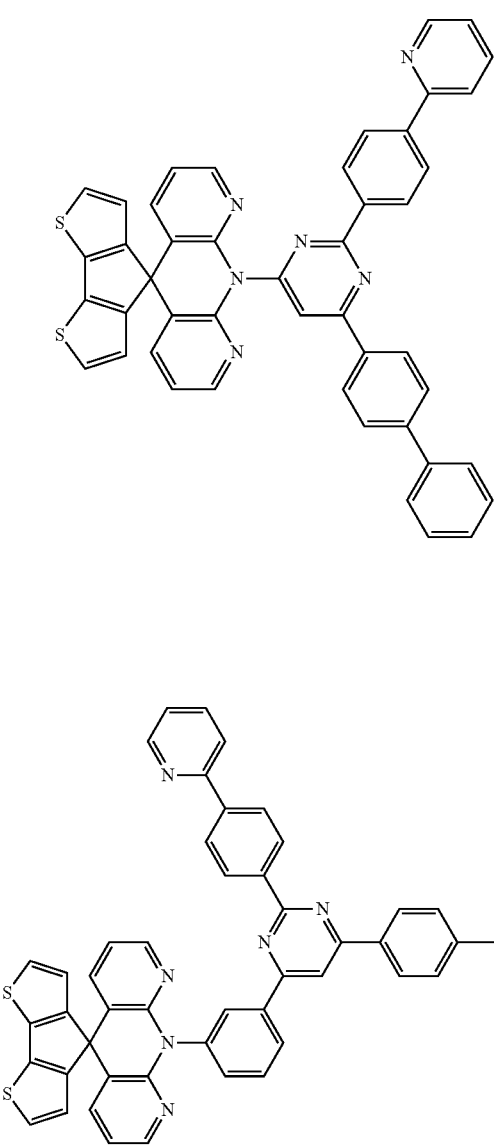
C64
C65
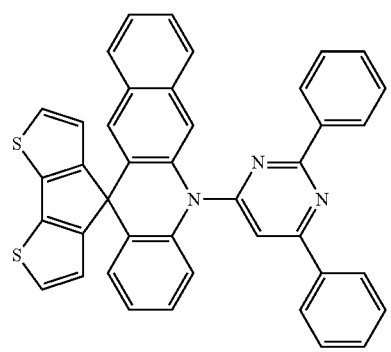
C66
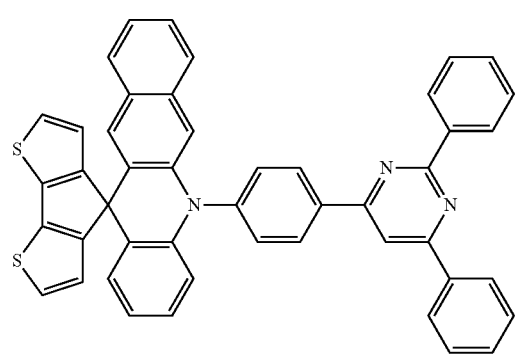
C67
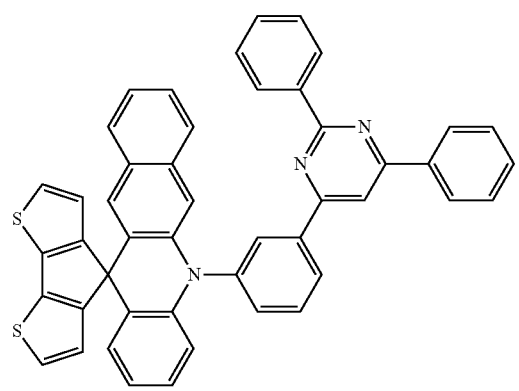
C68
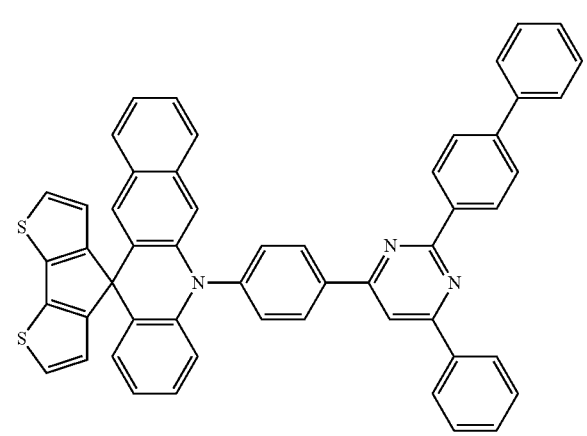
C69
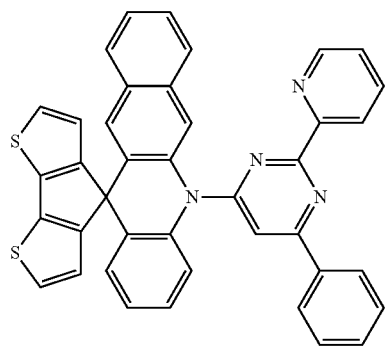

97
-continued
C70
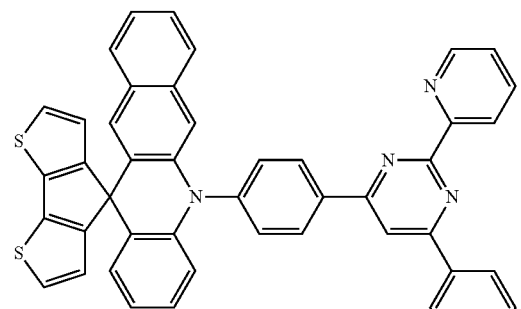
C71
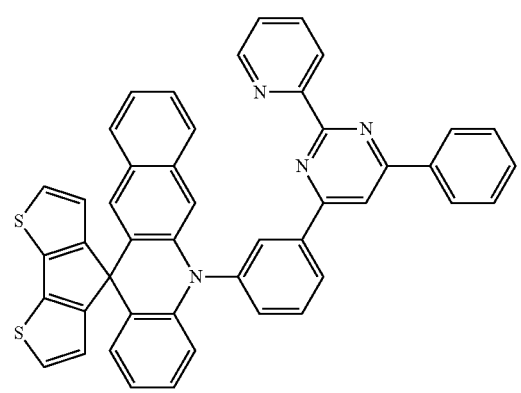
C72
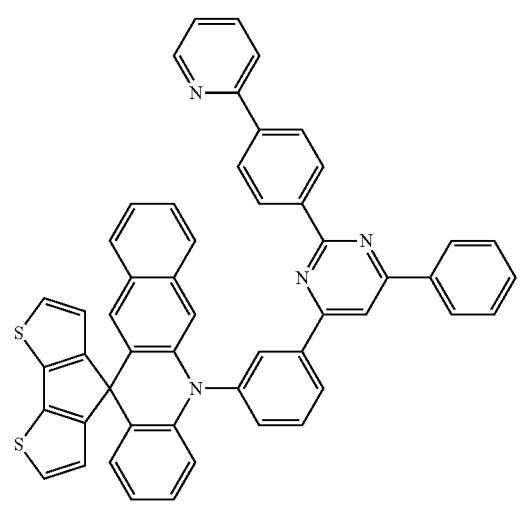
C73
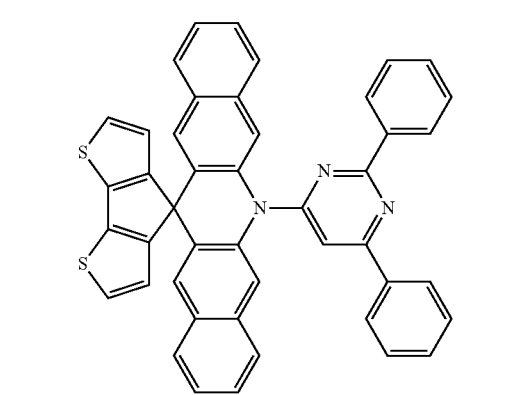
98
-continued
C74
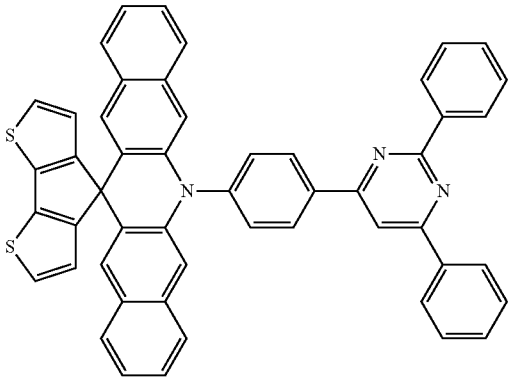
C75
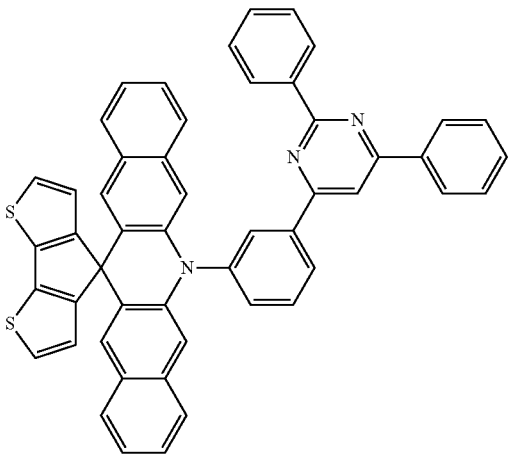
C76
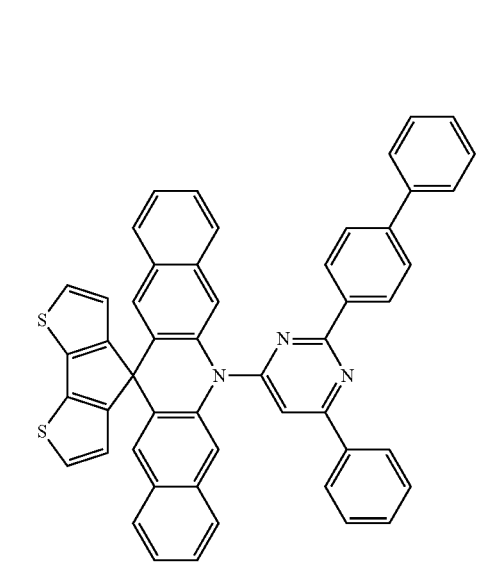

-continued
C77
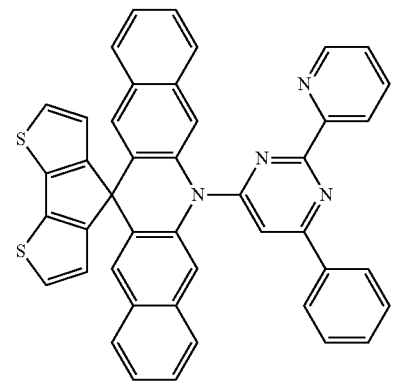
C78
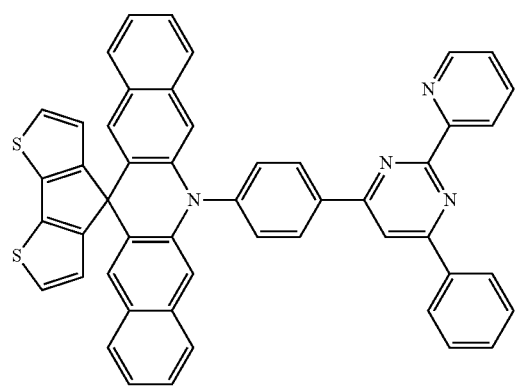
C79
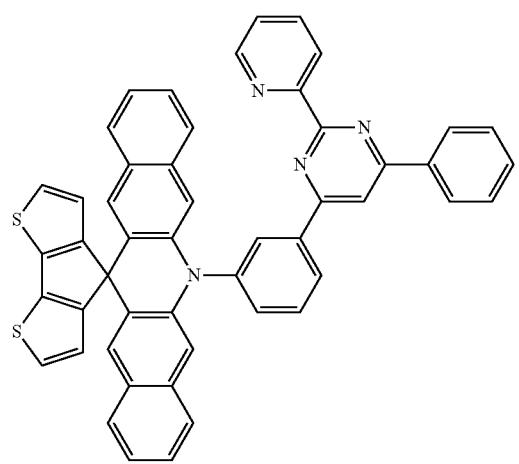
-continued
C80
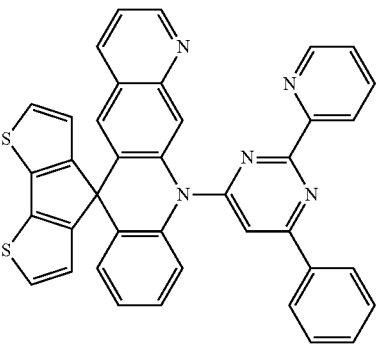
C81
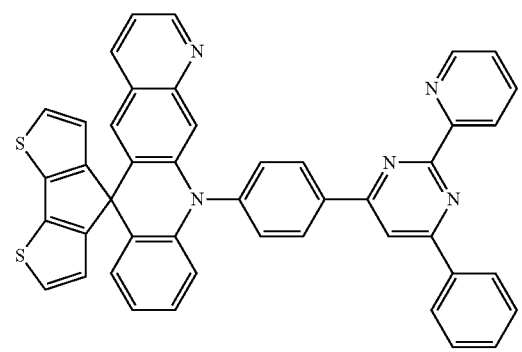
C82
C83
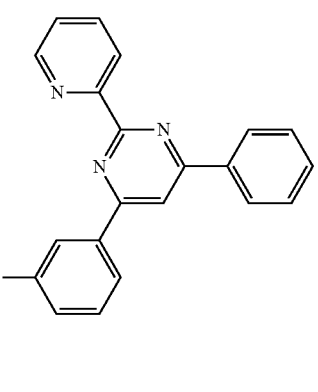

101
-continued
C84
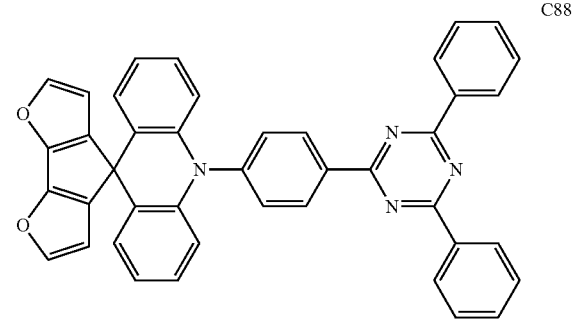
C85
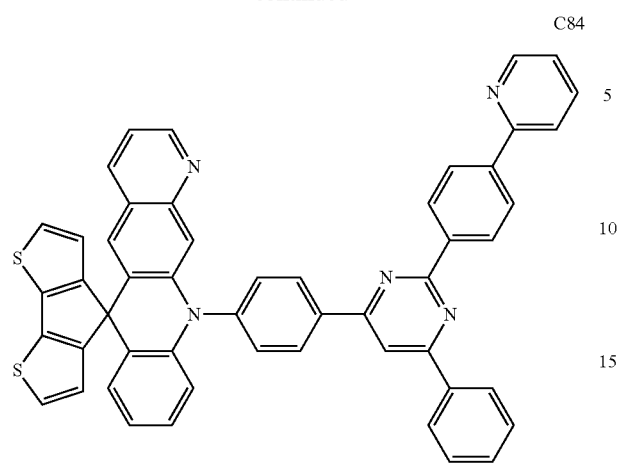
C86
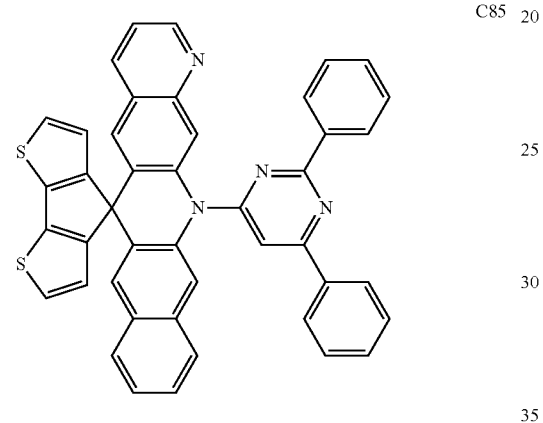
C87
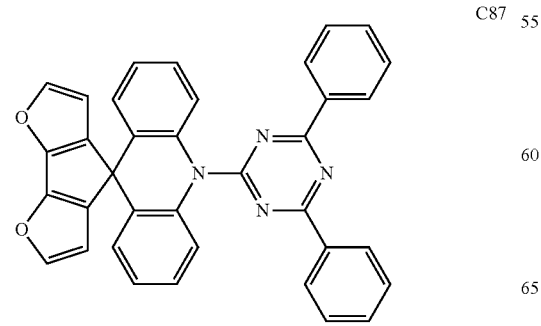
102
-continued
C88
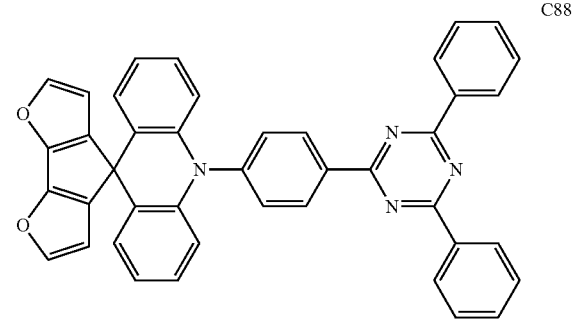
C89
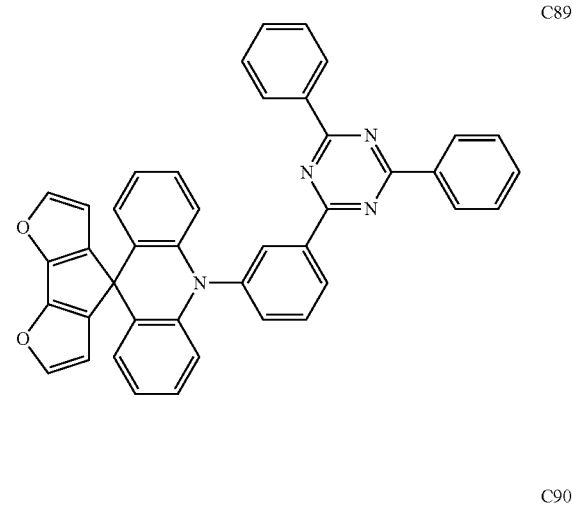
C90
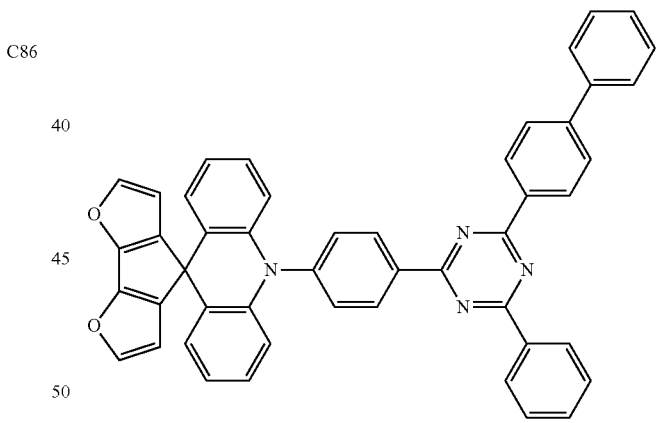
C91
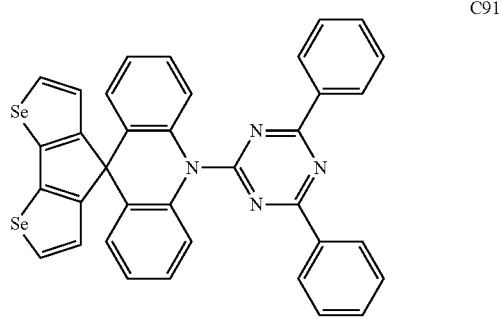

-continued
C92
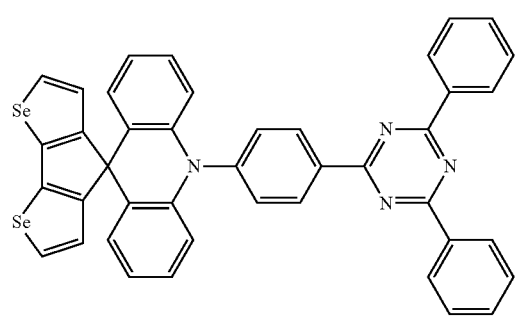
C93
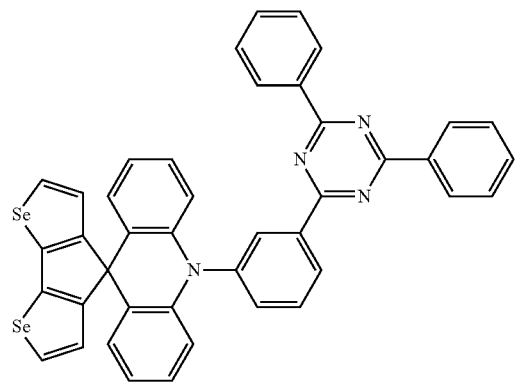
C94
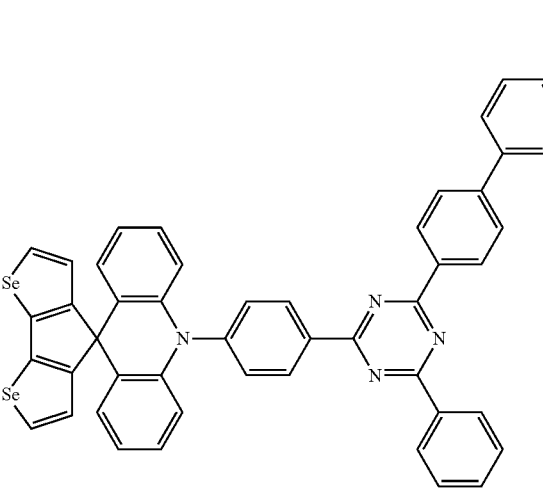
C95
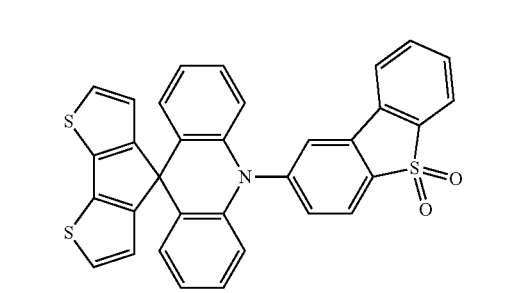
-continued
C96
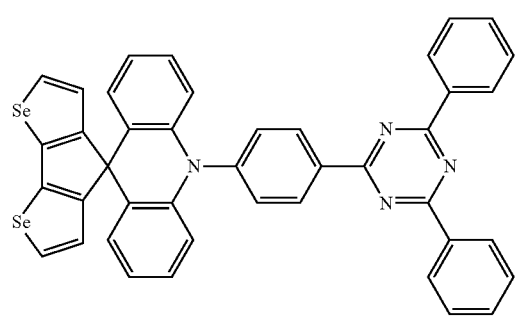
C97
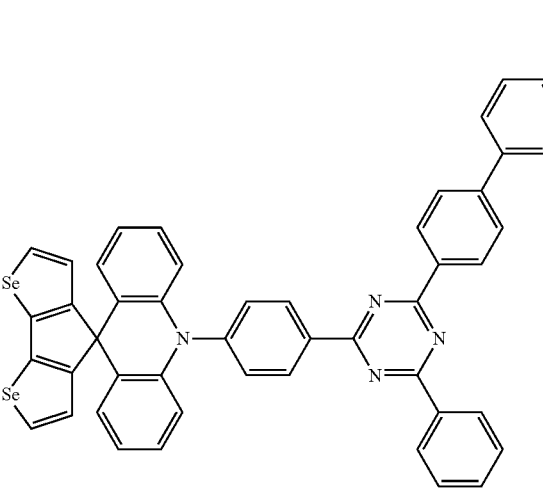
C98
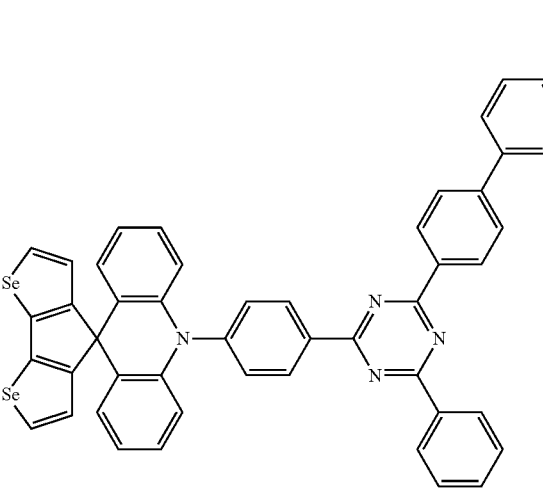
C99
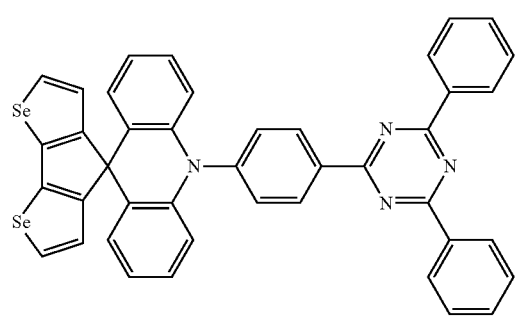
C100
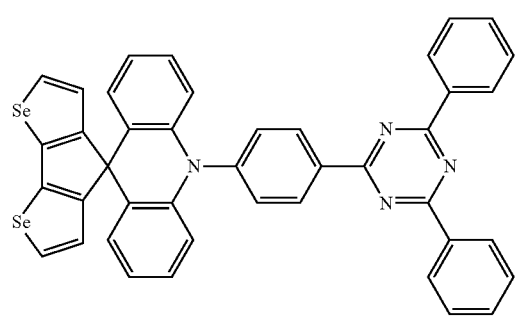

C101
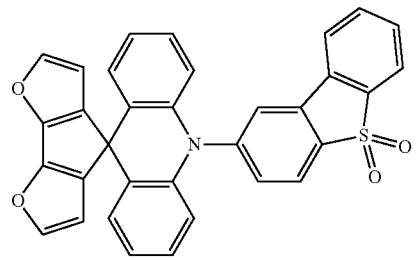
C102
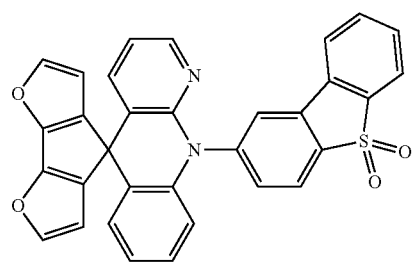
C103
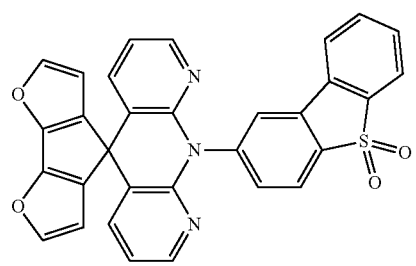
C104
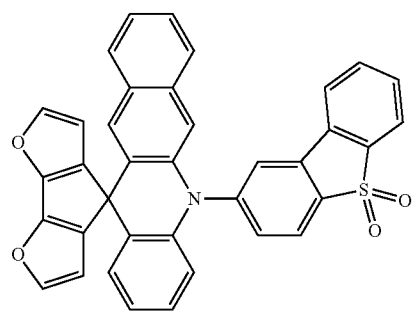
C105
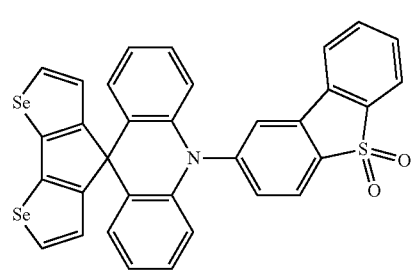
C106
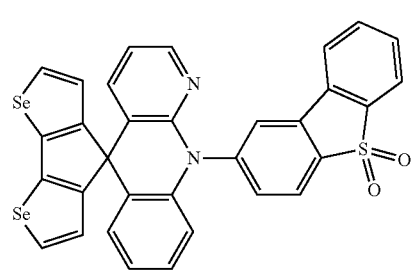
C107
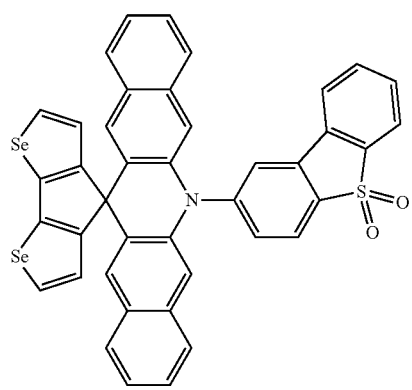
C108
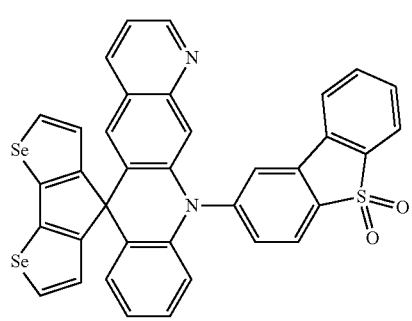
C109
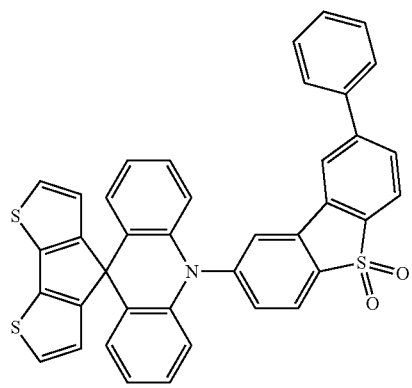
C110
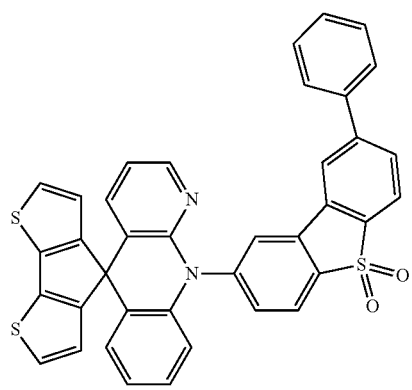

-continued
C111
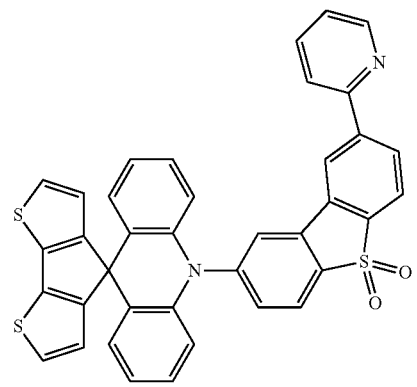
C112
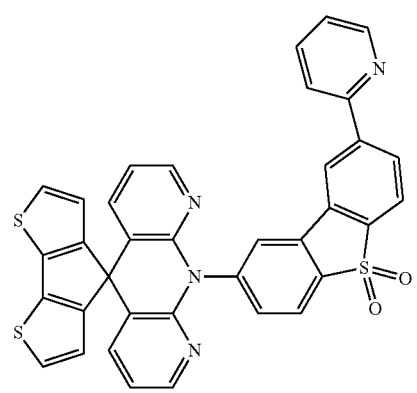
C113
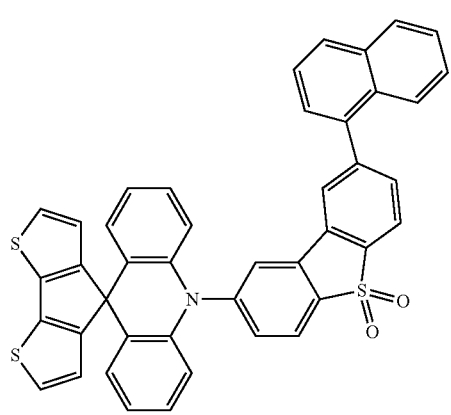
C114
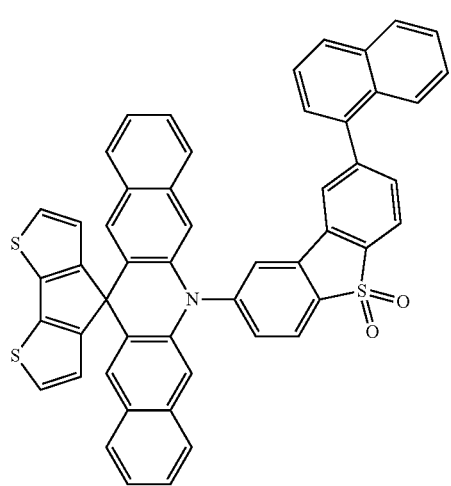
-continued
C115
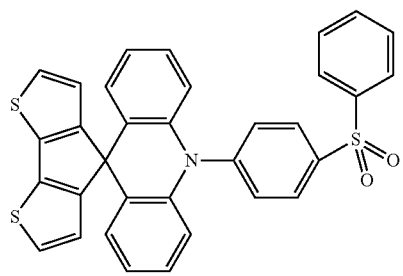
C116
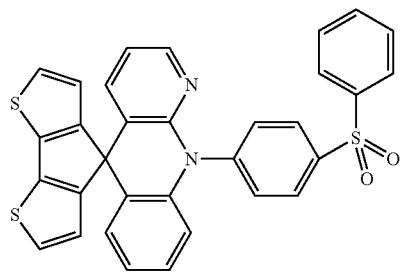
C117
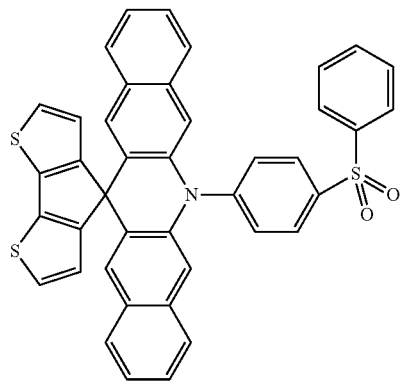
C118
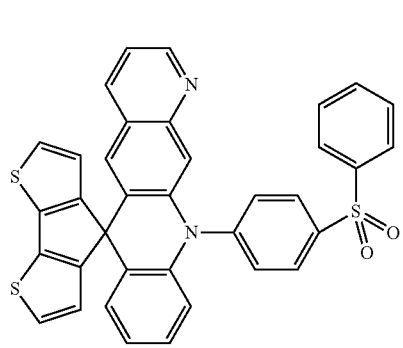
C119
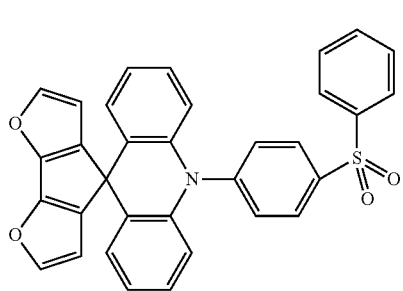

C120 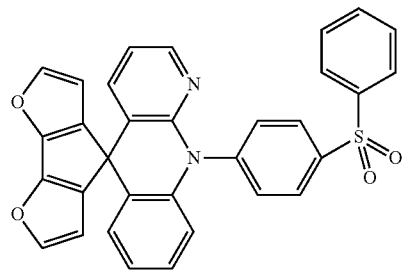
C121 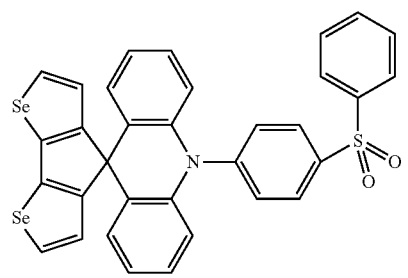
C122 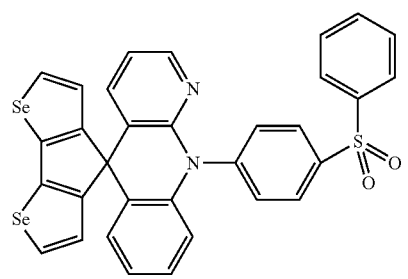
C123 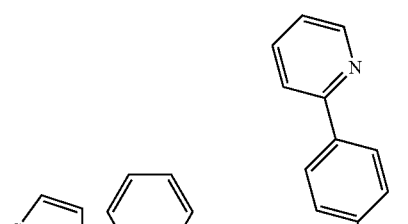
C124 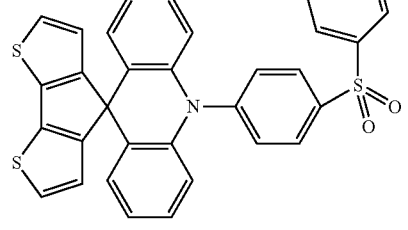
C125 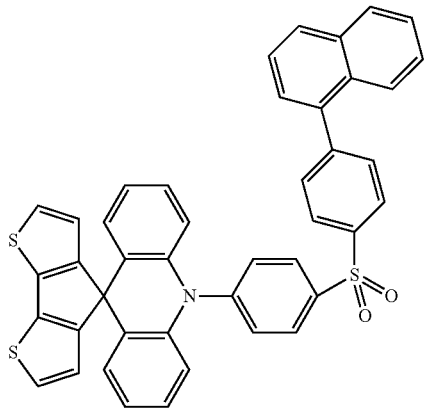
C126 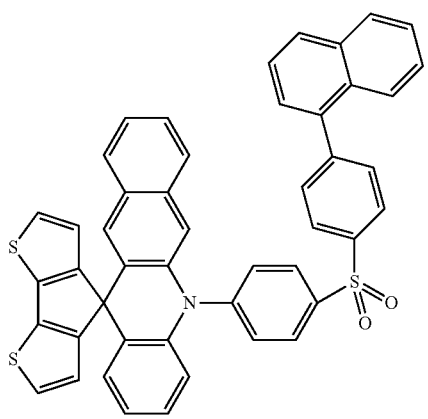
C127 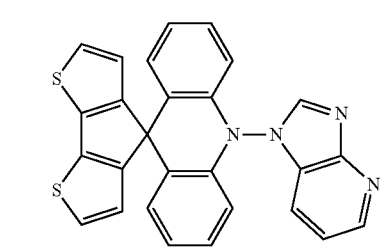
C128 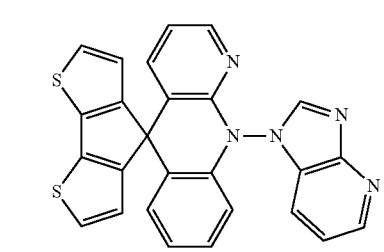
C129 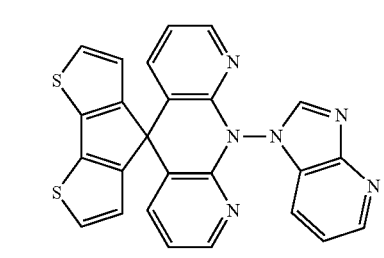

C130
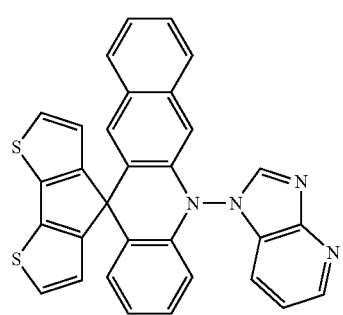
C131
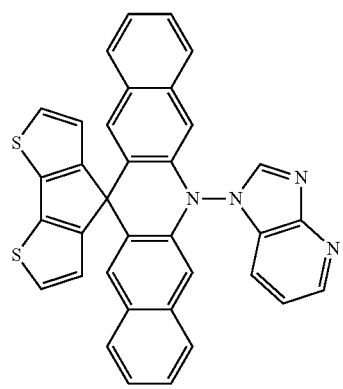
C132
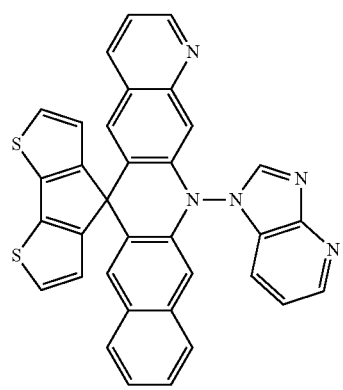
C133
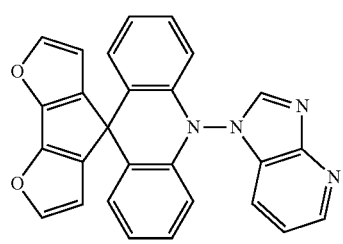
C134
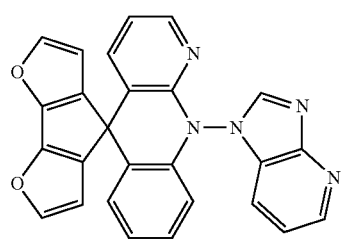
C135
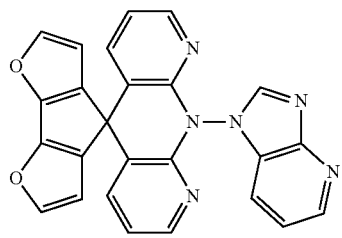
C136
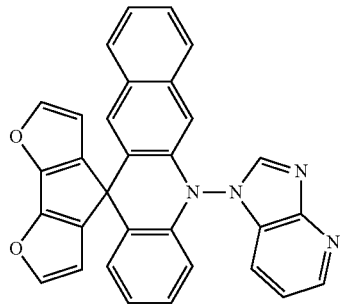
C137
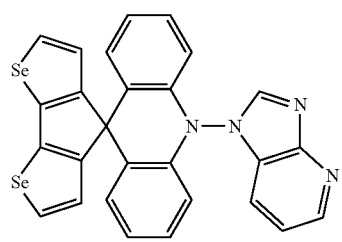
C138
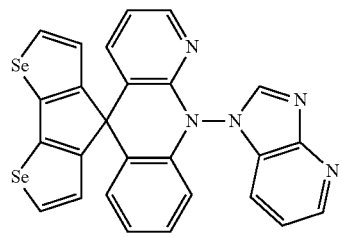
C139
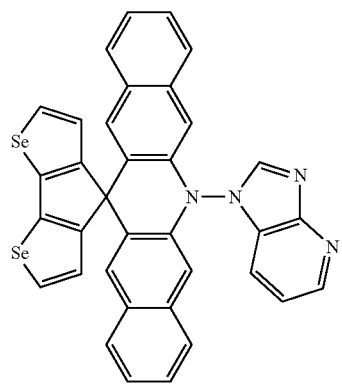

C140
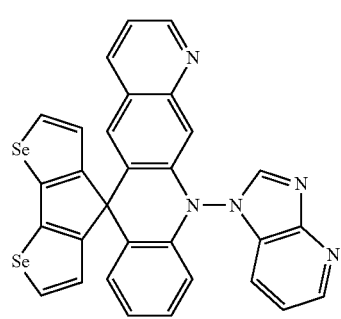
C143
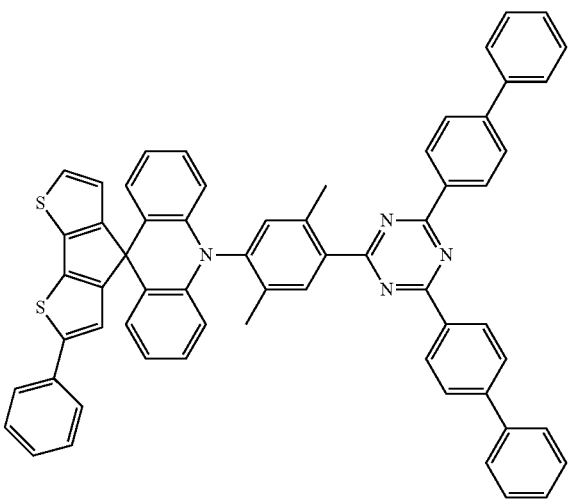
C141
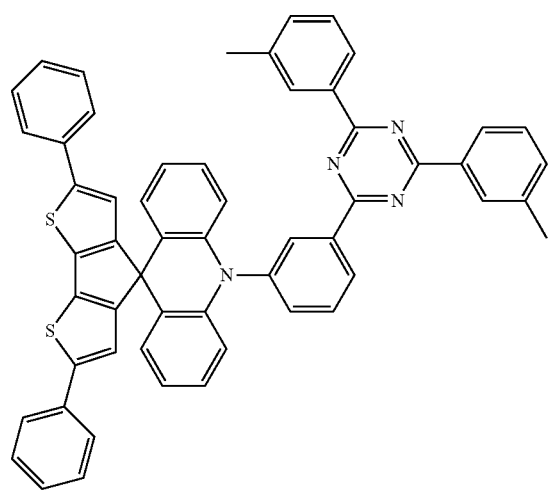
C144
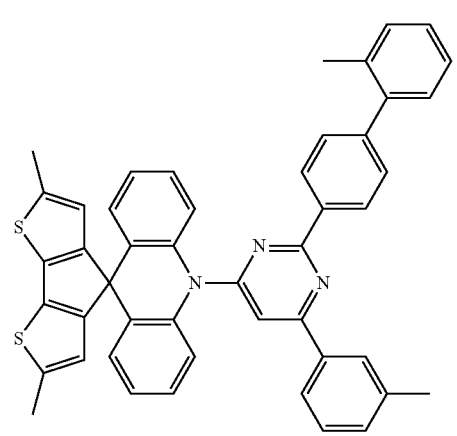
C142
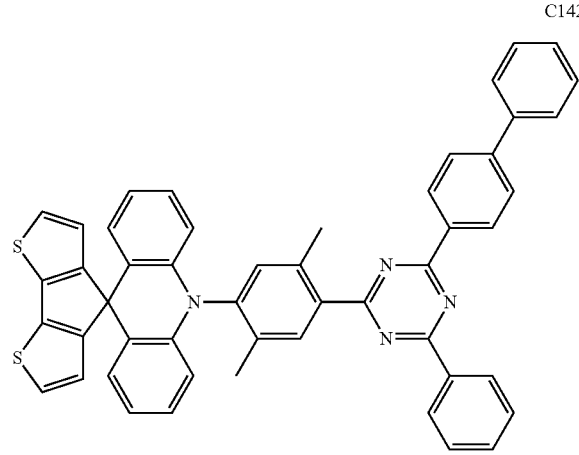
C145
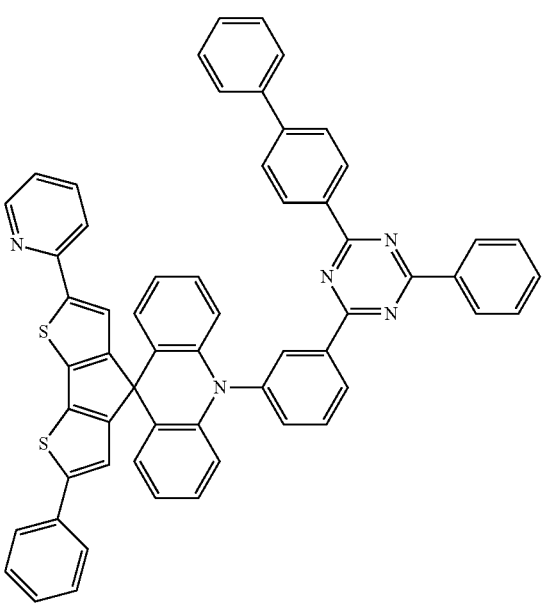

C146
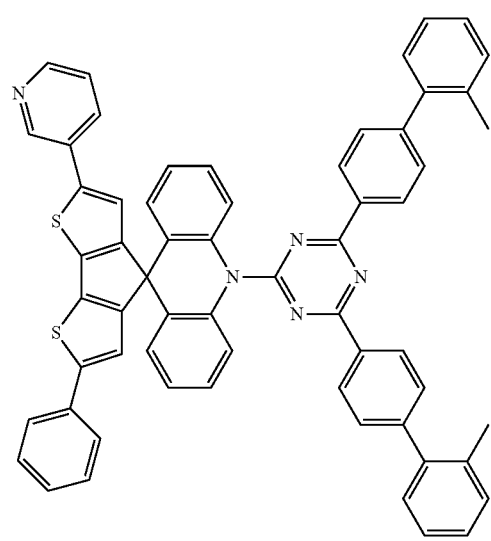
C147
C149
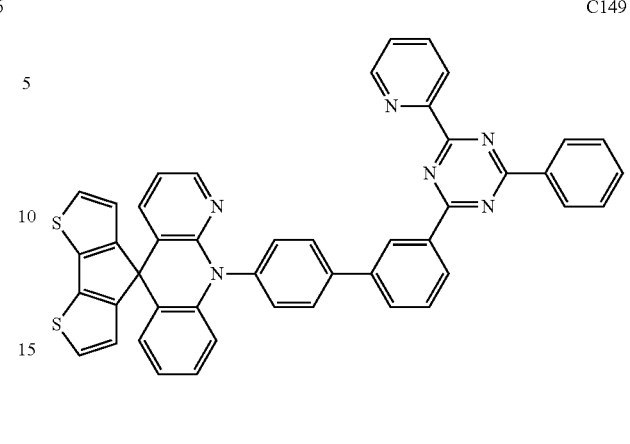
C150
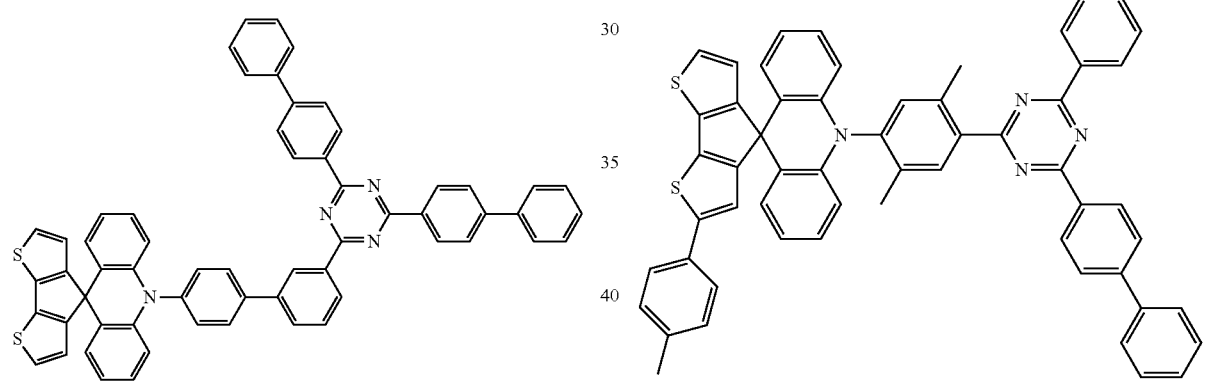
C148
C151
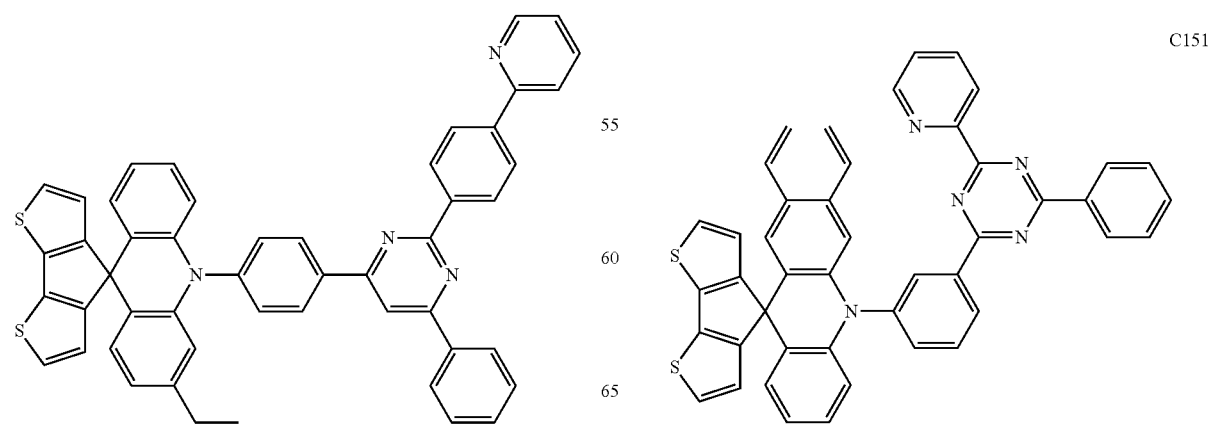

C152
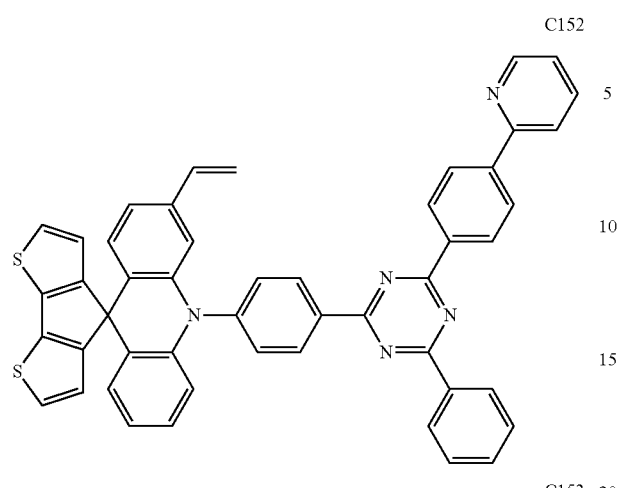
C153
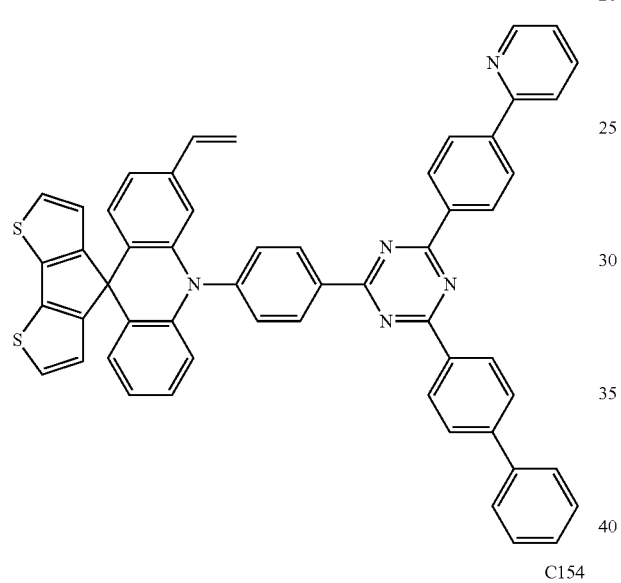
C154
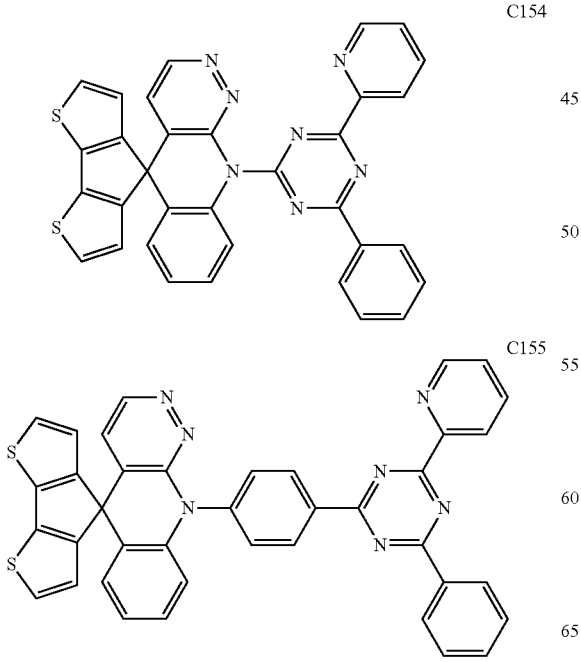
C155
C156
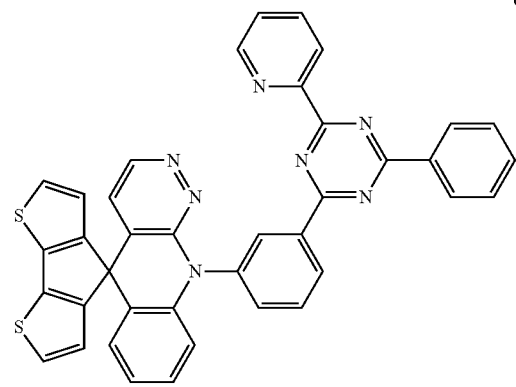
C157
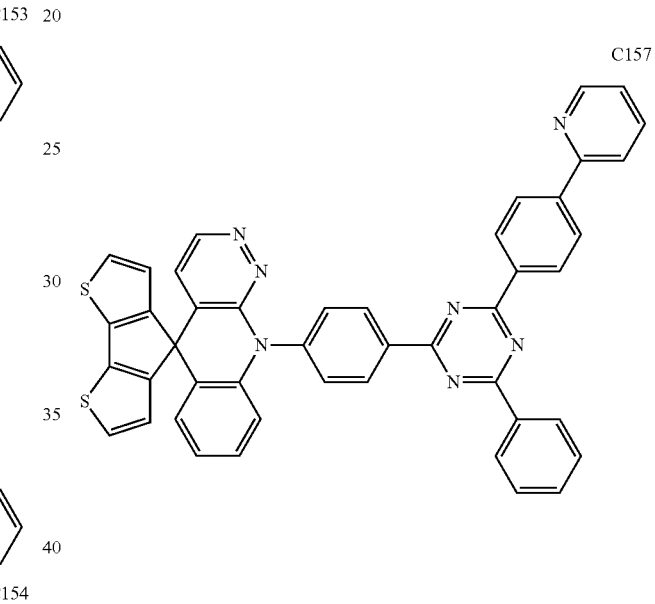
C158
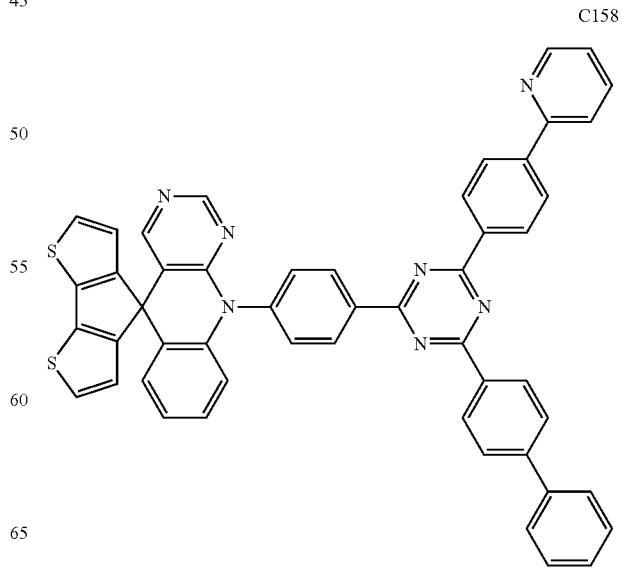

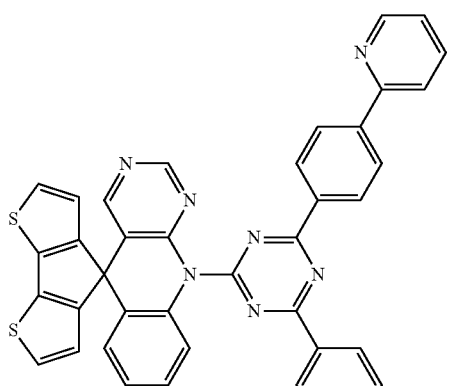
C159

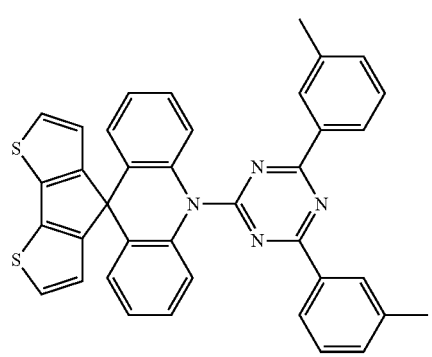
C160

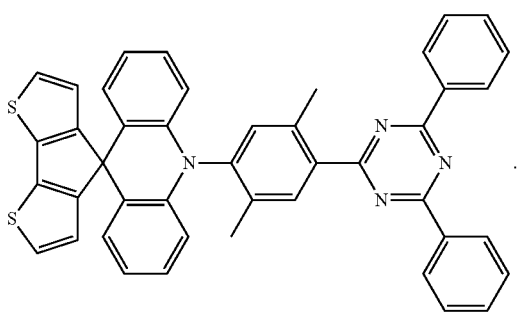
C161

4. An organic electroluminescent device, comprising a pair of electrodes composed of a cathode and an anode, and a light emitting layer and one or more organic thin film layers between the pair of electrodes, wherein the light emitting layer comprises two of the compounds of claim 3.

5. The delayed fluorescence compound of claim 1, wherein a difference between a singlet energy of the delayed fluorescence compound and a triplet energy of the delayed fluorescence compound is less than 0.3 eV.

6. The delayed fluorescence compound of claim 1, wherein the delayed fluorescence compound is used as a light-emitting material.

7. An organic electroluminescent device, comprising a pair of electrodes composed of a cathode and an anode, and a light emitting layer and one or more organic thin film layers between the pair of electrodes, wherein at least one of the light emitting layer and the organic thin film layer comprises the delayed fluorescence compound of claim 1.

8. The organic electroluminescent device of claim 7, wherein the light emitting layer comprising the delayed fluorescence compound is a delayed fluorescence host material.

9. The organic electroluminescent device of claim 8, wherein the light emitting layer further comprises a second fluorescence host material.

10. The organic electroluminescent device of claim 9, wherein the second fluorescence host material is the following compound:

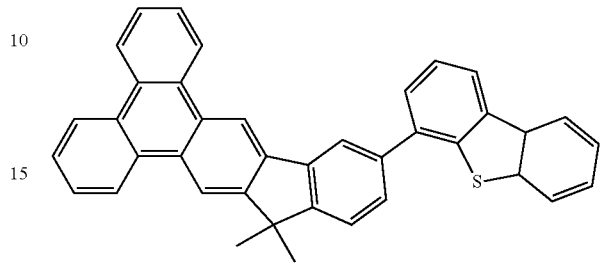

11. The organic electroluminescent device of claim 7, wherein the light emitting layer comprising the delayed fluorescence compound is a phosphorescent host material.

12. The organic electroluminescent device of claim 7, wherein the light emitting layer further includes a host material, and the delayed fluorescence compound is used as a dopant material.

13. The organic electroluminescent device of claim 12, wherein the host material is the following compound:

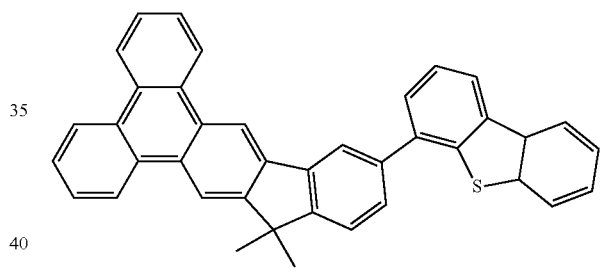

14. The organic electroluminescent device of claim 12, wherein the light emitting layer further comprises a second fluorescence dopant material.

15. The organic electroluminescent device of claim 7, wherein the organic thin film layer includes a hole injection layer, a hole transporting layer, a hole blocking layer, an electron transporting layer, and an electron injection layer, and at least one of the hole injection layer, the hole transporting layer, the hole blocking layer, the electron transporting layer, and the electron injection layer comprises the delayed fluorescence compound.

16. The organic electroluminescent device of claim 7, wherein the organic thin film layer comprising the delayed fluorescence compound is a hole blocking layer.

17. The organic electroluminescent device of claim 7, wherein the organic thin film layer comprising the delayed fluorescence compound is an electron transporting layer.

18. The organic electroluminescent device of claim 7, wherein the organic electroluminescent device is a lighting panel.

19. The organic electroluminescent device of claim 7, wherein the organic electroluminescent device is a backlight panel.

* * * * *